US012721893B2

(12) United States Patent
Wang et al.

(10) Patent No.: US 12,721,893 B2
(45) Date of Patent: Sep. 1, 2026

(54) ANTIGEN-BINDING PROTEIN TARGETING CD70 AND USE THEREOF

(71) Applicant: Cure Genetics Co., Ltd, Suzhou (CN)

(72) Inventors: Wenbo Wang, Suzhou (CN); Yanni Lin, Suzhou (CN)

( * ) Notice: Subject to any disclaimer, the term of this patent is extended or adjusted under 35 U.S.C. 154(b) by 589 days.

(21) Appl. No.: 18/255,332

(22) PCT Filed: Nov. 30, 2021

(86) PCT No.: PCT/CN2021/134248
§ 371 (c)(1),
(2) Date: May 31, 2023

(87) PCT Pub. No.: WO2022/116952
PCT Pub. Date: Jun. 9, 2022

(65) Prior Publication Data

US 2024/0024475 A1 Jan. 25, 2024

(30) Foreign Application Priority Data

Dec. 1, 2020 (CN) ......................... 202011382464.5

(51) Int. Cl.
*A61K 40/42* (2025.01)
*A61K 40/11* (2025.01)
*A61K 40/31* (2025.01)
*A61P 35/00* (2006.01)
*C12N 5/0783* (2010.01)

(52) U.S. Cl.
CPC .......... *A61K 40/4224* (2025.01); *A61K 40/11* (2025.01); *A61K 40/31* (2025.01); *A61K 40/4232* (2025.01); *A61P 35/00* (2018.01); *C12N 5/0636* (2013.01); *A61K 2239/17* (2023.05); *A61K 2239/21* (2023.05); *A61K 2239/31* (2023.05); *A61K 2239/38* (2023.05); *A61K 2239/46* (2023.05);
(Continued)

(58) Field of Classification Search
CPC ................................................. A61K 40/4224
See application file for complete search history.

(56) References Cited

U.S. PATENT DOCUMENTS

2017/0369581 A9 12/2017 Silence et al.

FOREIGN PATENT DOCUMENTS

CN 1252076 A 5/2000
CN 101370830 A 2/2009
(Continued)

OTHER PUBLICATIONS

International Search Report and Written Opinion for Int'l Application No. PCT/CN2021/134248, Date Mailed: Mar. 9, 2022 (English Translation of Search Report included).
Yang, M.J. et al. "Tandem CAR-T cells targeting CD70 and B7-H3 exhibit potent preclinical activity against multiple solid tumors," Theranostics, vol. 10, No. 17, pp. 7622-7634 (Jun. 18, 2020).
Alex Klarenbeek et al., Camelid Ig V genes reveal significant human homology not seen in therapeutic target genes, providing for a powerful therapeutic antibody platform, May 27, 2015, MABS, 693-706, vol. 7, No. 4.
(Continued)

*Primary Examiner* — Karl J Puttlitz

(57) ABSTRACT

An antigen-binding protein targeting CD70. In particular, the present invention relates to a chimeric antigen receptor containing the antigen binding protein and the use thereof, and cells containing or expressing the antigen binding protein. The antigen-binding protein binds to a CD70 protein at 1 nM of a $K_D$ value. The chimeric antigen receptor containing the antigen-binding protein has strong specific recognition and binding abilities to the CD70 protein. The cells containing or expressing the antigen-binding protein can secrete cytokines IL-2 and IFN-γ.

49 Claims, 5 Drawing Sheets

Specification includes a Sequence Listing.

CAR

| Promoter | Human CD8α signal peptide | VHH sequence of anti-human CD70 single domain antibody | Human CD8α hinge region | Human CD8α Transmembrane domain | 4-1BB co-stimulatory signaling domain | CD3ζ intracellular signaling domain |
|---|---|---|---|---|---|---|

(52) U.S. Cl.
CPC ...... *A61K 2239/48* (2023.05); *A61K 2239/56* (2023.05); *C12N 2510/00* (2013.01)

(56) References Cited

FOREIGN PATENT DOCUMENTS

| | | | |
|---|---|---|---|
| CN | 101605906 | A | 12/2009 |
| CN | 107207616 | A | 9/2017 |
| CN | 109880802 | A | 6/2019 |
| CN | 111909966 | A | 11/2020 |
| CN | 111936158 | A | 11/2020 |
| CN | 112739721 | A | 4/2021 |
| WO | 2015156673 | A1 | 10/2015 |
| WO | 2017/021354 | A1 | 2/2017 |
| WO | 2018152181 | A1 | 8/2018 |
| WO | 2021/197391 | A1 | 10/2021 |
| WO | 2022/116952 | A1 | 6/2022 |

OTHER PUBLICATIONS

Jayaraman Jayapriya et al, CAR-T design: Elements and their synergistic function, Jul. 30, 2020, Ebiomedicine, 102931, 58.

Karen Silence et al., ARGX-110, a highly potent antibody targeting CD70, eliminates tumors via both enhanced ADCC and immune checkpoint blockade, Dec. 6, 2013, MABS, 523-532, vol. 6, No. 2.

S V Kulemzin et al, Engineering Chimeric Antigen Receptors, Jan. 1, 2017, Acta Naturae, 6-14.

Sterner and Sterner, CAR-T cell therapy: current limitations and potential strategies, Apr. 6, 2021, Blood Cancer Journal, 1-11, 11:69.

Stijn De Munter, Abstract 82—Nanobody based CD70 specific chimeric antigen receptors to target both solid and liquid malignancies, May 23, 2019, 17th CIMT Annual Meeting, 22.

SEQUENCE LISTING

```
<160> NUMBER OF SEQ ID NOS: 94

<210> SEQ ID NO 1
<211> LENGTH: 8
<212> TYPE: PRT
<213> ORGANISM: Artificial Sequence
<220> FEATURE:
<223> OTHER INFORMATION: 1C HCDR1;H3 HCDR1;1H HCDR1

<400> SEQUENCE: 1

Gly Lys Pro Phe Ser Phe Tyr Phe
1               5


<210> SEQ ID NO 2
<211> LENGTH: 7
<212> TYPE: PRT
<213> ORGANISM: Artificial Sequence
<220> FEATURE:
<223> OTHER INFORMATION: 1C HCDR2;H3 HCDR2;1H HCDR2

<400> SEQUENCE: 2

Ile Thr Gly Asp Gly Met Thr
1               5


<210> SEQ ID NO 3
<211> LENGTH: 13
<212> TYPE: PRT
<213> ORGANISM: Artificial Sequence
<220> FEATURE:
<223> OTHER INFORMATION: 1C HCDR3

<400> SEQUENCE: 3

Tyr Ala Asp Ala Trp Ala Gly Ala Gly Arg Glu Glu Tyr
1               5                   10


<210> SEQ ID NO 4
<211> LENGTH: 13
<212> TYPE: PRT
<213> ORGANISM: Artificial Sequence
<220> FEATURE:
<223> OTHER INFORMATION: H3 HCDR3

<400> SEQUENCE: 4

Tyr Ala Asp Ala Trp Ala Gly Ala Val Arg Ala Glu Tyr
1               5                   10


<210> SEQ ID NO 5
<211> LENGTH: 13
<212> TYPE: PRT
<213> ORGANISM: Artificial Sequence
<220> FEATURE:
<223> OTHER INFORMATION: 1H HCDR3

<400> SEQUENCE: 5
```

Tyr Ala Asp Val Trp Ala Gly Ala Gly Arg Asp Glu Tyr
1 5 10

<210> SEQ ID NO 6
<211> LENGTH: 8
<212> TYPE: PRT
<213> ORGANISM: Artificial Sequence
<220> FEATURE:
<223> OTHER INFORMATION: 1F HCDR1

<400> SEQUENCE: 6

Gly Lys Arg Phe Ser Phe Tyr Phe
1 5

<210> SEQ ID NO 7
<211> LENGTH: 7
<212> TYPE: PRT
<213> ORGANISM: Artificial Sequence
<220> FEATURE:
<223> OTHER INFORMATION: 1F HCDR2;5H HCDR2

<400> SEQUENCE: 7

Ile Thr Gly Asp Gly Arg Thr
1 5

<210> SEQ ID NO 8
<211> LENGTH: 13
<212> TYPE: PRT
<213> ORGANISM: Artificial Sequence
<220> FEATURE:
<223> OTHER INFORMATION: 1F HCDR3

<400> SEQUENCE: 8

Tyr Ala Asp Ala Phe Ala Gly Ala Gly Arg Asp Glu Tyr
1 5 10

<210> SEQ ID NO 9
<211> LENGTH: 8
<212> TYPE: PRT
<213> ORGANISM: Artificial Sequence
<220> FEATURE:
<223> OTHER INFORMATION: 5H HCDR1

<400> SEQUENCE: 9

Gly Lys Ile Phe Ser Phe Tyr Phe
1 5

<210> SEQ ID NO 10
<211> LENGTH: 13
<212> TYPE: PRT
<213> ORGANISM: Artificial Sequence
<220> FEATURE:
<223> OTHER INFORMATION: 5H HCDR3

<400> SEQUENCE: 10

Tyr Ala Asp Val Phe Ala Arg Ala Gly Arg Asp Glu Tyr
1 5 10

<210> SEQ ID NO 11
<211> LENGTH: 8
<212> TYPE: PRT
<213> ORGANISM: Artificial Sequence
<220> FEATURE:
<223> OTHER INFORMATION: 3H HCDR1

<400> SEQUENCE: 11

Gly Asn Ile Leu Arg Phe Asn Ala

```
1               5


<210> SEQ ID NO 12
<211> LENGTH: 8
<212> TYPE: PRT
<213> ORGANISM: Artificial Sequence
<220> FEATURE:
<223> OTHER INFORMATION: 3H HCDR2

<400> SEQUENCE: 12

Met Ala Gly Ala Arg Thr Asn Tyr
1               5


<210> SEQ ID NO 13
<211> LENGTH: 10
<212> TYPE: PRT
<213> ORGANISM: Artificial Sequence
<220> FEATURE:
<223> OTHER INFORMATION: 3H HCDR3

<400> SEQUENCE: 13

Asp Arg Val Tyr Gly Pro Pro Tyr Glu Tyr
1               5                   10


<210> SEQ ID NO 14
<211> LENGTH: 8
<212> TYPE: PRT
<213> ORGANISM: Artificial Sequence
<220> FEATURE:
<223> OTHER INFORMATION: 1G HCDR1

<400> SEQUENCE: 14

Ser Gly Ile Ile Phe Asn Ser Asp
1               5


<210> SEQ ID NO 15
<211> LENGTH: 7
<212> TYPE: PRT
<213> ORGANISM: Artificial Sequence
<220> FEATURE:
<223> OTHER INFORMATION: 1G HCDR2

<400> SEQUENCE: 15

Leu Thr Ser Asn Met Arg Thr
1               5


<210> SEQ ID NO 16
<211> LENGTH: 13
<212> TYPE: PRT
<213> ORGANISM: Artificial Sequence
<220> FEATURE:
<223> OTHER INFORMATION: 1G HCDR3

<400> SEQUENCE: 16

Asn Val Asn Arg Met Thr Ser Tyr Gly Pro Arg Asp Tyr
1               5                   10


<210> SEQ ID NO 17
<211> LENGTH: 8
<212> TYPE: PRT
<213> ORGANISM: Artificial Sequence
<220> FEATURE:
<223> OTHER INFORMATION: L1 HCDR1

<400> SEQUENCE: 17

Gly Arg Thr Phe Ser Ser Tyr Ala
1               5
```

<210> SEQ ID NO 18
<211> LENGTH: 8
<212> TYPE: PRT
<213> ORGANISM: Artificial Sequence
<220> FEATURE:
<223> OTHER INFORMATION: L1 HCDR2

<400> SEQUENCE: 18

Ile Asn Trp Ser Asp Gly Ser Thr
1 5

<210> SEQ ID NO 19
<211> LENGTH: 17
<212> TYPE: PRT
<213> ORGANISM: Artificial Sequence
<220> FEATURE:
<223> OTHER INFORMATION: L1 HCDR3

<400> SEQUENCE: 19

Ala Ala Gly Cys Cys Gly Val Ala Asp Ala Pro Leu Asn Ala Leu Asp
1 5 10 15

Ala

<210> SEQ ID NO 20
<211> LENGTH: 8
<212> TYPE: PRT
<213> ORGANISM: Artificial Sequence
<220> FEATURE:
<223> OTHER INFORMATION: 5A HCDR1

<400> SEQUENCE: 20

Glu Ser Ile Phe Asn Asn Tyr Val
1 5

<210> SEQ ID NO 21
<211> LENGTH: 7
<212> TYPE: PRT
<213> ORGANISM: Artificial Sequence
<220> FEATURE:
<223> OTHER INFORMATION: 5A HCDR2

<400> SEQUENCE: 21

Ile Ser Thr Asp Gly Ser Ala
1 5

<210> SEQ ID NO 22
<211> LENGTH: 6
<212> TYPE: PRT
<213> ORGANISM: Artificial Sequence
<220> FEATURE:
<223> OTHER INFORMATION: 5A HCDR3

<400> SEQUENCE: 22

Thr Ala Gly Leu Gln Tyr
1 5

<210> SEQ ID NO 23
<211> LENGTH: 8
<212> TYPE: PRT
<213> ORGANISM: Artificial Sequence
<220> FEATURE:
<223> OTHER INFORMATION: 7D HCDR1;5B HCDR1

<400> SEQUENCE: 23

Gly Phe Thr Phe Asp Asp Tyr Ala 1 5

<210> SEQ ID NO 24
<211> LENGTH: 8
<212> TYPE: PRT
<213> ORGANISM: Artificial Sequence
<220> FEATURE:
<223> OTHER INFORMATION: 7D HCDR2

<400> SEQUENCE: 24

Ile Arg Arg Ser Asp Gly Ser Thr
1 5

<210> SEQ ID NO 25
<211> LENGTH: 18
<212> TYPE: PRT
<213> ORGANISM: Artificial Sequence
<220> FEATURE:
<223> OTHER INFORMATION: 7D HCDR3

<400> SEQUENCE: 25

Ala Val Asp Arg Tyr Gly Gln Ser Trp His Glu Gly Arg Gly Ala Leu
1 5 10 15

Asp Ala

<210> SEQ ID NO 26
<211> LENGTH: 8
<212> TYPE: PRT
<213> ORGANISM: Artificial Sequence
<220> FEATURE:
<223> OTHER INFORMATION: L2 HCDR1

<400> SEQUENCE: 26

Gly Phe Thr Val Asp Asp Tyr Val
1 5

<210> SEQ ID NO 27
<211> LENGTH: 8
<212> TYPE: PRT
<213> ORGANISM: Artificial Sequence
<220> FEATURE:
<223> OTHER INFORMATION: L2 HCDR2

<400> SEQUENCE: 27

Ile Ser Ser Asn Asp Gly Ser Thr
1 5

<210> SEQ ID NO 28
<211> LENGTH: 18
<212> TYPE: PRT
<213> ORGANISM: Artificial Sequence
<220> FEATURE:
<223> OTHER INFORMATION: L2 HCDR3

<400> SEQUENCE: 28

Ala Ala Lys Tyr Ala Pro Tyr Gly Leu Glu Tyr Trp Glu Gly Gly Met
1 5 10 15

Asp Tyr

<210> SEQ ID NO 29
<211> LENGTH: 8
<212> TYPE: PRT
<213> ORGANISM: Artificial Sequence
<220> FEATURE:
<223> OTHER INFORMATION: 1E HCDR1

<400> SEQUENCE: 29

Gly Phe Ala Phe Asp Asp Tyr Ala
1 5

<210> SEQ ID NO 30
<211> LENGTH: 8
<212> TYPE: PRT
<213> ORGANISM: Artificial Sequence
<220> FEATURE:
<223> OTHER INFORMATION: 1E HCDR2

<400> SEQUENCE: 30

Met Ser Ser Ser Asp Gly Ser Thr
1 5

<210> SEQ ID NO 31
<211> LENGTH: 18
<212> TYPE: PRT
<213> ORGANISM: Artificial Sequence
<220> FEATURE:
<223> OTHER INFORMATION: 1E HCDR3

<400> SEQUENCE: 31

Ala Ala Gly Val Asn Tyr Tyr Arg Glu Asp Gly Cys Pro Gly Ala Leu
1 5 10 15

Asp Tyr

<210> SEQ ID NO 32
<211> LENGTH: 8
<212> TYPE: PRT
<213> ORGANISM: Artificial Sequence
<220> FEATURE:
<223> OTHER INFORMATION: 5B HCDR2

<400> SEQUENCE: 32

Phe Arg Ser Ser Asp Gly Asn Ile
1 5

<210> SEQ ID NO 33
<211> LENGTH: 19
<212> TYPE: PRT
<213> ORGANISM: Artificial Sequence
<220> FEATURE:
<223> OTHER INFORMATION: 5B HCDR3

<400> SEQUENCE: 33

Ala Ala Tyr Ser Val Leu Leu Arg Pro Trp Val Leu Cys Glu Gly Ser
1 5 10 15

Tyr Asp Tyr

<210> SEQ ID NO 34
<211> LENGTH: 119
<212> TYPE: PRT
<213> ORGANISM: Artificial Sequence
<220> FEATURE:
<223> OTHER INFORMATION: CD70-sdAb-1C

<400> SEQUENCE: 34

Glu Val Gln Val Val Glu Ser Gly Gly Gly Met Val Gln Ala Gly Arg
1 5 10 15

Ser Leu Arg Leu Ser Cys Ala Ala Ser Gly Lys Pro Phe Ser Phe Tyr
20 25 30

Phe Met Gly Trp Tyr Arg Gln Ala Pro Gly Asn Gln Arg Glu Leu Val
35 40 45

```
Ala Leu Ile Thr Gly Asp Gly Met Thr Asn Tyr Ala Asp Ser Val Glu
    50                  55                  60

Gly Arg Phe Thr Ile Ser Arg Asp Asn Ala Lys Asn Thr Met Tyr Leu
65                  70                  75                  80

Glu Met Asn Ser Leu Lys Pro Glu Asp Thr Ala Val Tyr Tyr Cys Tyr
                85                  90                  95

Ala Asp Ala Trp Ala Gly Ala Gly Arg Glu Glu Tyr Trp Gly Gln Gly
            100                 105                 110

Thr Gln Val Ser Val Ser Ser
        115


<210> SEQ ID NO 35
<211> LENGTH: 125
<212> TYPE: PRT
<213> ORGANISM: Artificial Sequence
<220> FEATURE:
<223> OTHER INFORMATION: CD70-sdAb-1E

<400> SEQUENCE: 35

Glu Val Gln Val Val Glu Ser Gly Gly Gly Leu Val Gln Ala Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Lys Glu Gln Glu Arg Val
        35                  40                  45

Ser Cys Met Ser Ser Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Val Asn Tyr Tyr Arg Glu Asp Gly Cys Pro Gly Ala Leu
            100                 105                 110

Asp Tyr Trp Gly Gln Gly Thr Gln Val Thr Val Ser Ser
        115                 120                 125


<210> SEQ ID NO 36
<211> LENGTH: 119
<212> TYPE: PRT
<213> ORGANISM: Artificial Sequence
<220> FEATURE:
<223> OTHER INFORMATION: CD70-sdAb-1F

<400> SEQUENCE: 36

Glu Val Gln Val Val Glu Ser Gly Gly Gly Met Val Gln Ala Gly Gly
1               5                   10                  15

Ser Leu Arg Leu Ser Cys Ala Ala Ser Gly Lys Arg Phe Ser Phe Tyr
            20                  25                  30

Phe Met Gly Trp Tyr Arg Gln Ala Pro Gly Lys Gln Arg Glu Leu Val
        35                  40                  45

Ala Leu Ile Thr Gly Asp Gly Arg Thr Asn Tyr Ala Gly Ser Val Glu
    50                  55                  60

Gly Arg Phe Thr Ile Ser Arg Asp Asn Ala Lys Asn Thr Leu Tyr Leu
65                  70                  75                  80

Gln Met Asn Ser Met Lys Pro Glu Asp Thr Ala Val Tyr Tyr Cys Tyr
                85                  90                  95

Ala Asp Ala Phe Ala Gly Ala Gly Arg Asp Glu Tyr Trp Gly Gln Gly
```

```
            100                 105                 110

Thr Gln Val Ser Val Ser Ser
        115


<210> SEQ ID NO 37
<211> LENGTH: 118
<212> TYPE: PRT
<213> ORGANISM: Artificial Sequence
<220> FEATURE:
<223> OTHER INFORMATION: CD70-sdAb-1G

<400> SEQUENCE: 37

Gln Leu Gln Leu Val Glu Ser Gly Gly Gly Leu Val Gln Leu Gly Gly
1               5                   10                  15

Ser Leu Thr Leu Ser Cys Thr Ala Ser Gly Ile Ile Phe Asn Ser Asp
            20                  25                  30

Tyr Val Gly Trp Tyr Arg Gln Ala Pro Gly Ser Asp Arg Glu Leu Val
        35                  40                  45

Ala Leu Thr Ser Asn Met Arg Thr Asn Tyr Ala Asp Ser Val Glu Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Asn Val
                85                  90                  95

Asn Arg Met Thr Ser Tyr Gly Pro Arg Asp Tyr Trp Gly Gln Gly Thr
            100                 105                 110

Gln Val Thr Val Ser Ser
        115


<210> SEQ ID NO 38
<211> LENGTH: 119
<212> TYPE: PRT
<213> ORGANISM: Artificial Sequence
<220> FEATURE:
<223> OTHER INFORMATION: CD70-sdAb-1H

<400> SEQUENCE: 38

Glu Val Gln Leu Val Glu Ser Gly Gly Gly Met Val Gln Ala Gly Gly
1               5                   10                  15

Ser Leu Arg Leu Ser Cys Ala Ala Ser Gly Lys Pro Phe Ser Phe Tyr
            20                  25                  30

Phe Met Gly Trp Tyr Arg Gln Ala Pro Gly Lys Gln Arg Glu Leu Val
        35                  40                  45

Ala Leu Ile Thr Gly Asp Gly Met Thr Asn Tyr Ala Asp Ser Val Glu
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Tyr
                85                  90                  95

Ala Asp Val Trp Ala Gly Ala Gly Arg Asp Glu Tyr Trp Gly Gln Gly
            100                 105                 110

Thr Arg Val Thr Val Ser Ser
        115


<210> SEQ ID NO 39
<211> LENGTH: 117
<212> TYPE: PRT
<213> ORGANISM: Artificial Sequence
<220> FEATURE:
```

```
<223> OTHER INFORMATION: CD70-sdAb-3H

<400> SEQUENCE: 39

Gln Leu Gln Leu Val Glu Ser Gly Gly Gly Leu Val Gln Pro Gly Gly
1               5                   10                  15

Ser Leu Arg Leu Ser Cys Ala Ala Ser Gly Asn Ile Leu Arg Phe Asn
            20                  25                  30

Ala Val Gly Trp Tyr Arg Gln Ala Pro Gly Lys Gln Arg Asp Leu Val
        35                  40                  45

Ala Ala Met Ala Gly Ala Arg Thr Asn Tyr Ala Asp Ser Val Glu Gly
    50                  55                  60

Arg Phe Thr Ile Ser Gly Asn Asn Ala Asn Asn Thr Val Tyr Leu Gln
65                  70                  75                  80

Met Asn Ser Leu Lys Pro Glu Asp Thr Gly Val Tyr Tyr Cys Gly Ala
                85                  90                  95

Asp Arg Val Tyr Gly Pro Pro Tyr Glu Tyr Gly Gly Arg Gly Thr Gln
            100                 105                 110

Val Thr Val Leu Ser
        115


<210> SEQ ID NO 40
<211> LENGTH: 112
<212> TYPE: PRT
<213> ORGANISM: Artificial Sequence
<220> FEATURE:
<223> OTHER INFORMATION: CD70-sdAb-5A

<400> SEQUENCE: 40

Glu Val Gln Leu Val Glu Ser Gly Gly Gly Leu Val Gln Ala Gly Gly
1               5                   10                  15

Ser Leu Arg Leu Ser Cys Ala Ala Ser Glu Ser Ile Phe Asn Asn Tyr
            20                  25                  30

Val Met Ala Trp Tyr Arg Gln Pro Pro Gly Lys Gln Arg Glu Ala Val
        35                  40                  45

Ala Gln Ile Ser Thr Asp Gly Ser Ala Tyr Tyr Gln Asp Arg Val Lys
    50                  55                  60

Gly Arg Phe Thr Ile Ser Arg Asp Asn Ala Lys Asn Leu Val Asn Leu
65                  70                  75                  80

Gln Met Ser Ser Leu Lys Pro Glu Asp Thr Ala Val Tyr Tyr Cys Thr
                85                  90                  95

Ala Gly Leu Gln Tyr Trp Gly Gln Gly Thr Gln Val Thr Val Ser Ser
            100                 105                 110


<210> SEQ ID NO 41
<211> LENGTH: 126
<212> TYPE: PRT
<213> ORGANISM: Artificial Sequence
<220> FEATURE:
<223> OTHER INFORMATION: CD70-sdAb-5B

<400> SEQUENCE: 41

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Pro Glu Gly Val
        35                  40                  45

Ser Cys Phe Arg Ser Ser Asp Gly Asn Ile Tyr Tyr Ser Asp Ser Val
```

```
    50                  55                  60

Arg Gly Arg Phe Thr Ile Ser Ser Asp Asn Ala Lys Asn Thr Val Tyr
65                  70                  75                  80

Leu Gln Met Asn Arg Leu Lys Pro Glu Asp Thr Ala Val Tyr Tyr Cys
                85                  90                  95

Ala Ala Tyr Ser Val Leu Leu Arg Pro Trp Val Leu Cys Glu Gly Ser
            100                 105                 110

Tyr Asp Tyr Trp Gly Gln Gly Thr Gln Val Thr Val Ser Ser
        115                 120                 125


<210> SEQ ID NO 42
<211> LENGTH: 119
<212> TYPE: PRT
<213> ORGANISM: Artificial Sequence
<220> FEATURE:
<223> OTHER INFORMATION: CD70-sdAb-5H

<400> SEQUENCE: 42

Glu Val Gln Leu Val Glu Ser Gly Gly Gly Met Val Gln Ala Gly Gly
1               5                   10                  15

Ser Leu Arg Leu Ser Cys Ala Ala Pro Gly Lys Ile Phe Ser Phe Tyr
            20                  25                  30

Phe Met Gly Trp Tyr Arg Gln Ala Pro Gly Lys Gln Arg Glu Leu Val
        35                  40                  45

Ala Leu Ile Thr Gly Asp Gly Arg Thr Asn Tyr Ala Asp Ser Val Glu
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Val Phe Ala Arg Ala Gly Arg Asp Glu Tyr Trp Gly Gln Gly
            100                 105                 110

Thr Gln Val Ser Val Ser Ser
        115


<210> SEQ ID NO 43
<211> LENGTH: 125
<212> TYPE: PRT
<213> ORGANISM: Artificial Sequence
<220> FEATURE:
<223> OTHER INFORMATION: CD70-sdAb-7D

<400> SEQUENCE: 43

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Gln Glu Gly Val
        35                  40                  45

Ser Cys Ile Arg Arg Ser Asp Gly Ser Thr Trp Tyr Ala Asn Ser Val
    50                  55                  60

Lys Gly Arg Phe Thr Ile Ser Asn Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Asp Arg Tyr Gly Gln Ser Trp His Glu Gly Arg Gly Ala Leu
            100                 105                 110
```

```
Asp Ala Trp Gly Gln Gly Thr Leu Val Thr Val Ser Ser
        115                 120                 125


<210> SEQ ID NO 44
<211> LENGTH: 119
<212> TYPE: PRT
<213> ORGANISM: Artificial Sequence
<220> FEATURE:
<223> OTHER INFORMATION: CD70-sdAb-H3

<400> SEQUENCE: 44

Gln Val Gln Leu Val Glu Ser Gly Gly Gly Met Val Gln Ala Gly Arg
1               5                   10                  15

Ser Leu Arg Leu Ser Cys Ala Ala Ser Gly Lys Pro Phe Ser Phe Tyr
            20                  25                  30

Phe Met Gly Trp Tyr Arg Gln Ala Pro Gly Lys Glu Arg Glu Leu Val
        35                  40                  45

Ala Leu Ile Thr Gly Asp Gly Met Thr Asn Tyr Ala Asp Ser Val Glu
    50                  55                  60

Gly Arg Phe Thr Ile Ser Arg Asp Asn Ala Lys Asn Thr Leu Tyr Leu
65                  70                  75                  80

Glu Met Asn Ser Leu Lys Pro Glu Asp Thr Ala Val Tyr Tyr Cys Tyr
                85                  90                  95

Ala Asp Ala Trp Ala Gly Ala Val Arg Ala Glu Tyr Trp Gly Gln Gly
            100                 105                 110

Thr Gln Val Ser Val Ser Ser
        115


<210> SEQ ID NO 45
<211> LENGTH: 125
<212> TYPE: PRT
<213> ORGANISM: Artificial Sequence
<220> FEATURE:
<223> OTHER INFORMATION: CD70-sdAb-L2

<400> SEQUENCE: 45

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Val Asp Asp Tyr
            20                  25                  30

Val Ile Gly Trp Phe Arg Gln Ala Pro Gly Lys Glu His Glu Gly Val
        35                  40                  45

Ser Cys Ile Ser Ser Asn Asp Gly Ser Thr Trp Tyr Ala Asp Ser Val
    50                  55                  60

Lys Gly Arg Phe Thr Ile Ser Ser Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Lys Tyr Ala Pro Tyr Gly Leu Glu Tyr Trp Glu Gly Gly Met
            100                 105                 110

Asp Tyr Trp Gly Lys Gly Thr Leu Val Thr Val Ser Ser
        115                 120                 125


<210> SEQ ID NO 46
<211> LENGTH: 124
<212> TYPE: PRT
<213> ORGANISM: Artificial Sequence
<220> FEATURE:
<223> OTHER INFORMATION: CD70-sdAb-L1
```

<400> SEQUENCE: 46

```
Glu Val Gln Val Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Val Arg Gln Ala Pro Gly Lys Asp Gln Glu Phe Val
        35                  40                  45

Ala Ala Ile Asn Trp Ser Asp Gly Ser Thr Tyr Tyr Ala Asp Ser Val
    50                  55                  60

Lys Gly Arg Phe Thr Ile Ala Arg Asp Asn Ala Lys Asn Thr Ala Phe
65                  70                  75                  80

Leu Gln Met Asn Ser Leu Lys Pro Glu Asp Thr Ala Val Tyr Tyr Cys
                85                  90                  95

Ala Ala Gly Cys Cys Gly Val Ala Asp Ala Pro Leu Asn Ala Leu Asp
            100                 105                 110

Ala Trp Gly Gln Gly Thr Leu Val Thr Val Ser Ser
        115                 120
```

<210> SEQ ID NO 47
<211> LENGTH: 357
<212> TYPE: DNA
<213> ORGANISM: Artificial Sequence
<220> FEATURE:
<223> OTHER INFORMATION: Nucleic acid sequence of CD70-sdAb-1C

<400> SEQUENCE: 47

```
gaggtgcagg tggtggagtc gggggaggga atggtgcagg ctgggcgatc tctgagactc     60

tcctgtgctg cctctggaaa gcccttcagt ttctatttca tgggatggta tcgccaggct    120

ccaggaaacc agcgcgagtt ggtcgccctt attaccggtg atggtatgac aaactatgca    180

gactccgtgg agggccgatt caccatctcc agagacaacg ccaagaatac aatgtatctc    240

gaaatgaaca gcctgaaacc tgaggacaca gccgtctatt attgctatgc agatgcttgg    300

gcgggggccg gccgcgaaga gtactggggc caggggaccc aggtcagcgt ctcctca       357
```

<210> SEQ ID NO 48
<211> LENGTH: 375
<212> TYPE: DNA
<213> ORGANISM: Artificial Sequence
<220> FEATURE:
<223> OTHER INFORMATION: Nucleic acid sequence of CD70-sdAb-1E

<400> SEQUENCE: 48

```
gaggtgcagg tggtggagtc tgggggaggc ttggtgcagg ctggggggtc tctgagactc     60

tcctgtgcag cctctggatt cgctttcgat gattatgcca taggctggtt ccgccaggcc    120

ccagggaagg agcaggaaag agtctcatgt atgagtagta gtgatggtag cacatactat    180

gcagactccg tgaagggccg attcaccatc tccagtgaca acgccaagaa cacggtgtat    240

ctgcaaatga acagcctgaa acctgaggac acggccgttt attactgtgc cgcaggggtc    300

aattactatc gcgaggatgg gtgcccgggc gcgttggact actggggcca ggggacccag    360

gtcaccgtct cctca                                                     375
```

<210> SEQ ID NO 49
<211> LENGTH: 357
<212> TYPE: DNA
<213> ORGANISM: Artificial Sequence
<220> FEATURE:
<223> OTHER INFORMATION: Nucleic acid sequence of CD70-sdAb-1F

<400> SEQUENCE: 49
gaggtgcagg tggtggagtc gggggaggga atggtgcagg ctgggggatc tctgaggctc 60
tcctgtgcag cctctggaaa gcgcttcagt ttctatttta tgggatggta ccgccaggct 120
ccaggaaagc agcgcgagtt ggtcgccctt attactggtg atggcaggac aaactatgca 180
gggtccgtgg agggccgatt caccatctcc agagacaacg ccaagaacac gctatatctg 240
caaatgaaca gcatgaaacc tgaggacaca gccgtctatt attgctatgc agatgcattc 300
gcgggggccg gccgcgatga gtactggggc caggggaccc aggtcagcgt ctcctca 357

<210> SEQ ID NO 50
<211> LENGTH: 354
<212> TYPE: DNA
<213> ORGANISM: Artificial Sequence
<220> FEATURE:
<223> OTHER INFORMATION: Nucleic acid sequence of CD70-sdAb-1G

<400> SEQUENCE: 50
cagttgcagc tcgtggagtc cgggggaggc ttggtgcaac ttgggggggtc tctgacgctc 60
tcctgtacag cctctgggat tatcttcaat agcgattacg tgggctggta ccgccaggct 120
ccagggtcgg atcgcgagtt ggtcgcactt actagtaata tgaggacaaa ctatgcagac 180
tccgtggagg gccgattcac catctccaga gacaacgcca agaatacggt gtatctgcaa 240
atgaacagcc tgaaacctga ggacacggcc gtctattatt gtaatgtaaa tagaatgacc 300
tcctatgggc ctcgggacta ctggggccag ggaccccagg tcaccgtctc ctcc 354

<210> SEQ ID NO 51
<211> LENGTH: 357
<212> TYPE: DNA
<213> ORGANISM: Artificial Sequence
<220> FEATURE:
<223> OTHER INFORMATION: Nucleic acid sequence of CD70-sdAb-1H

<400> SEQUENCE: 51
gaggtgcagc tggtggagtc tggtggagga atggtgcagg ctgggggatc tctgagactc 60
tcctgtgctg cctctggaaa gcccttcagt ttctatttca tgggatggta ccgccaggct 120
ccaggaaagc agcgcgagtt ggtcgccctt attaccggtg atggtatgac aaactatgca 180
gactccgtgg agggccgatt caccatctcc agagacaacg ccaagaacac aatgtatctg 240
caaatgaaca gcctgaaacc tgaggacaca gccgtctatt attgctatgc agatgtatgg 300
gcgggggccg gccgcgatga gtactggggc caggggaccc gggtcaccgt ctcctca 357

<210> SEQ ID NO 52
<211> LENGTH: 351
<212> TYPE: DNA
<213> ORGANISM: Artificial Sequence
<220> FEATURE:
<223> OTHER INFORMATION: Nucleic acid sequence of CD70-sdAb-3H

<400> SEQUENCE: 52
cagttgcagc tcgtggagtc gggtggaggc ttggtgcagc ctgggggggtc tctgagactc 60
tcctgtgcag cctctggaaa catcctcaga ttcaatgccg tgggctggta ccgccaggct 120
ccagggaagc agcgcgactt ggtcgcggct atggctggtg cacggacaaa ctatgcagac 180
tccgtggagg gccgattcac catctccgga aacaacgcca acaacacggt ttatctgcaa 240
atgaacagcc tgaaacctga agacacaggc gtctactact gtggtgctga ccgcgtatat 300
ggtccgccgt atgaatatgg gggccggggg acccaggtca ccgtcttgtc a 351

<210> SEQ ID NO 53
<211> LENGTH: 336
<212> TYPE: DNA
<213> ORGANISM: Artificial Sequence
<220> FEATURE:
<223> OTHER INFORMATION: Nucleic acid sequence of CD70-sdAb-5A

<400> SEQUENCE: 53
gaggtgcagc tggtggagtc ggggggaggc ttggtgcagg ctgggggtc tctgaggctc 60 tcctgtgcag cctctgaaag catcttcaat aattatgtca tggcctggta ccgccagcct 120
ccagggaagc agcgcgaggc ggtcgcacaa attagtactg atggtagtgc gtactatcag 180
gaccgagtga agggccgatt cactatctcc agagacaacg ccaagaactt ggtgaatctg 240
caaatgagca gcctgaaacc tgaggacaca gccgtctatt actgtactgc aggtctccag 300
tactggggcc aggggaccca ggtcaccgtc tcctca 336

<210> SEQ ID NO 54
<211> LENGTH: 378
<212> TYPE: DNA
<213> ORGANISM: Artificial Sequence
<220> FEATURE:
<223> OTHER INFORMATION: Nucleic acid sequence of CD70-sdAb-5B

<400> SEQUENCE: 54
caggtgcagc tcgtggagtc tggaggaggc ttggtgcagg ctgggggtc tctgagactc 60 tcctgtgcag cctctggatt cactttcgat gattatgcca taggctggtt ccgccaggcc 120
ccagggaagg agcctgaggg ggtctcatgt ttcaggagta gtgatggtaa catatactat 180
tcagactccg tgaggggccg attcaccatc tccagtgaca acgccaagaa cacggtgtat 240
ctgcaaatga acagactgaa acctgaggac acggccgttt actactgtgc agcctatagc 300
gtactgctca ggccctgggt gttatgtgaa ggctcatatg actactgggg ccaggggacc 360
caggtcaccg tctcctca 378

<210> SEQ ID NO 55
<211> LENGTH: 357
<212> TYPE: DNA
<213> ORGANISM: Artificial Sequence
<220> FEATURE:
<223> OTHER INFORMATION: Nucleic acid sequence of CD70-sdAb-5H

<400> SEQUENCE: 55
gaggtgcagc tggtggagtc aggggggaggt atggtgcagg ctgggggatc tctgagactc 60
tcctgtgcag cccctggaaa gatcttcagt ttctatttca tgggatggta ccgccaggct 120
ccaggaaagc agcgcgagtt ggtcgccctt attaccggtg atggtaggac aaactatgca 180
gactccgtgg agggccgatt caccatctcc agagacaacg ccaagaacac ggtgtatctg 240
caaatgaaca gcctgaaacc tgaggacaca gccgtctatt attgctatgc agatgtattt 300
gcgagggccg gccgcgatga gtactggggc caggggaccc aggtcagcgt ctcctca 357

<210> SEQ ID NO 56
<211> LENGTH: 375
<212> TYPE: DNA
<213> ORGANISM: Artificial Sequence
<220> FEATURE:
<223> OTHER INFORMATION: Nucleic acid sequence of CD70-sdAb-7D

<400> SEQUENCE: 56

```
gaggtgcagc tggtggagtc tgggggaggc ttggtgcagg ctgggggggtc tctgagactc     60

tcctgtgcag cctctggatt cactttcgat gattatgcca taggctggtt ccgccaggcc    120

ccagggaagg agcaagaggg ggtctcatgt attagacgta gtgatggtag cacatggtat    180

gcaaactccg tgaagggccg attcaccatc tccaatgaca acgccaagaa cacggtgtat    240

ctgcaaatga acagcctgaa acctgaggac acggccgttt attactgcgc agtagatcgt    300

tacggtcaga gttggcacga gggccgcggc gctttggacg catggggcca ggggaccctg    360

gtcactgtct cctca                                                      375
```

```
<210> SEQ ID NO 57
<211> LENGTH: 357
<212> TYPE: DNA
<213> ORGANISM: Artificial Sequence
<220> FEATURE:
<223> OTHER INFORMATION: Nucleic acid sequence of CD70-sdAb-H3

<400> SEQUENCE: 57

caggtgcagc tcgtggagtc tgggggagga atggtgcagg ctgggcgatc tctgagactc     60

tcctgtgctg cctctggaaa gcccttcagt ttctatttca tgggatggta tcgccaggct    120

ccaggaaagg agcgcgagtt ggtcgccctt attaccggtg atggtatgac aaactatgca    180

gactccgtgg agggccgatt caccatctcc agagacaacg ccaagaatac attgtatctc    240

gaaatgaaca gcctgaaacc tgaggacaca gccgtctatt attgctatgc agatgcttgg    300

gcgggggccg ttcgcgccga gtactggggc caggggaccc aggtcagcgt ctcctca       357
```

```
<210> SEQ ID NO 58
<211> LENGTH: 375
<212> TYPE: DNA
<213> ORGANISM: Artificial Sequence
<220> FEATURE:
<223> OTHER INFORMATION: Nucleic acid sequence of CD70-sdAb-L2

<400> SEQUENCE: 58

gaggtgcagc tggtggagtc cgggggaggc ttggtgcagg ctgggggggtc tctgagactc     60

tcctgtgcag cctctggatt cactgtcgat gattatgtca taggctggtt ccgccaggcc    120

ccagggaagg agcatgaggg ggtctcatgt attagtagta atgatggtag tacatggtat    180

gcagactccg tgaagggccg attcaccatc tccagtgaca acgccaagaa cacgatgtat    240

ctgcaaatga acagcctgaa acctgaggac acggccgttt attactgtgc agctaaatac    300

gcaccctacg ggttggagta ctgggaggga ggcatggact actggggcaa agggaccctg    360

gtcaccgtct cctca                                                      375
```

```
<210> SEQ ID NO 59
<211> LENGTH: 372
<212> TYPE: DNA
<213> ORGANISM: Artificial Sequence
<220> FEATURE:
<223> OTHER INFORMATION: Nucleic acid sequence of CD70-sdAb-L1

<400> SEQUENCE: 59

gaggtgcagg tggtggagtc tgggggagga ttggtgcagg ctgggggctc tctgagactc     60

tcctgtgcag cctctggacg caccttcagt tcatatgcca tgggctgggt ccgccaggct    120

ccagggaagg accaagagtt tgtagcggct attaactgga gtgatggtag cacatactat    180

gcagactccg tgaagggccg attcaccatc gccagagaca acgccaagaa cacggcgttt    240
```

-continued

```
ctgcaaatga acagcctgaa acctgaggac acggccgtgt attactgtgc agcagggtgt    300

tgcggagtag ctgatgcccc cctcaatgct ttggacgcat ggggccaggg gaccctggtc    360

actgtctcct ca                                                        372


<210> SEQ ID NO 60
<211> LENGTH: 363
<212> TYPE: PRT
<213> ORGANISM: Artificial Sequence
<220> FEATURE:
<223> OTHER INFORMATION: CD70-CAR-1C

<400> SEQUENCE: 60

Met Ala Leu Pro Val Thr Ala Leu Leu Leu Pro Leu Ala Leu Leu Leu
1               5                   10                  15

His Ala Ala Arg Pro Glu Val Gln Val Val Glu Ser Gly Gly Gly Met
            20                  25                  30

Val Gln Ala Gly Arg Ser Leu Arg Leu Ser Cys Ala Ala Ser Gly Lys
        35                  40                  45

Pro Phe Ser Phe Tyr Phe Met Gly Trp Tyr Arg Gln Ala Pro Gly Asn
    50                  55                  60

Gln Arg Glu Leu Val Ala Leu Ile Thr Gly Asp Gly Met Thr Asn Tyr
65                  70                  75                  80

Ala Asp Ser Val Glu Gly Arg Phe Thr Ile Ser Arg Asp Asn Ala Lys
                85                  90                  95

Asn Thr Met Tyr Leu Glu Met Asn Ser Leu Lys Pro Glu Asp Thr Ala
            100                 105                 110

Val Tyr Tyr Cys Tyr Ala Asp Ala Trp Ala Gly Ala Gly Arg Glu Glu
        115                 120                 125

Tyr Trp Gly Gln Gly Thr Gln Val Ser Val Ser Ser Thr Thr Thr Pro
    130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp Ile Tyr Ile Trp Ala Pro Leu
            180                 185                 190

Ala Gly Thr Cys Gly Val Leu Leu Leu Ser Leu Val Ile Thr Leu Tyr
        195                 200                 205

Cys Lys Arg Gly Arg Lys Lys Leu Leu Tyr Ile Phe Lys Gln Pro Phe
    210                 215                 220

Met Arg Pro Val Gln Thr Thr Gln Glu Glu Asp Gly Cys Ser Cys Arg
225                 230                 235                 240

Phe Pro Glu Glu Glu Glu Gly Gly Cys Glu Leu Arg Val Lys Phe Ser
                245                 250                 255

Arg Ser Ala Asp Ala Pro Ala Tyr Lys Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
    290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
                325                 330                 335
```

```
His Asp Gly Leu Tyr Gln Gly Leu Ser Thr Ala Thr Lys Asp Thr Tyr
            340                 345                 350

Asp Ala Leu His Met Gln Ala Leu Pro Pro Arg
        355                 360


<210> SEQ ID NO 61
<211> LENGTH: 369
<212> TYPE: PRT
<213> ORGANISM: Artificial Sequence
<220> FEATURE:
<223> OTHER INFORMATION: CD70-CAR-1E

<400> SEQUENCE: 61

Met Ala Leu Pro Val Thr Ala Leu Leu Leu Pro Leu Ala Leu Leu Leu
1               5                   10                  15

His Ala Ala Arg Pro Glu Val Gln Val Val Glu Ser Gly Gly Gly Leu
            20                  25                  30

Val Gln Ala Gly Gly Ser Leu Arg Leu Ser Cys Ala Ala Ser Gly Phe
        35                  40                  45

Ala Phe Asp Asp Tyr Ala Ile Gly Trp Phe Arg Gln Ala Pro Gly Lys
    50                  55                  60

Glu Gln Glu Arg Val Ser Cys Met Ser Ser Ser Asp Gly Ser Thr Tyr
65                  70                  75                  80

Tyr Ala Asp Ser Val Lys Gly Arg Phe Thr Ile Ser Ser Asp Asn Ala
                85                  90                  95

Lys Asn Thr Val Tyr Leu Gln Met Asn Ser Leu Lys Pro Glu Asp Thr
            100                 105                 110

Ala Val Tyr Tyr Cys Ala Ala Gly Val Asn Tyr Tyr Arg Glu Asp Gly
        115                 120                 125

Cys Pro Gly Ala Leu Asp Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335
```

```
Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg


<210> SEQ ID NO 62
<211> LENGTH: 363
<212> TYPE: PRT
<213> ORGANISM: Artificial Sequence
<220> FEATURE:
<223> OTHER INFORMATION: CD70-CAR-1F

<400> SEQUENCE: 62

Met Ala Leu Pro Val Thr Ala Leu Leu Leu Pro Leu Ala Leu Leu Leu
1               5                   10                  15

His Ala Ala Arg Pro Glu Val Gln Val Val Glu Ser Gly Gly Gly Met
            20                  25                  30

Val Gln Ala Gly Gly Ser Leu Arg Leu Ser Cys Ala Ala Ser Gly Lys
        35                  40                  45

Arg Phe Ser Phe Tyr Phe Met Gly Trp Tyr Arg Gln Ala Pro Gly Lys
    50                  55                  60

Gln Arg Glu Leu Val Ala Leu Ile Thr Gly Asp Gly Arg Thr Asn Tyr
65                  70                  75                  80

Ala Gly Ser Val Glu Gly Arg Phe Thr Ile Ser Arg Asp Asn Ala Lys
                85                  90                  95

Asn Thr Leu Tyr Leu Gln Met Asn Ser Met Lys Pro Glu Asp Thr Ala
            100                 105                 110

Val Tyr Tyr Cys Tyr Ala Asp Ala Phe Ala Gly Ala Gly Arg Asp Glu
        115                 120                 125

Tyr Trp Gly Gln Gly Thr Gln Val Ser Val Ser Ser Thr Thr Thr Pro
    130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp Ile Tyr Ile Trp Ala Pro Leu
            180                 185                 190

Ala Gly Thr Cys Gly Val Leu Leu Leu Ser Leu Val Ile Thr Leu Tyr
        195                 200                 205

Cys Lys Arg Gly Arg Lys Lys Leu Leu Tyr Ile Phe Lys Gln Pro Phe
    210                 215                 220

Met Arg Pro Val Gln Thr Thr Gln Glu Glu Asp Gly Cys Ser Cys Arg
225                 230                 235                 240

Phe Pro Glu Glu Glu Glu Gly Gly Cys Glu Leu Arg Val Lys Phe Ser
                245                 250                 255

Arg Ser Ala Asp Ala Pro Ala Tyr Lys Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
    290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
```

```
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
        355                 360


<210> SEQ ID NO 63
<211> LENGTH: 362
<212> TYPE: PRT
<213> ORGANISM: Artificial Sequence
<220> FEATURE:
<223> OTHER INFORMATION: CD70-CAR-1G

<400> SEQUENCE: 63

Met Ala Leu Pro Val Thr Ala Leu Leu Leu Pro Leu Ala Leu Leu Leu
1               5                   10                  15

His Ala Ala Arg Pro Gln Leu Gln Leu Val Glu Ser Gly Gly Gly Leu
            20                  25                  30

Val Gln Leu Gly Gly Ser Leu Thr Leu Ser Cys Thr Ala Ser Gly Ile
        35                  40                  45

Ile Phe Asn Ser Asp Tyr Val Gly Trp Tyr Arg Gln Ala Pro Gly Ser
    50                  55                  60

Asp Arg Glu Leu Val Ala Leu Thr Ser Asn Met Arg Thr Asn Tyr Ala
65                  70                  75                  80

Asp Ser Val Glu Gly Arg Phe Thr Ile Ser Arg Asp Asn Ala Lys Asn
                85                  90                  95

Thr Val Tyr Leu Gln Met Asn Ser Leu Lys Pro Glu Asp Thr Ala Val
            100                 105                 110

Tyr Tyr Cys Asn Val Asn Arg Met Thr Ser Tyr Gly Pro Arg Asp Tyr
        115                 120                 125

Trp Gly Gln Gly Thr Gln Val Thr Val Ser Ser Thr Thr Thr Pro Ala
    130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
        195                 200                 205

Lys Arg Gly Arg Lys Lys Leu Leu Tyr Ile Phe Lys Gln Pro Phe Met
    210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Lys Gln Gly Gln Asn Gln Leu Tyr Asn
            260                 265                 270

Glu Leu Asn Leu Gly Arg Arg Glu Glu Tyr Asp Val Leu Asp Lys Arg
        275                 280                 285

Arg Gly Arg Asp Pro Glu Met Gly Gly Lys Pro Arg Arg Lys Asn Pro
    290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
```

```
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
        355                 360


<210> SEQ ID NO 64
<211> LENGTH: 363
<212> TYPE: PRT
<213> ORGANISM: Artificial Sequence
<220> FEATURE:
<223> OTHER INFORMATION: CD70-CAR-1H

<400> SEQUENCE: 64

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Gly Ser Leu Arg Leu Ser Cys Ala Ala Ser Gly Lys
        35                  40                  45

Pro Phe Ser Phe Tyr Phe Met Gly Trp Tyr Arg Gln Ala Pro Gly Lys
    50                  55                  60

Gln Arg Glu Leu Val Ala Leu Ile Thr Gly Asp Gly Met Thr Asn Tyr
65                  70                  75                  80

Ala Asp Ser Val Glu Gly Arg Phe Thr Ile Ser Arg Asp Asn Ala Lys
                85                  90                  95

Asn Thr Met Tyr Leu Gln Met Asn Ser Leu Lys Pro Glu Asp Thr Ala
            100                 105                 110

Val Tyr Tyr Cys Tyr Ala Asp Val Trp Ala Gly Ala Gly Arg Asp Glu
        115                 120                 125

Tyr Trp Gly Gln Gly Thr Arg Val Thr Val Ser Ser Thr Thr Thr Pro
    130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp Ile Tyr Ile Trp Ala Pro Leu
            180                 185                 190

Ala Gly Thr Cys Gly Val Leu Leu Leu Ser Leu Val Ile Thr Leu Tyr
        195                 200                 205

Cys Lys Arg Gly Arg Lys Lys Leu Leu Tyr Ile Phe Lys Gln Pro Phe
    210                 215                 220

Met Arg Pro Val Gln Thr Thr Gln Glu Glu Asp Gly Cys Ser Cys Arg
225                 230                 235                 240

Phe Pro Glu Glu Glu Glu Gly Gly Cys Glu Leu Arg Val Lys Phe Ser
                245                 250                 255

Arg Ser Ala Asp Ala Pro Ala Tyr Lys Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
    290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
```

```
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
        355                 360


<210> SEQ ID NO 65
<211> LENGTH: 361
<212> TYPE: PRT
<213> ORGANISM: Artificial Sequence
<220> FEATURE:
<223> OTHER INFORMATION: CD70-CAR-3H

<400> SEQUENCE: 65

Met Ala Leu Pro Val Thr Ala Leu Leu Leu Pro Leu Ala Leu Leu Leu
1               5                   10                  15

His Ala Ala Arg Pro Gln Leu Gln Leu Val Glu Ser Gly Gly Gly Leu
            20                  25                  30

Val Gln Pro Gly Gly Ser Leu Arg Leu Ser Cys Ala Ala Ser Gly Asn
        35                  40                  45

Ile Leu Arg Phe Asn Ala Val Gly Trp Tyr Arg Gln Ala Pro Gly Lys
    50                  55                  60

Gln Arg Asp Leu Val Ala Ala Met Ala Gly Ala Arg Thr Asn Tyr Ala
65                  70                  75                  80

Asp Ser Val Glu Gly Arg Phe Thr Ile Ser Gly Asn Asn Ala Asn Asn
                85                  90                  95

Thr Val Tyr Leu Gln Met Asn Ser Leu Lys Pro Glu Asp Thr Gly Val
            100                 105                 110

Tyr Tyr Cys Gly Ala Asp Arg Val Tyr Gly Pro Pro Tyr Glu Tyr Gly
        115                 120                 125

Gly Arg Gly Thr Gln Val Thr Val Leu Ser Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Lys Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
```

```
            325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg
        355                 360
```

<210> SEQ ID NO 66
<211> LENGTH: 356
<212> TYPE: PRT
<213> ORGANISM: Artificial Sequence
<220> FEATURE:
<223> OTHER INFORMATION: CD70-CAR-5A

<400> SEQUENCE: 66

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Glu Ser
        35                  40                  45

Ile Phe Asn Asn Tyr Val Met Ala Trp Tyr Arg Gln Pro Pro Gly Lys
    50                  55                  60

Gln Arg Glu Ala Val Ala Gln Ile Ser Thr Asp Gly Ser Ala Tyr Tyr
65                  70                  75                  80

Gln Asp Arg Val Lys Gly Arg Phe Thr Ile Ser Arg Asp Asn Ala Lys
                85                  90                  95

Asn Leu Val Asn Leu Gln Met Ser Ser Leu Lys Pro Glu Asp Thr Ala
            100                 105                 110

Val Tyr Tyr Cys Thr Ala Gly Leu Gln Tyr Trp Gly Gln Gly Thr Gln
        115                 120                 125

Val Thr Val Ser Ser Thr Thr Thr Pro Ala Pro Arg Pro Pro Thr Pro
    130                 135                 140

Ala Pro Thr Ile Ala Ser Gln Pro Leu Ser Leu Arg Pro Glu Ala Cys
145                 150                 155                 160

Arg Pro Ala Ala Gly Gly Ala Val His Thr Arg Gly Leu Asp Phe Ala
                165                 170                 175

Cys Asp Ile Tyr Ile Trp Ala Pro Leu Ala Gly Thr Cys Gly Val Leu
            180                 185                 190

Leu Leu Ser Leu Val Ile Thr Leu Tyr Cys Lys Arg Gly Arg Lys Lys
        195                 200                 205

Leu Leu Tyr Ile Phe Lys Gln Pro Phe Met Arg Pro Val Gln Thr Thr
    210                 215                 220

Gln Glu Glu Asp Gly Cys Ser Cys Arg Phe Pro Glu Glu Glu Glu Gly
225                 230                 235                 240

Gly Cys Glu Leu Arg Val Lys Phe Ser Arg Ser Ala Asp Ala Pro Ala
                245                 250                 255

Tyr Lys Gln Gly Gln Asn Gln Leu Tyr Asn Glu Leu Asn Leu Gly Arg
            260                 265                 270

Arg Glu Glu Tyr Asp Val Leu Asp Lys Arg Arg Gly Arg Asp Pro Glu
        275                 280                 285

Met Gly Gly Lys Pro Arg Arg Lys Asn Pro Gln Glu Gly Leu Tyr Asn
    290                 295                 300

Glu Leu Gln Lys Asp Lys Met Ala Glu Ala Tyr Ser Glu Ile Gly Met
305                 310                 315                 320

Lys Gly Glu Arg Arg Arg Gly Lys Gly His Asp Gly Leu Tyr Gln Gly
```

```
            325                 330                 335

Leu Ser Thr Ala Thr Lys Asp Thr Tyr Asp Ala Leu His Met Gln Ala
            340                 345                 350

Leu Pro Pro Arg
        355


<210> SEQ ID NO 67
<211> LENGTH: 370
<212> TYPE: PRT
<213> ORGANISM: Artificial Sequence
<220> FEATURE:
<223> OTHER INFORMATION: CD70-CAR-5B

<400> SEQUENCE: 67

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Phe
        35                  40                  45

Thr Phe Asp Asp Tyr Ala Ile Gly Trp Phe Arg Gln Ala Pro Gly Lys
    50                  55                  60

Glu Pro Glu Gly Val Ser Cys Phe Arg Ser Ser Asp Gly Asn Ile Tyr
65                  70                  75                  80

Tyr Ser Asp Ser Val Arg Gly Arg Phe Thr Ile Ser Ser Asp Asn Ala
                85                  90                  95

Lys Asn Thr Val Tyr Leu Gln Met Asn Arg Leu Lys Pro Glu Asp Thr
            100                 105                 110

Ala Val Tyr Tyr Cys Ala Ala Tyr Ser Val Leu Leu Arg Pro Trp Val
        115                 120                 125

Leu Cys Glu Gly Ser Tyr Asp Tyr Trp Gly Gln Gly Thr Gln Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
```

```
            325                 330                 335

Glu Arg Arg Arg Gly Lys Gly His Asp Gly Leu Tyr Gln Gly Leu Ser
        340                 345                 350

Thr Ala Thr Lys Asp Thr Tyr Asp Ala Leu His Met Gln Ala Leu Pro
    355                 360                 365

Pro Arg
    370


<210> SEQ ID NO 68
<211> LENGTH: 363
<212> TYPE: PRT
<213> ORGANISM: Artificial Sequence
<220> FEATURE:
<223> OTHER INFORMATION: CD70-CAR-5H

<400> SEQUENCE: 68

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Gly Ser Leu Arg Leu Ser Cys Ala Ala Pro Gly Lys
        35                  40                  45

Ile Phe Ser Phe Tyr Phe Met Gly Trp Tyr Arg Gln Ala Pro Gly Lys
    50                  55                  60

Gln Arg Glu Leu Val Ala Leu Ile Thr Gly Asp Gly Arg Thr Asn Tyr
65                  70                  75                  80

Ala Asp Ser Val Glu Gly Arg Phe Thr Ile Ser Arg Asp Asn Ala Lys
                85                  90                  95

Asn Thr Val Tyr Leu Gln Met Asn Ser Leu Lys Pro Glu Asp Thr Ala
            100                 105                 110

Val Tyr Tyr Cys Tyr Ala Asp Val Phe Ala Arg Ala Gly Arg Asp Glu
        115                 120                 125

Tyr Trp Gly Gln Gly Thr Gln Val Ser Val Ser Ser Thr Thr Thr Pro
    130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp Ile Tyr Ile Trp Ala Pro Leu
            180                 185                 190

Ala Gly Thr Cys Gly Val Leu Leu Leu Ser Leu Val Ile Thr Leu Tyr
        195                 200                 205

Cys Lys Arg Gly Arg Lys Lys Leu Leu Tyr Ile Phe Lys Gln Pro Phe
    210                 215                 220

Met Arg Pro Val Gln Thr Thr Gln Glu Glu Asp Gly Cys Ser Cys Arg
225                 230                 235                 240

Phe Pro Glu Glu Glu Glu Gly Gly Cys Glu Leu Arg Val Lys Phe Ser
                245                 250                 255

Arg Ser Ala Asp Ala Pro Ala Tyr Lys Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
    290                 295                 300

Pro Gln Glu Gly Leu Tyr Asn Glu Leu Gln Lys Asp Lys Met Ala Glu
```

305 310 315 320

Ala Tyr Ser Glu Ile Gly Met Lys Gly Glu Arg Arg Arg Gly Lys Gly
325 330 335

His Asp Gly Leu Tyr Gln Gly Leu Ser Thr Ala Thr Lys Asp Thr Tyr
340 345 350

Asp Ala Leu His Met Gln Ala Leu Pro Pro Arg
355 360

<210> SEQ ID NO 69
<211> LENGTH: 369
<212> TYPE: PRT
<213> ORGANISM: Artificial Sequence
<220> FEATURE:
<223> OTHER INFORMATION: CD70-CAR-7D

<400> SEQUENCE: 69

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Ala Gly Gly Ser Leu Arg Leu Ser Cys Ala Ala Ser Gly Phe
35 40 45

Thr Phe Asp Asp Tyr Ala Ile Gly Trp Phe Arg Gln Ala Pro Gly Lys
50 55 60

Glu Gln Glu Gly Val Ser Cys Ile Arg Arg Ser Asp Gly Ser Thr Trp
65 70 75 80

Tyr Ala Asn Ser Val Lys Gly Arg Phe Thr Ile Ser Asn Asp Asn Ala
85 90 95

Lys Asn Thr Val Tyr Leu Gln Met Asn Ser Leu Lys Pro Glu Asp Thr
100 105 110

Ala Val Tyr Tyr Cys Ala Val Asp Arg Tyr Gly Gln Ser Trp His Glu
115 120 125

Gly Arg Gly Ala Leu Asp Ala Trp Gly Gln Gly Thr Leu Val Thr Val
130 135 140

Ser Ser Thr Thr Thr Pro Ala Pro Arg Pro Pro Thr Pro Ala Pro Thr
145 150 155 160

Ile Ala Ser Gln Pro Leu Ser Leu Arg Pro Glu Ala Cys Arg Pro Ala
165 170 175

Ala Gly Gly Ala Val His Thr Arg Gly Leu Asp Phe Ala Cys Asp Ile
180 185 190

Tyr Ile Trp Ala Pro Leu Ala Gly Thr Cys Gly Val Leu Leu Leu Ser
195 200 205

Leu Val Ile Thr Leu Tyr Cys Lys Arg Gly Arg Lys Lys Leu Leu Tyr
210 215 220

Ile Phe Lys Gln Pro Phe Met Arg Pro Val Gln Thr Thr Gln Glu Glu
225 230 235 240

Asp Gly Cys Ser Cys Arg Phe Pro Glu Glu Glu Glu Gly Gly Cys Glu
245 250 255

Leu Arg Val Lys Phe Ser Arg Ser Ala Asp Ala Pro Ala Tyr Lys Gln
260 265 270

Gly Gln Asn Gln Leu Tyr Asn Glu Leu Asn Leu Gly Arg Arg Glu Glu
275 280 285

Tyr Asp Val Leu Asp Lys Arg Arg Gly Arg Asp Pro Glu Met Gly Gly
290 295 300

Lys Pro Arg Arg Lys Asn Pro Gln Glu Gly Leu Tyr Asn Glu Leu Gln

```
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg


<210> SEQ ID NO 70
<211> LENGTH: 363
<212> TYPE: PRT
<213> ORGANISM: Artificial Sequence
<220> FEATURE:
<223> OTHER INFORMATION: CD70-CAR-H3

<400> SEQUENCE: 70

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Met
            20                  25                  30

Val Gln Ala Gly Arg Ser Leu Arg Leu Ser Cys Ala Ala Ser Gly Lys
        35                  40                  45

Pro Phe Ser Phe Tyr Phe Met Gly Trp Tyr Arg Gln Ala Pro Gly Lys
    50                  55                  60

Glu Arg Glu Leu Val Ala Leu Ile Thr Gly Asp Gly Met Thr Asn Tyr
65                  70                  75                  80

Ala Asp Ser Val Glu Gly Arg Phe Thr Ile Ser Arg Asp Asn Ala Lys
                85                  90                  95

Asn Thr Leu Tyr Leu Glu Met Asn Ser Leu Lys Pro Glu Asp Thr Ala
            100                 105                 110

Val Tyr Tyr Cys Tyr Ala Asp Ala Trp Ala Gly Ala Val Arg Ala Glu
        115                 120                 125

Tyr Trp Gly Gln Gly Thr Gln Val Ser Val Ser Ser Thr Thr Thr Pro
    130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp Ile Tyr Ile Trp Ala Pro Leu
            180                 185                 190

Ala Gly Thr Cys Gly Val Leu Leu Leu Ser Leu Val Ile Thr Leu Tyr
        195                 200                 205

Cys Lys Arg Gly Arg Lys Lys Leu Leu Tyr Ile Phe Lys Gln Pro Phe
    210                 215                 220

Met Arg Pro Val Gln Thr Thr Gln Glu Glu Asp Gly Cys Ser Cys Arg
225                 230                 235                 240

Phe Pro Glu Glu Glu Glu Gly Gly Cys Glu Leu Arg Val Lys Phe Ser
                245                 250                 255

Arg Ser Ala Asp Ala Pro Ala Tyr Lys Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
    290                 295                 300
```

```
Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
        355                 360


<210> SEQ ID NO 71
<211> LENGTH: 369
<212> TYPE: PRT
<213> ORGANISM: Artificial Sequence
<220> FEATURE:
<223> OTHER INFORMATION: CD70-CAR-L2

<400> SEQUENCE: 71

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Phe
        35                  40                  45

Thr Val Asp Asp Tyr Val Ile Gly Trp Phe Arg Gln Ala Pro Gly Lys
    50                  55                  60

Glu His Glu Gly Val Ser Cys Ile Ser Ser Asn Asp Gly Ser Thr Trp
65                  70                  75                  80

Tyr Ala Asp Ser Val Lys Gly Arg Phe Thr Ile Ser Ser Asp Asn Ala
                85                  90                  95

Lys Asn Thr Met Tyr Leu Gln Met Asn Ser Leu Lys Pro Glu Asp Thr
            100                 105                 110

Ala Val Tyr Tyr Cys Ala Ala Lys Tyr Ala Pro Tyr Gly Leu Glu Tyr
        115                 120                 125

Trp Glu Gly Gly Met Asp Tyr Trp Gly Lys Gly Thr Leu Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300
```

```
Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg


<210> SEQ ID NO 72
<211> LENGTH: 368
<212> TYPE: PRT
<213> ORGANISM: Artificial Sequence
<220> FEATURE:
<223> OTHER INFORMATION: CD70-CAR-L1

<400> SEQUENCE: 72

Met Ala Leu Pro Val Thr Ala Leu Leu Leu Pro Leu Ala Leu Leu Leu
1               5                   10                  15

His Ala Ala Arg Pro Glu Val Gln Val Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Ser Ser Tyr Ala Met Gly Trp Val Arg Gln Ala Pro Gly Lys
    50                  55                  60

Asp Gln Glu Phe Val Ala Ala Ile Asn Trp Ser Asp Gly Ser Thr Tyr
65                  70                  75                  80

Tyr Ala Asp Ser Val Lys Gly Arg Phe Thr Ile Ala Arg Asp Asn Ala
                85                  90                  95

Lys Asn Thr Ala Phe Leu Gln Met Asn Ser Leu Lys Pro Glu Asp Thr
            100                 105                 110

Ala Val Tyr Tyr Cys Ala Ala Gly Cys Cys Gly Val Ala Asp Ala Pro
        115                 120                 125

Leu Asn Ala Leu Asp Ala Trp Gly Gln Gly Thr Leu Val Thr Val Ser
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Lys Gln Gly
            260                 265                 270

Gln Asn Gln Leu Tyr Asn Glu Leu Asn Leu Gly Arg Arg Glu Glu Tyr
        275                 280                 285
```

```
Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365


<210> SEQ ID NO 73
<211> LENGTH: 1089
<212> TYPE: DNA
<213> ORGANISM: Artificial Sequence
<220> FEATURE:
<223> OTHER INFORMATION: Nucleic acid sequence of CD70-CAR-1C

<400> SEQUENCE: 73

atggccttac cagtgaccgc cttgctcctg ccgctggcct tgctgctcca cgccgccagg      60

ccggaggtgc aggtggtgga gtcgggggga ggaatggtgc aggctgggcg atctctgaga     120

ctctcctgtg ctgcctctgg aaagcccttc agtttctatt tcatgggatg gtatcgccag     180

gctccaggaa accagcgcga gttggtcgcc cttattaccg gtgatggtat gacaaactat     240

gcagactccg tggagggccg attcaccatc tccagagaca acgccaagaa tacaatgtat     300

ctcgaaatga acagcctgaa acctgaggac acagccgtct attattgcta tgcagatgct     360

tgggcggggg ccggccgcga agagtactgg ggccagggga cccaggtcag cgtctcctca     420

accacgacgc cagcgccgcg accaccaaca ccggcgccca ccatcgcgtc gcagcccctg     480

tccctgcgcc cagaggcgtg ccggccagcg gcggggggcg cagtgcacac gagggggctg     540

gacttcgcct gtgatatcta catctgggcg cccttggccg ggacttgtgg ggtccttctc     600

ctgtcactgg ttatcaccct ttactgcaaa cggggcagaa agaaactcct gtatatattc     660

aaacaaccat ttatgagacc agtacaaact actcaagagg aagatggctg tagctgccga     720

tttccagaag aagaagaagg aggatgtgaa ctgagagtga agttcagcag gagcgcagac     780

gcccccgcgt acaagcaggg ccagaaccag ctctataacg agctcaatct aggacgaaga     840

gaggagtacg atgttttgga caagagacgt ggccgggacc ctgagatggg gggaaagccg     900

agaaggaaga accctcagga aggcctgtac aatgaactgc agaaagataa gatggcggag     960

gcctacagtg agattgggat gaaaggcgag cgccggaggg gcaaggggca cgatggcctt    1020

taccagggtc tcagtacagc caccaaggac acctacgacg cccttcacat gcaggccctg    1080

ccccctcgc                                                            1089


<210> SEQ ID NO 74
<211> LENGTH: 1107
<212> TYPE: DNA
<213> ORGANISM: Artificial Sequence
<220> FEATURE:
<223> OTHER INFORMATION: Nucleic acid sequence of CD70-CAR-1E

<400> SEQUENCE: 74

atggccttac cagtgaccgc cttgctcctg ccgctggcct tgctgctcca cgccgccagg      60

ccggaggtgc aggtggtgga gtctggggga ggcttggtgc aggctggggg gtctctgaga     120

ctctcctgtg cagcctctgg attcgctttc gatgattatg ccataggctg gttccgccag     180
```

```
gccccaggga aggagcagga aagagtctca tgtatgagta gtagtgatgg tagcacatac    240

tatgcagact ccgtgaaggg ccgattcacc atctccagtg acaacgccaa gaacacggtg    300

tatctgcaaa tgaacagcct gaaacctgag gacacggccg tttattactg tgccgcaggg    360

gtcaattact atcgcgagga tgggtgcccg ggcgcgttgg actactgggg ccaggggacc    420

caggtcaccg tctcctcaac cacgacgcca gcgccgcgac caccaacacc ggcgcccacc    480

atcgcgtcgc agcccctgtc cctgcgccca gaggcgtgcc ggccagcggc ggggggcgca    540

gtgcacacga gggggctgga cttcgcctgt gatatctaca tctgggcgcc cttggccggg    600

acttgtgggg tccttctcct gtcactggtt atcacccttt actgcaaacg gggcagaaag    660

aaactcctgt atatattcaa acaaccattt atgagaccag tacaaactac tcaagaggaa    720

gatggctgta gctgccgatt tccagaagaa gaagaaggag gatgtgaact gagagtgaag    780

ttcagcagga gcgcagacgc ccccgcgtac aagcagggcc agaaccagct ctataacgag    840

ctcaatctag gacgaagaga ggagtacgat gttttggaca agagacgtgg ccgggaccct    900

gagatggggg gaaagccgag aaggaagaac cctcaggaag gcctgtacaa tgaactgcag    960

aaagataaga tggcggaggc ctacagtgag attgggatga aaggcgagcg ccggaggggc   1020

aaggggcacg atggccttta ccagggtctc agtacagcca ccaaggacac ctacgacgcc   1080

cttcacatgc aggccctgcc ccctcgc                                       1107
```

<210> SEQ ID NO 75
<211> LENGTH: 1089
<212> TYPE: DNA
<213> ORGANISM: Artificial Sequence
<220> FEATURE:
<223> OTHER INFORMATION: Nucleic acid sequence of CD70-CAR-1F

<400> SEQUENCE: 75

```
atggccttac cagtgaccgc cttgctcctg ccgctggcct tgctgctcca cgccgccagg     60

ccggaggtgc aggtggtgga gtcgggggga ggaatggtgc aggctggggg atctctgagg    120

ctctcctgtg cagcctctgg aaagcgcttc agtttctatt ttatgggatg gtaccgccag    180

gctccaggaa agcagcgcga gttggtcgcc cttattactg gtgatggcag gacaaactat    240

gcagggtccg tggagggccg attcaccatc tccagagaca acgccaagaa cacgctatat    300

ctgcaaatga acagcatgaa acctgaggac acagccgtct attattgcta tgcagatgca    360

ttcgcggggg ccggccgcga tgagtactgg ggccagggga cccaggtcag cgtctcctca    420

accacgacgc cagcgccgcg accaccaaca ccggcgccca ccatcgcgtc gcagcccctg    480

tccctgcgcc cagaggcgtg ccggccagcg gcggggggcg cagtgcacac gagggggctg    540

gacttcgcct gtgatatcta catctgggcg cccttggccg ggacttgtgg ggtccttctc    600

ctgtcactgg ttatcaccct ttactgcaaa cggggcagaa agaaactcct gtatatattc    660

aaacaaccat ttatgagacc agtacaaact actcaagagg aagatggctg tagctgccga    720

tttccagaag aagaagaagg aggatgtgaa ctgagagtga agttcagcag gagcgcagac    780

gcccccgcgt acaagcaggg ccagaaccag ctctataacg agctcaatct aggacgaaga    840

gaggagtacg atgttttgga caagagacgt ggccgggacc ctgagatggg gggaaagccg    900

agaaggaaga accctcagga aggcctgtac aatgaactgc agaaagataa gatggcggag    960

gcctacagtg agattgggat gaaaggcgag cgccggaggg gcaaggggca cgatggcctt   1020

taccagggtc tcagtacagc caccaaggac acctacgacg cccttcacat gcaggccctg   1080

ccccctcgc                                                            1089
```

<210> SEQ ID NO 76
<211> LENGTH: 1086
<212> TYPE: DNA
<213> ORGANISM: Artificial Sequence
<220> FEATURE:
<223> OTHER INFORMATION: Nucleic acid sequence of CD70-CAR-1G

<400> SEQUENCE: 76

```
atggccttac cagtgaccgc cttgctcctg ccgctggcct tgctgctcca cgccgccagg     60

ccgcagttgc agctcgtgga gtccggggga ggcttggtgc aacttggggg gtctctgacg    120

ctctcctgta cagcctctgg gattatcttc aatagcgatt acgtgggctg gtaccgccag    180

gctccagggt cggatcgcga gttggtcgca cttactagta atatgaggac aaactatgca    240

gactccgtgg agggccgatt caccatctcc agagacaacg ccaagaatac ggtgtatctg    300

caaatgaaca gcctgaaacc tgaggacacg gccgtctatt attgtaatgt aaatagaatg    360

acctcctatg ggcctcggga ctactggggc caggggaccc aggtcaccgt ctcctccacc    420

acgacgccag cgccgcgacc accaacaccg gcgcccacca tcgcgtcgca gcccctgtcc    480

ctgcgcccag aggcgtgccg gccagcggcg gggggcgcag tgcacacgag ggggctggac    540

ttcgcctgtg atatctacat ctgggcgccc ttggccggga cttgtggggt ccttctcctg    600

tcactggtta tcacccttta ctgcaaacgg ggcagaaaga aactcctgta tatattcaaa    660

caaccattta tgagaccagt acaaactact caagaggaag atggctgtag ctgccgattt    720

ccagaagaag aagaaggagg atgtgaactg agagtgaagt tcagcaggag cgcagacgcc    780

cccgcgtaca agcagggcca gaaccagctc tataacgagc tcaatctagg acgaagagag    840

gagtacgatg ttttggacaa gagacgtggc cgggaccctg agatgggggg aaagccgaga    900

aggaagaacc ctcaggaagg cctgtacaat gaactgcaga aagataagat ggcggaggcc    960

tacagtgaga ttgggatgaa aggcgagcgc cggaggggca aggggcacga tggcctttac   1020

cagggtctca gtacagccac caaggacacc tacgacgccc ttcacatgca ggccctgccc   1080

cctcgc                                                              1086
```

<210> SEQ ID NO 77
<211> LENGTH: 1089
<212> TYPE: DNA
<213> ORGANISM: Artificial Sequence
<220> FEATURE:
<223> OTHER INFORMATION: Nucleic acid sequence of CD70-CAR-1H

<400> SEQUENCE: 77

```
atggccttac cagtgaccgc cttgctcctg ccgctggcct tgctgctcca cgccgccagg     60

ccggaggtgc agctggtgga gtctggtgga ggaatggtgc aggctggggg atctctgaga    120

ctctcctgtg ctgcctctgg aaagcccttc agtttctatt tcatgggatg gtaccgccag    180

gctccaggaa agcagcgcga gttggtcgcc cttattaccg gtgatggtat gacaaactat    240

gcagactccg tggagggccg attcaccatc tccagagaca acgccaagaa cacaatgtat    300

ctgcaaatga acagcctgaa acctgaggac acagccgtct attattgcta tgcagatgta    360

tgggcggggg ccggccgcga tgagtactgg ggccagggga cccgggtcac cgtctcctca    420

accacgacgc cagcgccgcg accaccaaca ccggcgccca ccatcgcgtc gcagcccctg    480

tccctgcgcc cagaggcgtg ccggccagcg gcggggggcg cagtgcacac gagggggctg    540

gacttcgcct gtgatatcta catctgggcg cccttggccg ggacttgtgg ggtccttctc    600
```

```
ctgtcactgg ttatcaccct ttactgcaaa cggggcagaa agaaactcct gtatatattc    660

aaacaaccat ttatgagacc agtacaaact actcaagagg aagatggctg tagctgccga    720

tttccagaag aagaagaagg aggatgtgaa ctgagagtga agttcagcag gagcgcagac    780

gcccccgcgt acaagcaggg ccagaaccag ctctataacg agctcaatct aggacgaaga    840

gaggagtacg atgttttgga caagagacgt ggccgggacc ctgagatggg gggaaagccg    900

agaaggaaga accctcagga aggcctgtac aatgaactgc agaaagataa gatggcggag    960

gcctacagtg agattgggat gaaaggcgag cgccggaggg gcaaggggca cgatggcctt   1020

taccagggtc tcagtacagc caccaaggac acctacgacg cccttcacat gcaggccctg   1080

ccccctcgc                                                            1089
```

<210> SEQ ID NO 78
<211> LENGTH: 1083
<212> TYPE: DNA
<213> ORGANISM: Artificial Sequence
<220> FEATURE:
<223> OTHER INFORMATION: Nucleic acid sequence of CD70-CAR-3H

<400> SEQUENCE: 78

```
atggccttac cagtgaccgc cttgctcctg ccgctggcct tgctgctcca cgccgccagg     60

ccgcagttgc agctcgtgga gtcgggtgga ggcttggtgc agcctggggg gtctctgaga    120

ctctcctgtg cagcctctgg aaacatcctc agattcaatg ccgtgggctg gtaccgccag    180

gctccaggga agcagcgcga cttggtcgcg gctatggctg gtgcacggac aaactatgca    240

gactccgtgg agggccgatt caccatctcc ggaaacaacg ccaacaacac ggtttatctg    300

caaatgaaca gcctgaaacc tgaagacaca ggcgtctact actgtggtgc tgaccgcgta    360

tatggtccgc cgtatgaata tgggggccgg gggacccagg tcaccgtctt gtcaaccacg    420

acgccagcgc cgcgaccacc aacaccggcg cccaccatcg cgtcgcagcc cctgtccctg    480

cgcccagagg cgtgccggcc agcggcgggg ggcgcagtgc acacgagggg gctggacttc    540

gcctgtgata tctacatctg ggcgcccttg gccgggactt gtggggtcct tctcctgtca    600

ctggttatca ccctttactg caaacggggc agaaagaaac tcctgtatat attcaaacaa    660

ccatttatga gaccagtaca aactactcaa gaggaagatg gctgtagctg ccgatttcca    720

gaagaagaag aaggaggatg tgaactgaga gtgaagttca gcaggagcgc agacgccccc    780

gcgtacaagc agggccagaa ccagctctat aacgagctca atctaggacg aagagaggag    840

tacgatgttt tggacaagag acgtggccgg gaccctgaga tggggggaaa gccgagaagg    900

aagaaccctc aggaaggcct gtacaatgaa ctgcagaaag ataagatggc ggaggcctac    960

agtgagattg ggatgaaagg cgagcgccgg aggggcaagg ggcacgatgg cctttaccag   1020

ggtctcagta cagccaccaa ggacacctac gacgcccttc acatgcaggc cctgccccct   1080

cgc                                                                  1083
```

<210> SEQ ID NO 79
<211> LENGTH: 1068
<212> TYPE: DNA
<213> ORGANISM: Artificial Sequence
<220> FEATURE:
<223> OTHER INFORMATION: Nucleic acid sequence of CD70-CAR-5A

<400> SEQUENCE: 79

```
atggccttac cagtgaccgc cttgctcctg ccgctggcct tgctgctcca cgccgccagg     60

ccggaggtgc agctggtgga gtcgggggga ggcttggtgc aggctggggg gtctctgagg    120
```

```
ctctcctgtg cagcctctga aagcatcttc aataattatg tcatggcctg gtaccgccag    180
cctccaggga agcagcgcga ggcggtcgca caaattagta ctgatggtag tgcgtactat    240
caggaccgag tgaagggccg attcactatc tccagagaca acgccaagaa cttggtgaat    300
ctgcaaatga gcagcctgaa acctgaggac acagccgtct attactgtac tgcaggtctc    360
cagtactggg gccaggggac ccaggtcacc gtctcctcaa ccacgacgcc agcgccgcga    420
ccaccaacac cggcgcccac catcgcgtcg cagcccctgt ccctgcgccc agaggcgtgc    480
cggccagcgg cggggggcgc agtgcacacg agggggctgg acttcgcctg tgatatctac    540
atctgggcgc ccttggccgg gacttgtggg gtccttctcc tgtcactggt tatcaccctt    600
tactgcaaac ggggcagaaa gaaactcctg tatatattca aacaaccatt tatgagacca    660
gtacaaacta ctcaagagga agatggctgt agctgccgat ttccagaaga agaagaagga    720
ggatgtgaac tgagagtgaa gttcagcagg agcgcagacg cccccgcgta caagcagggc    780
cagaaccagc tctataacga gctcaatcta ggacgaagag aggagtacga tgttttggac    840
aagagacgtg gccgggaccc tgagatgggg ggaaagccga gaaggaagaa ccctcaggaa    900
ggcctgtaca atgaactgca gaaagataag atggcggagg cctacagtga gattgggatg    960
aaaggcgagc gccggagggg caaggggcac gatggccttt accagggtct cagtacagcc   1020
accaaggaca cctacgacgc ccttcacatg caggccctgc cccctcgc                1068
```

<210> SEQ ID NO 80
<211> LENGTH: 1110
<212> TYPE: DNA
<213> ORGANISM: Artificial Sequence
<220> FEATURE:
<223> OTHER INFORMATION: Nucleic acid sequence of CD70-CAR-5B

<400> SEQUENCE: 80

```
atggccttac cagtgaccgc cttgctcctg ccgctggcct tgctgctcca cgccgccagg     60
ccgcaggtgc agctcgtgga gtctggagga ggcttggtgc aggctggggg gtctctgaga    120
ctctcctgtg cagcctctgg attcactttc gatgattatg ccataggctg gttccgccag    180
gccccaggga aggagcctga gggggtctca tgtttcagga gtagtgatgg taacatatac    240
tattcagact ccgtgagggg ccgattcacc atctccagtg acaacgccaa gaacacggtg    300
tatctgcaaa tgaacagact gaaacctgag gacacggccg tttactactg tgcagcctat    360
agcgtactgc tcaggccctg ggtgttatgt gaaggctcat atgactactg gggccagggg    420
acccaggtca ccgtctcctc aaccacgacg ccagcgccgc gaccaccaac accggcgccc    480
accatcgcgt cgcagcccct gtccctgcgc ccagaggcgt gccggccagc ggcggggggc    540
gcagtgcaca cgagggggct ggacttcgcc tgtgatatct acatctgggc gcccttggcc    600
gggacttgtg gggtccttct cctgtcactg gttatcaccc tttactgcaa acggggcaga    660
aagaaactcc tgtatatatt caaacaacca tttatgagac cagtacaaac tactcaagag    720
gaagatggct gtagctgccg atttccagaa gaagaagaag gaggatgtga actgagagtg    780
aagttcagca ggagcgcaga cgcccccgcg tacaagcagg gccagaacca gctctataac    840
gagctcaatc taggacgaag agaggagtac gatgttttgg acaagagacg tggccgggac    900
cctgagatgg ggggaaagcc gagaaggaag aaccctcagg aaggcctgta caatgaactg    960
cagaaagata agatggcgga ggcctacagt gagattggga tgaaaggcga gcgccggagg   1020
ggcaaggggc acgatggcct ttaccagggt ctcagtacag ccaccaagga cacctacgac   1080
```

gcccttcaca tgcaggccct gccccctcgc 1110

<210> SEQ ID NO 81
<211> LENGTH: 1089
<212> TYPE: DNA
<213> ORGANISM: Artificial Sequence
<220> FEATURE:
<223> OTHER INFORMATION: Nucleic acid sequence of CD70-CAR-5H

<400> SEQUENCE: 81

```
atggccttac cagtgaccgc cttgctcctg ccgctggcct tgctgctcca cgccgccagg     60
ccggaggtgc agctggtgga gtcaggggga ggtatggtgc aggctggggg atctctgaga    120
ctctcctgtg cagcccctgg aaagatcttc agtttctatt tcatgggatg gtaccgccag    180
gctccaggaa agcagcgcga gttggtcgcc cttattaccg gtgatggtag gacaaactat    240
gcagactccg tggagggccg attcaccatc tccagagaca acgccaagaa cacggtgtat    300
ctgcaaatga acagcctgaa acctgaggac acagccgtct attattgcta tgcagatgta    360
tttgcgaggg ccggccgcga tgagtactgg ggccagggga cccaggtcag cgtctcctca    420
accacgacgc cagcgccgcg accaccaaca ccggcgccca ccatcgcgtc gcagcccctg    480
tccctgcgcc cagaggcgtg ccggccagcg gcggggggcg cagtgcacac gagggggctg    540
gacttcgcct gtgatatcta catctgggcg cccttggccg ggacttgtgg ggtccttctc    600
ctgtcactgg ttatcaccct ttactgcaaa cggggcagaa agaaactcct gtatatattc    660
aaacaaccat ttatgagacc agtacaaact actcaagagg aagatggctg tagctgccga    720
tttccagaag aagaagaagg aggatgtgaa ctgagagtga agttcagcag gagcgcagac    780
gcccccgcgt acaagcaggg ccagaaccag ctctataacg agctcaatct aggacgaaga    840
gaggagtacg atgttttgga caagagacgt ggccgggacc ctgagatggg gggaaagccg    900
agaaggaaga accctcagga aggcctgtac aatgaactgc agaaagataa gatggcggag    960
gcctacagtg agattgggat gaaaggcgag cgccggaggg gcaaggggca cgatggcctt   1020
taccagggtc tcagtacagc caccaaggac acctacgacg cccttcacat gcaggccctg   1080
ccccctcgc                                                           1089
```

<210> SEQ ID NO 82
<211> LENGTH: 1107
<212> TYPE: DNA
<213> ORGANISM: Artificial Sequence
<220> FEATURE:
<223> OTHER INFORMATION: Nucleic acid sequence of CD70-CAR-7D

<400> SEQUENCE: 82

```
atggccttac cagtgaccgc cttgctcctg ccgctggcct tgctgctcca cgccgccagg     60
ccggaggtgc agctggtgga gtctggggga ggcttggtgc aggctggggg gtctctgaga    120
ctctcctgtg cagcctctgg attcactttc gatgattatg ccataggctg gttccgccag    180
gccccaggga aggagcaaga gggggtctca tgtattagac gtagtgatgg tagcacatgg    240
tatgcaaact ccgtgaaggg ccgattcacc atctccaatg acaacgccaa gaacacggtg    300
tatctgcaaa tgaacagcct gaaacctgag gacacggccg tttattactg cgcagtagat    360
cgttacggtc agagttggca cgagggccgc ggcgctttgg acgcatgggg ccaggggacc    420
ctggtcactg tctcctcaac cacgacgcca gcgccgcgac caccaacacc ggcgcccacc    480
atcgcgtcgc agcccctgtc cctgcgccca gaggcgtgcc ggccagcggc ggggggcgca    540
gtgcacacga gggggctgga cttcgcctgt gatatctaca tctgggcgcc cttggccggg    600
```

```
acttgtgggg tccttctcct gtcactggtt atcacccttt actgcaaacg ggcagaaag    660

aaactcctgt atatattcaa acaaccattt atgagaccag tacaaactac tcaagaggaa    720

gatggctgta gctgccgatt tccagaagaa gaagaaggag gatgtgaact gagagtgaag    780

ttcagcagga gcgcagacgc ccccgcgtac aagcagggcc agaaccagct ctataacgag    840

ctcaatctag gacgaagaga ggagtacgat gttttggaca agagacgtgg ccgggaccct    900

gagatggggg gaaagccgag aaggaagaac cctcaggaag gcctgtacaa tgaactgcag    960

aaagataaga tggcggaggc ctacagtgag attgggatga aaggcgagcg ccggaggggc   1020

aaggggcacg atggccttta ccagggtctc agtacagcca ccaaggacac ctacgacgcc   1080

cttcacatgc aggccctgcc ccctcgc                                       1107


<210> SEQ ID NO 83
<211> LENGTH: 1089
<212> TYPE: DNA
<213> ORGANISM: Artificial Sequence
<220> FEATURE:
<223> OTHER INFORMATION: Nucleic acid sequence of CD70-CAR-H3

<400> SEQUENCE: 83

atggccttac cagtgaccgc cttgctcctg ccgctggcct tgctgctcca cgccgccagg     60

ccgcaggtgc agctcgtgga gtctggggga ggaatggtgc aggctgggcg atctctgaga    120

ctctcctgtg ctgcctctgg aaagcccttc agtttctatt tcatgggatg gtatcgccag    180

gctccaggaa aggagcgcga gttggtcgcc cttattaccg gtgatggtat gacaaactat    240

gcagactccg tggagggccg attcaccatc tccagagaca acgccaagaa tacattgtat    300

ctcgaaatga acagcctgaa acctgaggac acagccgtct attattgcta tgcagatgct    360

tgggcggggg ccgttcgcgc cgagtactgg ggccagggga cccaggtcag cgtctcctca    420

accacgacgc cagcgccgcg accaccaaca ccggcgccca ccatcgcgtc gcagcccctg    480

tccctgcgcc cagaggcgtg ccggccagcg gcggggggcg cagtgcacac gagggggctg    540

gacttcgcct gtgatatcta catctgggcg cccttggccg ggacttgtgg ggtccttctc    600

ctgtcactgg ttatcaccct ttactgcaaa cggggcagaa agaaactcct gtatatattc    660

aaacaaccat ttatgagacc agtacaaact actcaagagg aagatggctg tagctgccga    720

tttccagaag aagaagaagg aggatgtgaa ctgagagtga agttcagcag gagcgcagac    780

gcccccgcgt acaagcaggg ccagaaccag ctctataacg agctcaatct aggacgaaga    840

gaggagtacg atgttttgga caagagacgt ggccgggacc ctgagatggg gggaaagccg    900

agaaggaaga accctcagga aggcctgtac aatgaactgc agaaagataa gatggcggag    960

gcctacagtg agattgggat gaaaggcgag cgccggaggg gcaaggggca cgatggcctt   1020

taccagggtc tcagtacagc caccaaggac acctacgacg cccttcacat gcaggccctg   1080

ccccctcgc                                                           1089


<210> SEQ ID NO 84
<211> LENGTH: 1107
<212> TYPE: DNA
<213> ORGANISM: Artificial Sequence
<220> FEATURE:
<223> OTHER INFORMATION: Nucleic acid sequence of CD70-CAR-L2

<400> SEQUENCE: 84

atggccttac cagtgaccgc cttgctcctg ccgctggcct tgctgctcca cgccgccagg     60
```

```
ccggaggtgc agctggtgga gtccggggga ggcttggtgc aggctggggg gtctctgaga    120

ctctcctgtg cagcctctgg attcactgtc gatgattatg tcataggctg gttccgccag    180

gccccaggga aggagcatga gggggtctca tgtattagta gtaatgatgg tagtacatgg    240

tatgcagact ccgtgaaggg ccgattcacc atctccagtg acaacgccaa gaacacgatg    300

tatctgcaaa tgaacagcct gaaacctgag gacacggccg tttattactg tgcagctaaa    360

tacgcaccct acgggttgga gtactgggag ggaggcatgg actactgggg caaagggacc    420

ctggtcaccg tctcctcaac cacgacgcca gcgccgcgac caccaacacc ggcgcccacc    480

atcgcgtcgc agcccctgtc cctgcgccca gaggcgtgcc ggccagcggc ggggggcgca    540

gtgcacacga gggggctgga cttcgcctgt gatatctaca tctgggcgcc cttggccggg    600

acttgtgggg tccttctcct gtcactggtt atcacccttt actgcaaacg gggcagaaag    660

aaactcctgt atatattcaa acaaccattt atgagaccag tacaaactac tcaagaggaa    720

gatggctgta gctgccgatt tccagaagaa gaagaaggag gatgtgaact gagagtgaag    780

ttcagcagga gcgcagacgc ccccgcgtac aagcagggcc agaaccagct ctataacgag    840

ctcaatctag gacgaagaga ggagtacgat gttttggaca agagacgtgg ccgggaccct    900

gagatggggg gaaagccgag aaggaagaac cctcaggaag gcctgtacaa tgaactgcag    960

aaagataaga tggcggaggc ctacagtgag attgggatga aaggcgagcg ccggaggggc   1020

aaggggcacg atggccttta ccagggtctc agtacagcca ccaaggacac ctacgacgcc   1080

cttcacatgc aggccctgcc ccctcgc                                        1107


<210> SEQ ID NO 85
<211> LENGTH: 1104
<212> TYPE: DNA
<213> ORGANISM: Artificial Sequence
<220> FEATURE:
<223> OTHER INFORMATION: Nucleic acid sequence of CD70-CAR-L1

<400> SEQUENCE: 85

atggccttac cagtgaccgc cttgctcctg ccgctggcct tgctgctcca cgccgccagg     60

ccggaggtgc aggtggtgga gtctggggga ggattggtgc aggctggggg ctctctgaga    120

ctctcctgtg cagcctctgg acgcaccttc agttcatatg ccatgggctg ggtccgccag    180

gctccaggga aggaccaaga gtttgtagcg gctattaact ggagtgatgg tagcacatac    240

tatgcagact ccgtgaaggg ccgattcacc atcgccagag acaacgccaa gaacacggcg    300

tttctgcaaa tgaacagcct gaaacctgag gacacggccg tgtattactg tgcagcaggg    360

tgttgcggag tagctgatgc ccccctcaat gctttggacg catggggcca ggggaccctg    420

gtcactgtct cctcaaccac gacgccagcg ccgcgaccac caacaccggc gcccaccatc    480

gcgtcgcagc ccctgtccct gcgcccagag gcgtgccggc cagcggcggg gggcgcagtg    540

cacacgaggg ggctggactt cgcctgtgat atctacatct gggcgccctt ggccgggact    600

tgtggggtcc ttctcctgtc actggttatc accctttact gcaaacgggg cagaaagaaa    660

ctcctgtata tattcaaaca accatttatg agaccagtac aaactactca agaggaagat    720

ggctgtagct gccgatttcc agaagaagaa gaaggaggat gtgaactgag agtgaagttc    780

agcaggagcg cagacgcccc cgcgtacaag cagggccaga accagctcta taacgagctc    840

aatctaggac gaagagagga gtacgatgtt ttggacaaga gacgtggccg ggaccctgag    900

atggggggaa agccgagaag gaagaaccct caggaaggcc tgtacaatga actgcagaaa    960

gataagatgg cggaggccta cagtgagatt gggatgaaag gcgagcgccg gaggggcaag   1020
```

gggcacgatg gcctttacca gggtctcagt acagccacca aggacaccta cgacgccctt 1080
cacatgcagg ccctgccccc tcgc 1104

<210> SEQ ID NO 86
<211> LENGTH: 21
<212> TYPE: DNA
<213> ORGANISM: Artificial Sequence
<220> FEATURE:
<223> OTHER INFORMATION: Lenti-For

<400> SEQUENCE: 86
tcaagcctca gacagtggtt c 21

<210> SEQ ID NO 87
<211> LENGTH: 24
<212> TYPE: DNA
<213> ORGANISM: Artificial Sequence
<220> FEATURE:
<223> OTHER INFORMATION: Lenti-Rev

<400> SEQUENCE: 87
cctcataaag agacagcaac cagg 24

<210> SEQ ID NO 88
<211> LENGTH: 63
<212> TYPE: DNA
<213> ORGANISM: Artificial Sequence
<220> FEATURE:
<223> OTHER INFORMATION: Signal peptide of CD8a

<400> SEQUENCE: 88
atggccttac cagtgaccgc cttgctcctg ccgctggcct tgctgctcca cgccgccagg 60
ccg 63

<210> SEQ ID NO 89
<211> LENGTH: 135
<212> TYPE: DNA
<213> ORGANISM: Artificial Sequence
<220> FEATURE:
<223> OTHER INFORMATION: Hinge region of CD8a

<400> SEQUENCE: 89
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 90
<211> LENGTH: 75
<212> TYPE: DNA
<213> ORGANISM: Artificial Sequence
<220> FEATURE:
<223> OTHER INFORMATION: Transmembrane domain of CD8a

<400> SEQUENCE: 90
atctacatct gggcgccctt ggccgggact tgtggggtcc ttctcctgtc actggttatc 60
accctttact gcaaa 75

<210> SEQ ID NO 91
<211> LENGTH: 120
<212> TYPE: DNA
<213> ORGANISM: Artificial Sequence
<220> FEATURE:

<223> OTHER INFORMATION: Co-stimulatory signaling domain of 4-1BB

<400> SEQUENCE: 91

```
cggggcagaa agaaactcct gtatatattc aaacaaccat ttatgagacc agtacaaact      60
actcaagagg aagatggctg tagctgccga tttccagaag aagaagaagg aggatgtgaa     120
```

<210> SEQ ID NO 92
<211> LENGTH: 339
<212> TYPE: DNA
<213> ORGANISM: Artificial Sequence
<220> FEATURE:
<223> OTHER INFORMATION: Intracellular signaling domain of CD3z

<400> SEQUENCE: 92

```
ctgagagtga agttcagcag gagcgcagac gcccccgcgt accagcaggg ccagaaccag      60
ctctataacg agctcaatct aggacgaaga gaggagtacg atgttttgga caagagacgt     120
ggccgggacc ctgagatggg gggaaagccg agaaggaaga accctcagga aggcctgtac     180
aatgaactgc agaaagataa gatggcggag gcctacagtg agattgggat gaaaggcgag     240
cgccggaggg gcaaggggca cgatggcctt taccagggtc tcagtacagc caccaaggac     300
acctacgacg cccttcacat gcaggccctg ccccctcgc                            339
```

<210> SEQ ID NO 93
<211> LENGTH: 1518
<212> TYPE: DNA
<213> ORGANISM: Artificial Sequence
<220> FEATURE:
<223> OTHER INFORMATION: Nucleic acid sequence of CD70-CAR-03

<400> SEQUENCE: 93

```
atggccttac cagtgaccgc cttgctcctg ccgctggcct tgctgctcca cgccgccagg      60
ccgggcggca gcgactacaa agacgatgac gacaagggtg gctcccaggc agtggtgacc     120
caggagcctt ccctgacagt gtctccagga gggacggtca cgctcacctg cggcctcaaa     180
tctgggtctg tcacttccga taacttcccc acttggtacc agcagacacc aggccaggct     240
ccccgattgc ttatctacaa cacaaacacc cgtcactctg gcgtccccga ccgcttctcc     300
ggatccatcc tgggcaacaa agccgccctc accatcacgg gggcccaggc cgacgacgag     360
gccgaatatt tctgtgctct gttcataagt aatcctagtg ttgagttcgg cggagggacc     420
caactgaccg tcctaggtgg tggcggtggc tcgggcggtg gtgggtcggg tggcggcgga     480
tctgaggtgc agctcgtgga gtctggggga ggcttggtgc agcctggggg gtctctgaga     540
ctctcctgtg cagcctctgg attcaccttc agtgtctact acatgaactg ggtccgccag     600
gctccaggga aggggctcga gtgggtctca gatattaata atgaaggtgg tactacatac     660
tatgcagact ccgtgaaggg ccgattcacc atctccagag acaactctaa gaacagcctg     720
tatctgcaaa tgaacagcct gcgcgccgag gacacggccg tgtactactg cgcgagagat     780
gccggatata gcaaccatgt acccatcttt gattcttggg gccaggggac cctggtcact     840
gtctcctcaa ccacgacgcc agcgccgcga ccaccaacac cggcgcccac catcgcgtcg     900
cagcccctgt ccctgcgccc agaggcgtgc cggccagcgg cggggggcgc agtgcacacg     960
agggggctgg acttcgcctg tgatatctac atctgggcgc ccttggccgg gacttgtggg    1020
gtccttctcc tgtcactggt tatcaccctt tactgcaaac ggggcagaaa gaaactcctg    1080
tatatattca aacaaccatt tatgagacca gtacaaacta ctcaagagga agatggctgt    1140
agctgccgat ttccagaaga agaagaagga ggatgtgaac tgagagtgaa gttcagcagg    1200
```

-continued

```
agcgcagacg cccccgcgta ccagcagggc cagaaccagc tctataacga gctcaatcta   1260

ggacgaagag aggagtacga tgttttggac aagagacgtg gccgggaccc tgagatgggg   1320

ggaaagccga gaaggaagaa ccctcaggaa ggcctgtaca atgaactgca gaaagataag   1380

atggcggagg cctacagtga gattgggatg aaaggcgagc gccggagggg caaggggcac   1440

gatggccttt accagggtct cagtacagcc accaaggaca cctacgacgc ccttcacatg   1500

caggccctgc cccctcgc                                                 1518


<210> SEQ ID NO 94
<211> LENGTH: 232
<212> TYPE: PRT
<213> ORGANISM: Artificial Sequence
<220> FEATURE:
<223> OTHER INFORMATION: Human Fc sequence

<400> SEQUENCE: 94

Glu Pro Lys Ser Ala Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

ANTIGEN-BINDING PROTEIN TARGETING CD70 AND USE THEREOF

This application is the U.S. National Stage of International Application No. PCT/CN2021/134248, filed on Nov. 30, 2021, which designates the U.S., published in Chinese, and claims priority under 35 U.S.C. § 119 or 365 (c) to Chinese Application No. 202011382464.5, filed on Dec. 1, 2020.

INCORPORATION BY REFERENCE OF MATERIAL IN ASCII TEXT FILE

This application incorporates by reference the Sequence Listing contained in the following ASCII text file:

a) File name: 62341000001_SequenceListing.txt; created May 31, 2023, 98, 770 Bytes in size.

TECHNICAL FIELD

The present application relates to the field of biomedicine, and specifically to an antigen-binding protein targeting CD70 and the use thereof.

BACKGROUND ART

In recent years, with the development of tumor immunotherapy and the progress of clinical research, chimeric antigen receptor-T cells (CAR-T) immunotherapy, with its unique anti-tumor advantages, is currently one of the most promising tumor immunotherapies. CAR-T cells are formed by means of linking a single chain variable region of a monoclonal antibody to a T cell signaling domain. The binding of an antibody to a corresponding tumor antigen can activate T cells in a non-restrictive manner with the major histocompatibility complex, thereby playing an anti-tumor role. The structure of CAR comprises an extracellular antigen-binding region, a hinge region, a transmembrane domain, and an intracellular signaling domain. The selection of a target antigen is a critical determinant for the specificity and effectiveness of CAR, and the safety of genetically engineered T cells.

CD70, a type II transmembrane protein, is a member of the tumor necrosis factor (TNF) family and also known as a tumor necrosis factor receptor super-family (TNFSF) factor, has an ability to regulate the activation, proliferation and differentiation of T cells and B cells, and plays an important role in maintaining the immune response of a body. Currently, the lack of effective targets for solid tumor treatment is one of the bottlenecks limiting CAR-T therapy. Research results showed that CD70 is highly expressed in primary and metastatic kidney cancers, with an expression rate of 100% in renal clear cell carcinoma. CD70 has also been reported to be highly expressed in acute myeloid leukemia stem cells. The high expression of CD70 in tumor tissues can not only induce immune escape, but also activate some immune cells to kill tumor cells. CD70 may serve as a potential target for tumor therapy, bringing a new direction to tumor immunotherapy.

Current CAR-T therapy generally uses a scFv fragment derived from an antigen-binding region of a monoclonal antibody as an antigen-binding region. An extracellular scFv domain can activate the co-stimulatory domain and activation domain of a CAR structure after binding to a target protein expressed on the surface of a target cell. However, scFv has a relatively large molecular weight and is prone to form a polymer, which can affect the function of CAR.

Therefore, there is a need for a CAR containing an antigen-binding region having a new structure.

SUMMARY OF THE INVENTION

The present application provides an antigen-binding protein targeting CD70. In particular, the present application relates to a chimeric antigen receptor containing the antigen-binding protein and the use thereof, and cells containing or expressing the antigen-binding protein, having one or both of the following properties: 1) a strong ability of specifically recognizing and binding to CD70 protein; and 2) a better ability of secreting cytokines IL-2 and IFN-γ.

In one aspect, the present application provides a chimeric antigen receptor, wherein the targeting moiety contains a heavy chain complementary determining region 1 (HCDR1), a heavy chain complementary determining region 2 (HCDR2) and a heavy chain complementary determining region 3 (HCDR3), and the HCDR1 contains an amino acid sequence as shown in any one of SEQ ID NOs: 1, 6, 9, 11, 14, 17, 20, 23, 26, and 29.

In certain embodiments, the HCDR2 contains an amino acid sequence as shown in any one of SEQ ID NOs: 2, 7, 12, 15, 18, 21, 24, 27, 30, and 32.

In certain embodiments, the HCDR3 contains an amino acid sequence as shown in any one of SEQ ID NOs: 3, 4, 5, 8, 10, 13, 16, 19, 22, 25, 28, 31, and 33.

In certain embodiments, the HCDR1, HCDR2 and HCDR3 contain amino acid sequences selected from any one of the groups consisting of:

a) HCDR1: SEQ ID NO: 1, HCDR2: SEQ ID NO: 2, and HCDR3: SEQ ID NO: 3;

b) HCDR1: SEQ ID NO: 1, HCDR2: SEQ ID NO: 2, and HCDR3: SEQ ID NO: 4;

c) HCDR1: SEQ ID NO: 1, HCDR2: SEQ ID NO: 2, and HCDR3: SEQ ID NO: 5;

d) HCDR1: SEQ ID NO: 6, HCDR2: SEQ ID NO: 7, and HCDR3: SEQ ID NO: 8;

e) HCDR1: SEQ ID NO: 9, HCDR2: SEQ ID NO: 7, and HCDR3: SEQ ID NO: 10;

f) HCDR1: SEQ ID NO: 11, HCDR2: SEQ ID NO: 12, and HCDR3: SEQ ID NO: 13;

g) HCDR1: SEQ ID NO: 14, HCDR2: SEQ ID NO: 15, and HCDR3: SEQ ID NO: 16;

h) HCDR1: SEQ ID NO: 17, HCDR2: SEQ ID NO: 18, and HCDR3: SEQ ID NO: 19;

i) HCDR1: SEQ ID NO: 20, HCDR2: SEQ ID NO: 21, and HCDR3: SEQ ID NO: 22;

j) HCDR1: SEQ ID NO: 23, HCDR2: SEQ ID NO: 24, and HCDR3: SEQ ID NO: 25;

k) HCDR1: SEQ ID NO: 26, HCDR2: SEQ ID NO: 27, and HCDR3: SEQ ID NO: 28;

l) HCDR1: SEQ ID NO: 29, HCDR2: SEQ ID NO: 30, and HCDR3: SEQ ID NO: 31;

and m)HCDR1: SEQ ID NO: 23, HCDR2: SEQ ID NO: 32, and HCDR3: SEQ ID NO: 33.

In certain embodiments, the targeting moiety comprises a VHH.

In certain embodiments, the targeting moiety contains an amino acid sequence as shown in any one of SEQ ID NOs: 39, 34, 35, 36, 37, 38, 44, 40, 41, 42, 43, 45, and 46.

In certain embodiments, the chimeric antigen receptor contains a signal peptide.

In certain embodiments, the signal peptide contains a signal peptide derived from a protein selected from the group consisting of CD8, 4-1BB, GM-CSF, CD3γ, CD36, CD3c, CD22, CD79a, CD79b, and CD66d, or a combination thereof.

In certain embodiments, the signal peptide comprises a signal peptide derived from CD8.

In certain embodiments, the signal peptide contains an amino acid sequence as shown in SEQ ID NO: 88.

In certain embodiments, the C-terminus of the signal peptide is linked to the N-terminus of the targeting moiety.

In certain embodiments, the chimeric antigen receptor contains a hinge region.

In certain embodiments, the hinge region contains a hinge region derived from a protein selected from the group consisting of CD8, CD28, IgG, 4-1BB, CD4, CD27, CD7, PD-1 and CH2CH3, or a combination thereof.

In certain embodiments, the hinge region comprises a hinge region derived from CD8a in the CD8.

In certain embodiments, the hinge region contains an amino acid sequence as shown in SEQ ID NO: 89.

In certain embodiments, the N-terminus of the hinge region is linked to the C-terminus of the targeting moiety.

In certain embodiments, the chimeric antigen receptor contains a transmembrane domain.

In certain embodiments, the transmembrane domain contains a transmembrane domain derived from a protein selected from the group consisting of CD8, CD28, 4-1BB, CD4, CD27, CD7, PD-1, CTLA-4, LAG-3, TCRα, TCRβ, TCRγ, TCRδ, CD3ε, CD3δ, CD3γ, CD3ζ a cytokine receptor, CD5, ICOS, OX40, NKG2D, 2B4, CD244, FcεR, FcεRIγ, BTLA, CD30, GITR, HVEM, DAP10, CD2, NKG2C, LIGHT, DAP12, CD40L, TIM1, CD226, DR3, CD45, CD80, CD86, CD9, CD16, CD22, CD33, CD37, CD64, CD134, CD137, CD154 and SLAM, or a combination thereof.

In certain embodiments, the transmembrane domain comprises a transmembrane domain derived from CD8a in the CD8.

In certain embodiments, the transmembrane domain contains an amino acid sequence as shown in SEQ ID NO: 90.

In certain embodiments, the N-terminus of the transmembrane domain is linked to the C-terminus of the hinge region.

In certain embodiments, the chimeric antigen receptor contains a co-stimulatory signaling domain.

In certain embodiments, the co-stimulatory signaling domain contains a co-stimulatory signaling domain derived from a protein selected from the group consisting of CD28, CD137, CD27, CD2, CD7, CD8, CD80, CD86, OX40, CD226, DR3, SLAM, CD5, ICAM, NKG2D, NKG2C, B7-H3, 2B4, FcεRIγ, BTLA, GITR, HVEM, DAP10, DAP12, CD30, CD40, CD40L, TIM1, PD-1, PD-L1, PD-L2, 4-1BBL, OX40L, ICOS-L, CD30L, CD70, CD83, HLA-G, MICA, MICB, a lymphotoxin-β receptor, LFA-1, LIGHT, JAML, CD244, CD100, ICOS, a ligand of CD83, CD40 and MyD88, or a combination thereof.

In certain embodiments, the co-stimulatory signaling domain comprises a co-stimulatory signaling domain derived from 4-1BB.

In certain embodiments, the co-stimulatory signaling domain contains an amino acid sequence as shown in SEQ ID NO: 91.

In certain embodiments, the N-terminus of the co-stimulatory signaling domain is linked to the C-terminus of the transmembrane domain.

In certain embodiments, the chimeric antigen receptor contains an intracellular signaling domain.

In certain embodiments, the intracellular signaling domain contains an intracellular signaling domain derived from a protein selected from the group consisting of CD3ζ, CD3δ, CD3γ, CD3ε, CD79a, CD79b, CD66d, CD5, CD22, FcRγ, FcRβ, FcRε, FcεRIγ, FcεRIβ, FcγRIIa, bovine leukemia virus (BLV) gp30, Epstein-Barr virus (EBV) LMP2A, simian immunodeficiency virus (SIV) PBj14 Nef, Kaposi's sarcoma-associated herpesvirus (KSHV) Kl, DAP10, DAP12 and a domain containing at least one immunoreceptor tyrosine-based activation motif (ITAM), or a combination thereof.

In certain embodiments, the intracellular signaling domain comprises an intracellular signaling domain derived from CD3.

In certain embodiments, the intracellular signaling domain contains an amino acid sequence as shown in SEQ ID NO: 92.

In certain embodiments, the N-terminus of the intracellular signaling domain is linked to the C-terminus of the co-stimulatory signaling domain.

In certain embodiments, the chimeric antigen receptor contains an amino acid sequence as shown in any one of SEQ ID NOs: 60, 61, 62, 63, 64, 65, 66, 67, 68, 69, 70, 71, and 72.

In another aspect, the present application provides an isolated antigen-binding protein, which specifically binds to CD70 at 1 nM or less of a $K_D$ value.

In certain embodiments, the isolated antigen-binding protein contains a heavy chain complementary determining region 1 (HCDR1), a heavy chain complementary determining region 2 (HCDR2) and a heavy chain complementary determining region 3 (HCDR3), wherein the HCDR1 contains an amino acid sequence as shown in any one of SEQ ID NOs: 1, 6, 9, 11, 14, 17, 20, 23, 26, and 29.

In certain embodiments, the HCDR2 contains an amino acid sequence as shown in any one of SEQ ID NOs: 2, 7, 12, 15, 18, 21, 24, 27, 30, and 32.

In certain embodiments, the HCDR3 contains an amino acid sequence as shown in any one of SEQ ID NOs: 3, 4, 5, 8, 10, 13, 16, 19, 22, 25, 28, 31, and 33.

In certain embodiments, the isolated antigen-binding protein is an antibody or an antigen-binding fragment thereof.

In certain embodiments, the isolated antigen-binding protein is a VHH or an antigen-binding fragment thereof.

In certain embodiments, the antibody in the isolated antigen-binding protein is selected from the group consisting of a monoclonal antibody, a chimeric antibody, a humanized antibody and a fully human antibody.

In certain embodiments, the HCDR1, HCDR2 and HCDR3 in the isolated antigen-binding protein contain amino acid sequences selected from any one of the groups consisting of:

a) HCDR1: SEQ ID NO: 1, HCDR2: SEQ ID NO: 2, and HCDR3: SEQ ID NO: 3;
b) HCDR1: SEQ ID NO: 1, HCDR2: SEQ ID NO: 2, and HCDR3: SEQ ID NO: 4;
c) HCDR1: SEQ ID NO: 1, HCDR2: SEQ ID NO: 2, and HCDR3: SEQ ID NO: 5;
d) HCDR1: SEQ ID NO: 6, HCDR2: SEQ ID NO: 7, and HCDR3: SEQ ID NO: 8;
e) HCDR1: SEQ ID NO: 9, HCDR2: SEQ ID NO: 7, and HCDR3: SEQ ID NO: 10;
f) HCDR1: SEQ ID NO: 11, HCDR2: SEQ ID NO: 12, and HCDR3: SEQ ID NO: 13;
g) HCDR1: SEQ ID NO: 14, HCDR2: SEQ ID NO: 15, and HCDR3: SEQ ID NO: 16;
h) HCDR1: SEQ ID NO: 17, HCDR2: SEQ ID NO: 18, and HCDR3: SEQ ID NO: 19;

i) HCDR1: SEQ ID NO: 20, HCDR2: SEQ ID NO: 21, and HCDR3: SEQ ID NO: 22;
j) HCDR1: SEQ ID NO: 23, HCDR2: SEQ ID NO: 24, and HCDR3: SEQ ID NO: 25;
k) HCDR1: SEQ ID NO: 26, HCDR2: SEQ ID NO: 27, and HCDR3: SEQ ID NO: 28;
l) HCDR1: SEQ ID NO: 29, HCDR2: SEQ ID NO: 30, and HCDR3: SEQ ID NO: 31; and m)HCDR1: SEQ ID NO: 23, HCDR2: SEQ ID NO: 32, and HCDR3: SEQ ID NO: 33.

In certain embodiments, the isolated antigen-binding protein comprises a VHH.

In certain embodiments, the isolated antigen-binding protein contains an amino acid sequence as shown in any one of SEQ ID NOs: 39, 34, 35, 36, 37, 38, 44, 40, 41, 42, 43, 45, and 46.

In another aspect, the present application provides an isolated nucleic acid molecule, which encodes the chimeric antigen receptor and/or the isolated antigen-binding protein.

In certain embodiments, the isolated nucleic acid molecule contains a nucleic acid sequence as shown in any one of SEQ ID NOs: 47-59 and/or SEQ ID NOs: 73-85.

In another aspect, the present application provides one or more vectors, which contain the isolated nucleic acid molecule.

In certain embodiments, the vector comprises a viral vector.

In certain embodiments, the vector comprises a lentivirus vector.

In another aspect, the present application provides one or more cells, which contains the chimeric antigen receptor, the isolated antigen-binding protein, the isolated nucleic acid molecule, and/or the vector.

In certain embodiments, the cell comprises an immune cell.

In certain embodiments, the immune cell is selected from the group consisting of a T cell, a B cell, a natural killer cell (NK cell), a macrophage, an NKT cell, a monocyte, a dendritic cell, a granulocyte, a lymphocyte, a leukocyte, and/or a peripheral blood mononuclear cell.

In certain embodiments, the cell comprises a T cell.

In certain embodiments, the cell has a reduced expression and/or activity of CD70 compared to a corresponding wild-type cell.

In certain embodiments, the cell comprises a CD70 knockout compared to a corresponding wild-type cell.

In another aspect, the present application provides a pharmaceutical composition, which contains the chimeric antigen receptor, the isolated antigen-binding protein, the isolated nucleic acid molecule, the vector, the cell, and/or a pharmaceutically acceptable adjuvant and/or excipient.

In another aspect, the chimeric antigen receptor, the isolated antigen-binding protein, the isolated nucleic acid molecule, the vector, the cell, and/or the pharmaceutical composition are used for treating a disease or disorder associated with the expression of CD70.

In certain embodiments, the disease or disorder associated with the expression of CD70 comprise acute myeloid leukemia (AML) or kidney cancer.

In another aspect, provided is the use of the chimeric antigen receptor, the isolated antigen-binding protein, the isolated nucleic acid molecule, the vector, the cell, and/or the pharmaceutical composition in the preparation of a drug, wherein the drug is used for treating a disease or disorder associated with the expression of CD70.

In certain embodiments, according to the use, the disease or disorder associated with the expression of CD70 comprise acute myeloid leukemia (AML) or kidney cancer.

In another aspect, the present application provides a method for preventing and/or treating a disease or disorder associated with the expression of CD70, which method comprises: administering to a subject in need thereof an effective amount of the chimeric antigen receptor, the isolated antigen-binding protein, the isolated nucleic acid molecule, the vector, the cell, and/or the pharmaceutical composition.

In certain embodiments, the disease or disorder associated with the expression of CD70 comprise acute myeloid leukemia (AML) or kidney cancer.

A person skilled in the art would have been able to easily notice other aspects and advantages of the present application from the detailed description below. Only exemplary embodiments of the present application are shown and described in the detailed description below. As a person skilled in the art will recognize, the content of the present application enables a person skilled in the art to make alterations to the disclosed specific embodiments without departing from the spirit and scope of the invention disclosed in the present application. Accordingly, the description in the drawings and description of the present application is merely exemplary rather than limiting.

BRIEF DESCRIPTION OF THE DRAWINGS

The specific features of the invention disclosed in the present application are as shown in the appended claims. The characteristics and advantages of the invention disclosed in the present application can be better understood with reference to the exemplary embodiments and drawings detailed herein below. The brief description of the drawings is as follows:

DETAILED DESCRIPTION OF EMBODIMENTS

Figure 1:
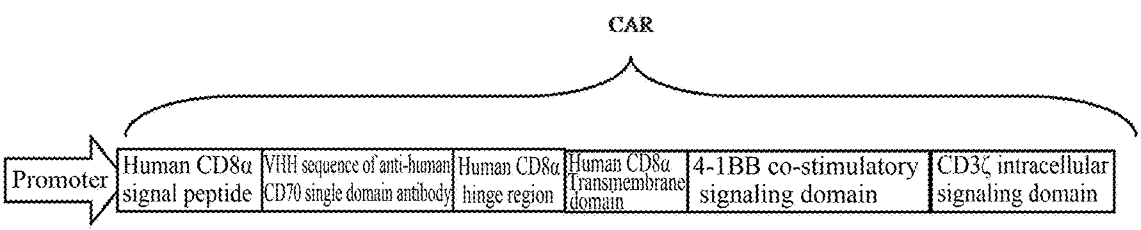
FIG. 1 shows the structure of the CAR targeting CD70 of the present application.
Figure 2:
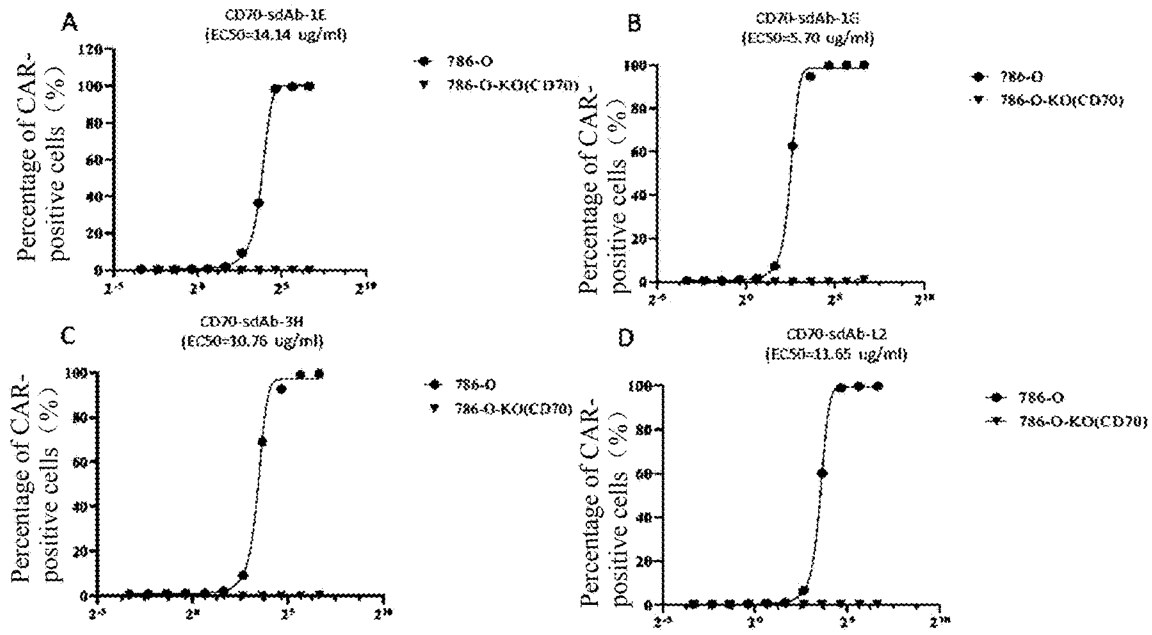
FIGS. 2A-2D show the binding affinity of the single domain antibodies targeting CD70 of the present application to a cell line 786-0.

The embodiments of the present invention are illustrated below by using the specific examples, and those skilled in the art would have readily understood other advantages and effects of the present invention from the content disclosed in this description.

DEFINITION OF TERMS

In the present application, the term "isolated antigen-binding protein" generally refers to a polypeptide polymer capable of specifically recognizing and/or neutralizing a specific antigen. For example, the isolated antigen-binding protein may comprise a portion of a heavy chain. For example, the isolated antigen-binding protein may comprise a heavy chain variable region. The term "isolated antigen-binding protein" may comprise a single domain antibody. For example, the isolated antigen-binding protein may comprise, but is not limited to, a human single domain antibody.

In the present application, the term "single domain antibody", "sdAb" or "VHH" generally refers to a class of antibodies that lack light chains and have only heavy chain variable regions. In certain cases, the single domain antibody can be derived from *Camelus bactrianus, Camelus dromedarius, Vicugna pacos, Lama glama*, nurse shark, smooth dogfish, or ray (for example, see KANG, Xiaozhen et al., Chinese Journal of Biotechnology, 2018, 34(12): 1974-1984). For example, the single domain antibody can be derived from *Vicugna* pacos. The single domain antibody can be composed of a heavy chain variable region (VH). The term "heavy chain variable region" generally refers to an amino terminal domain of a heavy chain of an antigen-binding fragment. The heavy chain variable region can be further divided into hypervariable regions called complementarity determining regions (CDRs), which are scattered within more conserved regions called framework regions (FRs). Each heavy chain variable region can be composed of three CDRs and four FRs, which can be arranged from an amino terminus to a carboxyl terminus in the following order: FR1, CDR1, FR2, CDR2, FR3, CDR3, and FR4. The heavy chain variable region contains a binding domain that interacts with an antigen (e.g., CD70).

In the present application, the terms "CD70 antigen" and "CD70 protein" are used interchangeably, comprise any variants and homologs of CD70, and are naturally expressed on cells or expressed on cells transfected with CD70 genes. In the present application, CD70 can be human CD70, which has the accession number NM 001252.5 in GenBank and the accession number P32970 in UniProt/Swiss-Prot. For example, the CD70 protein may contain a homolog of human CD70 protein. In the present application, the term "homolog" generally refers to an amino acid sequence or a nucleotide sequence having a certain homology to the amino acid sequence of human CD70 protein and the nucleotide sequence of human CD70 protein. The term "homology" can be equivalent to sequence "identity". A homologous sequence may comprise an amino acid sequence that can be at least 80%, 85%, 90%, 99.1%, 99.2%, 99.3%, 99.4%, 99.5%, 99.6%, 99.7%, 99.8% or 99.9% identical to the subject sequence. Generally, homologs will contain active sites, etc. that are identical to the subject amino acid sequence. Homology can be considered on the basis of similarity (i.e., amino acid residues having similar chemical properties/functions), or can be represented in terms of sequence identity. In the present application, a sequence having a percentage identity to any one of the amino acid sequence or nucleotide sequence of the mentioned SEQ ID NO refers to a sequence having the percentage identity over the full-length sequence of the mentioned SEQ ID NO. To determine a sequence identity, sequence alignment can be performed by using various methods known to a person skilled in the art, for example, using softwares such as BLAST, BLAST-2, ALIGN, NEEDLE or Megalign (DNASTAR). A person skilled in the art can determine appropriate parameters for alignment, including any algorithms required for achieving optimal alignment over the compared full-length sequences.

In the present application, the term "transmembrane domain" generally refers to a sequence in a cell surface protein that spans the cell membrane, and may contain a hydrophobic α-helix. The transmembrane domain can be linked to an intracellular signaling domain, playing a role in transmitting signals. In the present application, the transmembrane domain can be derived from any type I, type II or type III transmembrane protein. In the present application, the transmembrane domain may contain a transmembrane domain derived from a protein selected from the group consisting of CD8, CD28, 4-1BB, CD4, CD27, CD7, PD-1, a subunit of a T cell receptor, a polypeptide that forms a CD3 complex, an IL2 receptor, CD5, ICOS, OX40, NKG2D, 2B4, CD244, FcεR, FcεRIγ, BTLA, CD30, GITR, HVEM, DAP10, CD2, NKG2C, LIGHT, DAP12, CD40L, TIM1, CD226, DR3, CD45, CD80, CD86, CD9, CD16, CD22, CD33, CD37, CD64, CD134, CD137, CD154 and SLAM, or a combination thereof. For example, the subunits of T cell receptors may comprise TCRα, TCRβ, TCRγ or TCRδ. For example, the polypeptide that forms a CD3 complex may comprise CD3c, CD36, CD3γ or CD3ζ. For example, the transmembrane domain may comprise a transmembrane domain derived from CD8a in the CD8.

In the present application, the term "chimeric antigen receptor (CAR)" generally refers to a fusion protein containing a targeting moiety capable of binding to an antigen and at least one intracellular domain. CAR is the core component of a chimeric antigen receptor T cell (CAR-T), and may comprise a targeting moiety (e.g., a specific antigen targeting a tumor and/or a tumor-associated antigen), a signal peptide, a transmembrane domain, a co-stimulatory signaling domain, and an intracellular signaling domain. In the present application, the CAR can be combined with the activated intracellular domain of a T cell receptor on the basis of the antigen (e.g., CD70) specificity of an antibody. A genetically modified T cell expressing CAR may specifically recognize and eliminate a malignant cell expressing a target antigen. For the description of CAR and CAR-T cells, reference can be made to, for example, Sadelain M, Brentjens R, Rivi 'ere I. The basic principles of chimeric antigen receptor design. Cancer Discov. 2013; 3(4):388-398; Turtle C J, Hudecek M, Jensen M C, Riddell S R. Engineered T cells for anti-cancer therapy. Curr Opin Immunol. 2012; 24(5):633-639; Dotti G, Gottschalk S, Savoldo B, Brenner M K. Design and development of therapies using chimeric antigen receptor-expressing T cells. Immunol Rev. 2014; 257(1):107-126; WO 2013154760 and WO 2016014789.

In the present application, the term "co-stimulatory signaling domain" generally refers to an intracellular domain that may provide an immune co-stimulatory molecule, wherein the co-stimulatory molecule is a cell surface molecule that is required for an efficient response of lymphocytes to an antigen. In certain cases, the co-stimulatory signaling domain may contain a co-stimulatory signaling domain derived from a protein selected from the group consisting of CD28, CD137, CD27, CD2, CD7, CD8, CD80, CD86, OX40, CD226, DR3, SLAM, CD5, ICAM, NKG2D, NKG2C, B7-H3, 2B4, FcεRIγ, BTLA, GITR, HVEM, DAP10, DAP12, CD30, CD40, CD40L, TIM1, PD-1, PD-L1, PD-L2, 4-1BBL, OX40L, ICOS-L, CD30L, CD70, CD83, HLA-G, MICA, MICB, a lymphotoxin-β receptor, LFA-1, LIGHT, JAML, CD244, CD100, ICOS, a ligand of CD83, CD40 and MyD88, or a combination thereof. For example, the co-stimulatory signaling domain may comprise a co-stimulatory signaling domain derived from 4-1BB.

In the present application, the term "hinge region" generally refers to a connecting region between a targeting moiety (e.g., an extracellular domain targeting CD70) and a transmembrane domain. In certain cases, the hinge region may contain a hinge region derived from a protein selected from the group consisting of CD8, CD28, IgG, 4-1BB, CD4, CD27, CD7, PD-1 and CH2CH3, or a combination thereof. For example, the hinge region may comprise a hinge region derived from CD8a in the CD8.

In the present application, the term "intracellular signaling domain" generally refers to a domain located inside a cell that can transduce signals. In the present application, the intracellular signaling domain may transduce signals into a cell. Generally, the intracellular signaling domain is any continuous amino acid sequence used for guiding protein targeting. In certain cases, the intracellular signaling domain may contain an intracellular signaling domain derived from a protein selected from the group consisting of CD3, CD36, CD3γ, CD3c, CD79a, CD79b, CD66d, CD5, CD22, FεRγ, FcRβ, FcRε, FcεRIγ, FcεRIβ, FcγRIIa, bovine leukemia virus gp30, Epstein-Barr virus (EBV) LMP2A, simian immunodeficiency virus PBj14 Nef, Kaposi's sarcoma-associated herpesvirus (HSKV), DAP10, DAP12 and a domain containing at least one ITAM, or a combination thereof. For example, the intracellular signaling domain may comprise an intracellular signaling domain derived from CD3ζ.

In the present application, the term "signal peptide" generally refers to a leader sequence at the amino terminus (N-terminus) of a chimeric antigen receptor (CAR), which guides the CAR molecule to the endoplasmic reticulum during or after translation. In certain cases, the signal peptide may contain a signal peptide derived from a protein selected from the group consisting of CD8, 4-1BB, GM-CSF, CD3γ, CD36, CD3c, CD22, CD79a, CD79b, and CD66d, or a combination thereof. For example, the signal peptide may comprise a signal peptide derived from CD8.

In the present application, the term "antibody" generally refers to a polypeptide molecule capable of specifically recognizing and/or neutralizing a specific antigen. For example, the antibody may contain an immunoglobulin composed of at least two heavy (H) chains and two light (L) chains interlinked via disulfide bonds, and comprise any molecule containing an antigen-binding moiety thereof. The term "antibody" comprises a monoclonal antibody, an antibody fragment or an antibody derivative, including but not limited to a human antibody (fully human antibody), a humanized antibody, a chimeric antibody, a single chain antibody (e.g., scFv), and an antibody fragment (e.g., Fab, Fab' and (Fab) 2 fragments) that bind to an antigen. The term "antibody" also comprises all forms of recombinant antibodies, for example, an antibody expressed in a prokaryotic cell, an unglycosylated antibody, and any antibody fragments and derivatives thereof that bind to an antigen as described herein. Each heavy chain can be composed of a heavy chain variable region (VH) and a heavy chain constant region. Each light chain can be composed of a light chain variable region (VL) and a light chain constant region. VH and VL regions can be further divided into hypervariable regions called complementary determining regions (CDRs), which are scattered within more conserved regions called framework regions (FRs). Each VH and VL can be composed of three CDRs and four FRs, which can be arranged from an amino terminus to a carboxyl terminus in the following order: FR1, CDR1, FR2, CDR2, FR3, CDR3, and FR4. The variable regions of the heavy chain and light chain contain binding domains that interact with an antigen. The constant regions of an antibody can mediate the binding of the immunoglobulin to a host tissue or factor, wherein the host tissue or factor comprises various cells of the immune system (e.g., effector cells) and the first component (C1q) of the classical complement system.

In the present application, the term "antigen-binding fragment" generally refers to one or more fragments of an antibody that play a role in specifically binding to an antigen. The antigen-binding function of an antibody can be achieved by the full-length fragment of the antibody. The antigen-binding function of an antibody can also be achieved by: a heavy chain comprising fragments of Fv, ScFv, dsFv, Fab, Fab' or F(ab')2, or a light chain comprising fragments of Fv, ScFv, dsFv, Fab, Fab' or F(ab')2. (1) a Fab fragment, i.e., a monovalent fragment consisting of VL, VH, CL and CH domains; (2) a F(ab')2 fragment, containing a divalent fragment of two Fab fragments linked via a disulfide bond in a hinge region; (3) a Fd fragment consisting of VH and CH domains; (4) a Fv fragment consisting of VL and VH domains of a single arm of an antibody; (5) a dAb fragment consisting of a VH domain (Ward et al., 1989, Nature 341: 544-546); (6) an isolated complementary determining region (CDR); and (7) a combination of two or more isolated CDRs that can be optionally linked via a linker. In addition, a monovalent single-chain molecule Fv (scFv) formed by means of pairing VL and VH may also be comprised (see Bird et al., 1988, Science 242:423-426; and Huston et al., (1988) Proc.Natl.Acad.Sci. 85:5879-5883). The "antigen-binding fragment" may also comprise an immunoglobulin fusion protein, which contains a binding domain selected from the group consisting of: (1) a binding domain polypeptide fused with an immunoglobulin hinge region polypeptide; (2) an immunoglobulin heavy chain CH2 constant region fused with a hinge region; and (3) an immunoglobulin heavy chain CH3 constant region fused with a CH2 constant region. For example, the antigen-binding fragment may also comprise a single domain antibody.

In the present application, the term "acute myeloid leukemia (AML)" generally refers to a clonal malignant proliferative disease of myeloid blasts of the hematopoietic system. Acute myeloid leukemias may comprise all acute non-lymphocytic leukemias.

In the present application, the term "kidney cancer" generally refers to a disease in which kidney cells undergo pathological changes (carcinogenesis) and grow out of control, forming tumors. Clinically variable symptoms comprise varying degrees of anemia, hematuria, persistent pain on one side of the body, and swollen ankles or legs, etc.

In the present application, the term "$K_D$" can be used interchangeably with "$K_D$" and generally refers to the dissociation equilibrium constant of a specific antibody-antigen interaction, with unit of M (mol/L). $K_D$ can be calculated on the basis of the concentrations of substance AB and substances A and B obtained by the dissociation of substance AB: $K_D$=c(A)*c(B)/c(AB). It can be seen from the formula, the larger the $K_D$ value, the more dissociation occurs, indicating a weaker affinity between substance A and substance B; and conversely, the smaller the $K_D$ value, the less dissociation occurs, indicating a stronger affinity between substance A and substance B.

In the present application, the term "Raji cell" generally refers to a continuous human cell line capable of producing an Epstein-Barr virus strain. A virus transforms cord blood lymphocytes and induces an early antigen in the Raji cell.

Raji cell is widely used as a transfection host and also used for understanding hematopoietic cells and other cellular malignancies. In addition, Raji cell also be used for detecting immune complexes because the Raji cell has and expresses several receptors of certain complement components and Fc receptor of immunoglobulin G.

In the present application, the term "786-0 cell" generally refers to a human renal clear cell adenocarcinoma cell. The cell line is derived from one primary clear cell carcinoma. This cell has microvilli and desmosomes.

In the present application, the term "THP-1 cell" generally refers to a human acute monocytic leukemia cell line. This cell line may phagocytose latex particles and activated red blood cell, contains no immunoglobulins within both the cell membrane and cytoplasm, expresses C3R and FcR, and can be induced by phorbol ester TPA to differentiate into a mononuclear line.

In the present application, the term "K562 cell" generally refers to a human immortalized myelogenous leukemia cell line. K562 belongs to an erythroleukemia cell line, with the characteristics of high malignancy and rapid proliferation. K562 is originally isolated from the hydrothorax of a 53-year-old female patient with chronic myelogenous leukemia (CIVIL) in acute phase.

In the present application, the term "nucleic acid molecule" generally refers to any length of nucleotides, deoxyribonucleotides, ribonucleotides, or analogs thereof in isolated form, which are either isolated from their natural environments or artificially synthesized.

In the present application, the term "vector" generally refers to a nucleic acid molecule capable of self-replicating in a suitable host. The vector can transfer an inserted nucleic acid molecule into and/or between cells. The vector may comprise a vector primarily used for inserting DNA or RNA into a cell, a vector primarily used for replicating DNA or RNA, and a vector primarily used for the transcriptional and/or translational expression of DNA or RNA. The vector can be a polynucleotide that can be transcribed and translated into a polypeptide when introduced into a suitable cell. Generally, the vector may produce a desired expression product by means of culturing a suitable cell containing the vector. In the present application, the vector may contain a lentiviral vector.

In the present application, the term "cell" generally refers to an individual cell, cell line or cell culture that may contain or has contained a plasmid or vector containing the nucleic acid molecule of the present application, or may express the chimeric antigen receptor of the present application or the antigen-binding protein of the present application. The cell may comprise the progeny of a single cell. Due to natural, accidental, or intentional mutations, progeny cells may not necessarily be completely identical to original parent cells in terms of morphology or genome, so long as they can express the chimeric antigen receptor or antigen-binding protein of the present application. The cell can be obtained by means of transfecting a cell in vitro with the vector of the present application. The cell can be a prokaryotic cell (e.g., *Escherichia coli*), and may also be a eukaryotic cell (e.g., a yeast cell, such as a COS cell, a Chinese hamster ovary (CHO) cell, a HeLa cell, an HEK293 cell, a COS-1 cell, an NS0 cell, or a myeloma cell). In some embodiments, the cell can be an immune cell. For example, the immune cell can be selected from the group consisting of a T cell, a B cell, a natural killer cell (NK cell), a macrophage, an NKT cell, a monocyte, a dendritic cell, a granulocyte, a lymphocyte, a leukocyte, and/or a peripheral blood mononuclear cell. For example, the immune cell can be a T cell.

In the present application, the terms "treating" and "treatment" generally refer to: (i) preventing a disease, disorder or condition from occurring in a patient who can be susceptible to the disease, disorder and/or condition but has not yet been diagnosed; (ii) inhibiting the disease, disorder or condition, i.e., arresting the development thereof; and (iii) alleviating the disease, disorder or condition, i.e., causing the regression of the disease, disorder and/or condition, and/or symptoms associated with the disease, disorder or condition.

In the present application, the terms "polypeptide", "peptide" and "protein" are used interchangeably and generally refer to polymers of amino acids of any length. The polymer can be linear or branched, may contain a modified amino acid, and can be interrupted by a non-amino acid. These terms also encompass amino acid polymers that have been modified. These modifications may contain: disulfide bond formation, glycosylation, lipidation, acetylation, phosphorylation, or any other manipulation (such as binding to labeled components). The term "amino acid" comprises natural and/or unnatural or synthetic amino acids, including glycine, both D and L optical isomers, amino acid analogs and peptidomimetics.

In the present application, the terms "polynucleotide", "nucleotide", "nucleotide sequence", "nucleic acid" and "oligonucleotide" are used interchangeably, and generally refer to polymerization forms of nucleotides of any length, such as deoxyribonucleotides or ribonucleotides, or analogs thereof. A polynucleotide may have any three-dimensional structure and may perform any known or unknown function. Non-limiting examples of polynucleotides comprise a coding region or a non-coding region of a gene or a gene fragment, multiple loci (one locus) defined by connection analysis, an exon, an intron, a messenger RNA (mRNA), a transfer RNA, a ribosomal RNA, a short interfering RNA (siRNA), a short hairpin RNA (shRNA), a micro-RNA (miRNA), a ribozyme, a cDNA, a recombinant polynucleotide, a branched polynucleotide, a plasmid, a vector, an isolated DNA of any sequence, an isolated RNA of any sequence, a nucleic acid probe and a primer. A polynucleotide may contain one or more modified nucleotides, such as methylated nucleotides and nucleotide analogs. If present, modification of a nucleotide structure can be performed before or after the assembly of a polymer. The sequence of a nucleotide can be interrupted by non-nucleotide components. Polynucleotides can be further modified after polymerization, for example, by conjugation with labeled components.

In addition to the specific proteins and nucleotides mentioned herein, the present application may also comprise functional variants, derivatives, analogs, homologs, and fragments of the proteins and nucleotides.

The term "functional variant" refers to a polypeptide that has an amino acid sequence substantially identical to a naturally occurring sequence, or is encoded by a substantially identical nucleotide sequence and can have one or more activities of a naturally occurring sequence. In the context of the present application, a variant of any given sequence refers to a sequence in which a specific sequence of a residue (whether an amino acid residue or a nucleotide residue) has been modified so that the polypeptide or the polynucleotide substantially retains at least one endogenous function. A variant sequence can be obtained by means of the addition, deletion, substitution, modification, replacement and/or variation of at least one amino acid residue and/or nucleotide residue present in a naturally occurring protein and/or polynucleotide, as long as the original functional activity can be maintained.

In the present application, the term "derivative" generally refers to the polypeptide or polynucleotide of the present application, comprising any substitution, variation, modification, replacement, deletion, and/or addition of one or more amino acid residues from/on a sequence, as long as the obtained polypeptide or polynucleotide substantially retains at least one endogenous function thereof.

In the present application, for a polypeptide or polynucleotide, the term "analog" generally comprises any mimics of the polypeptide or polynucleotide, that is, a chemical compound that possesses at least one endogenous function of the polypeptide or polynucleotide simulated by the mimic.

Generally, amino acid substitution can be performed, for example, at least one (e.g., 1, 2, 3, 4, 5, 6, 7, 8, 9, 10, or more than 20) amino acid substitution, as long as a modified sequence substantially retains the desired activity or ability. Amino acid substitution may comprise the use of a non-naturally occurring analog.

Proteins or peptides used in the present application may also have the deletion, insertion or substitution of amino acid residues, and the amino acid residues produce silent changes and lead to functionally equivalent proteins. Intentional amino acid substitution can be performed on the basis of the similarity between the polarity, charge, solubility, hydrophobicity, hydrophilicity, and/or amphipathicity of residues, as long as the endogenous function is retained. For example, negatively charged amino acids comprise aspartic acid and glutamic acid; positively charged amino acids comprise lysine and arginine; and amino acids containing uncharged polar head groups with similar hydrophilic values comprise asparagine, glutamine, serine, threonine, and tyrosine.

In the present application, the term "and/or" should be understood to mean either one of optional items or both of the optional items.

In the present application, the terms "contain", "contains" and "containing" generally refer to comprising explicitly specified features, but not excluding other elements.

In the present application, the term "approximately" generally refers to a change within a range of 0.5%-10% above or below a specified value, for example, a change within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below a specified value.

In the present application, the terms "comprise", "comprises" and "comprising" generally refer to the meaning of containing, encompassing, having or including, and in certain cases, the terms also mean "being . . . " or "consisting of . . . ".

DETAILED DESCRIPTION OF THE INVENTION

Antigen-Binding Protein and Chimeric Antigen Receptor

In one aspect, the present application provides an isolated antigen-binding protein. In the present application, the isolated antigen-binding protein may contain a targeting moiety capable of specifically binding to CD70. In another aspect, the present application provides a chimeric antigen receptor (CAR) containing the isolated antigen-binding protein (for example, the targeting moiety capable of specifically binding to CD70).

In the present application, the isolated antigen-binding protein may contain a heavy chain complementary determining region 1 (HCDR1), a heavy chain complementary determining region 2 (HCDR2) and a heavy chain complementary determining region 3 (HCDR3), wherein the HCDR1 may contain an amino acid sequence as shown in any one of SEQ ID NOs: 1, 6, 9, 11, 14, 17, 20, 23, 26 and 29. For example, the HCDR1 may contain an amino acid sequence having at least 80% (for example, at least 85%, 90%, 91%, 92%, 93%, 94%, 95%, 96%, 97%, 98%, 99%, or higher) sequence homology to an amino acid sequence as shown in any one of SEQ ID NOs: 1, 6, 9, 11, 14, 17, 20, 23, 26, and 29.

In the present application, the HCDR2 may contain an amino acid sequence as shown in any one of SEQ ID NOs: 2, 7, 12, 15, 18, 21, 24, 27, 30 and 32. For example, the HCDR2 may contain an amino acid sequence having at least 80% (for example, at least 85%, 90%, 91%, 92%, 93%, 94%, 95%, 96%, 97%, 98%, 99%, or higher) sequence homology to an amino acid sequence as shown in any one of SEQ ID NOs: 2, 7, 12, 15, 18, 21, 24, 27, 30, and 32.

In the present application, the HCDR3 may contain an amino acid sequence as shown in any one of SEQ ID NOs: 3, 4, 5, 8, 10, 13, 16, 19, 22, 25, 28, 31 and 33. For example, the HCDR3 may contain an amino acid sequence having at least 80% (for example, at least 85%, 90%, 91%, 92%, 93%, 94%, 95%, 96%, 97%, 98%, 99%, or higher) sequence homology to an amino acid sequence as shown in any one of SEQ ID NOs: 3, 4, 5, 8, 10, 13, 16, 19, 22, 25, 28, 31 and 33.

In the present application, the isolated antigen-binding protein may contain HCDR1, HCDR2, and HCDR3. For example, the HCDR1, HCDR2 and HCDR3 may contain amino acid sequences selected from any one of the groups consisting of, or the isolated antigen-binding protein may contain an amino acid sequence having at least 80% (for example, at least 85%, 90%, 91%, 92%, 93%, 94%, 95%, 96%, 97%, 98%, 99%, or higher) sequence homology to an amino acid sequence selected from any one of the groups consisting of:

a) HCDR1: SEQ ID NO: 1, HCDR2: SEQ ID NO: 2, and HCDR3: SEQ ID NO: 3;
b) HCDR1: SEQ ID NO: 1, HCDR2: SEQ ID NO: 2, and HCDR3: SEQ ID NO: 4;
c) HCDR1: SEQ ID NO: 1, HCDR2: SEQ ID NO: 2, and HCDR3: SEQ ID NO: 5;
d) HCDR1: SEQ ID NO: 6, HCDR2: SEQ ID NO: 7, and HCDR3: SEQ ID NO: 8;
e) HCDR1: SEQ ID NO: 9, HCDR2: SEQ ID NO: 7, and HCDR3: SEQ ID NO: 10;
f) HCDR1: SEQ ID NO: 11, HCDR2: SEQ ID NO: 12, and HCDR3: SEQ ID NO: 13;
g) HCDR1: SEQ ID NO: 14, HCDR2: SEQ ID NO: 15, and HCDR3: SEQ ID NO: 16;
h) HCDR1: SEQ ID NO: 17, HCDR2: SEQ ID NO: 18, and HCDR3: SEQ ID NO: 19;
i) HCDR1: SEQ ID NO: 20, HCDR2: SEQ ID NO: 21, and HCDR3: SEQ ID NO: 22;
j) HCDR1: SEQ ID NO: 23, HCDR2: SEQ ID NO: 24, and HCDR3: SEQ ID NO: 25;
k) HCDR1: SEQ ID NO: 26, HCDR2: SEQ ID NO: 27, and HCDR3: SEQ ID NO: 28;
l) HCDR1: SEQ ID NO: 29, HCDR2: SEQ ID NO: 30, and HCDR3: SEQ ID NO: 31;
and m)HCDR1: SEQ ID NO: 23, HCDR2: SEQ ID NO: 32, and HCDR3: SEQ ID NO: 33.

In the present application, the antigen-binding protein may also comprise a framework region, which can be a framework region derived from a human antibody, or derived from a single domain antibody of species such as *Vicugna pacos* and camels. For example, the framework region of the antigen-binding protein can be derived from human. For example, the framework region of the antigen-binding protein can be derived from human.

In the present application, the antigen-binding protein may comprise an Fc region. In certain cases, the antigen-binding protein may comprise a single domain antibody.

In certain cases, the antigen-binding protein may comprise a VHH.

In certain cases, the targeting moiety of the chimeric antigen receptor may contain a VHH.

In the present application, the VHH may contain an amino acid sequence as shown in any one of SEQ ID NOs: 39, 34, 35, 36, 37, 38, 44, 40, 41, 42, 43, 45 and 46. For example, the VHH may contain an amino acid sequence having at least 80% (for example, at least 85%, 90%, 91%, 92%, 93%, 94%, 95%, 96%, 97%, 98%, 99%, or higher) sequence homology to an amino acid sequence as shown in any one of SEQ ID NOs: 39, 34, 35, 36, 37, 38, 44, 40, 41, 42, 43, 45 and 46.

In the present application, the chimeric antigen receptor may also contain an intracellular domain in addition to an extracellular targeting moiety (e.g., targeting CD70).

In certain cases, the chimeric antigen receptor may contain a signal peptide. The signal peptide may comprise, but is not limited to, a signal peptide derived from a protein selected from the group consisting of CD8, 4-1BB, GM-CSF, CD3γ, CD3δ, CD3ε, CD22, CD79a, CD79b, and CD66d, or a combination thereof. For example, the signal peptide can be a signal peptide derived from CD8. For example, the signal peptide may contain an amino acid sequence as shown in SEQ ID NO: 88.

In certain cases, the chimeric antigen receptor may contain a hinge region. The hinge region may comprise, but is not limited to, a hinge region derived from a protein selected from the group consisting of CD8, CD28, IgG, 4-1BB, CD4, CD27, CD7, PD-1 and CH2CH3, or a combination thereof. For example, the hinge region can be a hinge region derived from CD8a in the CD8. For example, the hinge region may contain an amino acid sequence as shown in SEQ ID NO: 89.

In certain cases, the chimeric antigen receptor may contain a transmembrane domain. The transmembrane domain may contain a transmembrane domain derived from a protein selected from the group consisting of CD8, CD28, 4-1BB, CD4, CD27, CD7, PD-1, CTLA-4, LAG-3, TCRα, TCRβ, TCRγ, TCRδ, CD3ε, CD3δ, CD3γ, CD3ζ, a cytokine receptor, CD5, ICOS, OX40, NKG2D, 2B4, CD244, FcεR, FcεRIγ, BTLA, CD30, GITR, HVEM, DAP10, CD2, NKG2C, LIGHT, DAP12, CD40L, TIM1, CD226, DR3, CD45, CD80, CD86, CD9, CD16, CD22, CD33, CD37, CD64, CD134, CD137, CD154 and SLAM, or a combination thereof. For example, the transmembrane domain can be a transmembrane domain derived from CD8a in the CD8. For example, the transmembrane domain may contain an amino acid sequence as shown in SEQ ID NO: 90.

In certain cases, the chimeric antigen receptor may contain a co-stimulatory signaling domain. The co-stimulatory signaling domain may contain a transmembrane domain derived from a protein selected from the group consisting of CD28, CD137, CD27, CD2, CD7, CD8, CD80, CD86, OX40, CD226, DR3, SLAM, CD5, ICAM, NKG2D, NKG2C, B7-H3, 2B4, FcεRIγ, BTLA, GITR, HVEM, DAP10, DAP12, CD30, CD40, CD40L, TIM1, PD-1, PD-L1, PD-L2, 4-1BBL, OX40L, ICOS-L, CD30L, CD70, CD83, HLA-G, MICA, MICB, a lymphotoxin-β receptor, LFA-1, LIGHT, JAML, CD244, CD100, ICOS, a ligand of CD83, CD40 and MyD88, or a combination thereof. For example, the co-stimulatory signaling domain can be a co-stimulatory signaling domain derived from. For example, the co-stimulatory signaling domain may contain an amino acid sequence as shown in SEQ ID NO: 91.

In certain cases, the chimeric antigen receptor may contain an intracellular signaling domain. For example, the intracellular signaling domain may contain an intracellular signaling domain derived from a protein selected from the group consisting of CD3ζ, CD3δ, CD3γ, CD3ε, CD79a, CD79b, CD66d, CD5, CD22, FcRγ, FcRβ, FcRε, FcεRIγ, FcεRIβ, FcγRIIa, bovine leukemia virus (BLV) gp30, Epstein-Barr virus (EBV) LMP2A, simian immunodeficiency virus (SIV) PBj14 Nef, Kaposi's sarcoma-associated herpesvirus (KSHV) K1, DAP10, DAP12 and a domain containing at least one immunoreceptor tyrosine-based activation motif (ITAM), or a combination thereof. For example, the intracellular signaling domain can be an intracellular signaling domain derived from CD3. For example, the intracellular signaling domain may contain an amino acid sequence as shown in SEQ ID NO: 92.

In the present application, the C-terminus of the signal peptide can be linked to the N-terminus of the targeting moiety.

For example, the N-terminus of the hinge region can be linked to the C-terminus of the targeting moiety.

For example, the N-terminus of the transmembrane domain can be linked to the C-terminus of the hinge region.

For example, the N-terminus of the co-stimulatory signaling domain can be linked to the C-terminus of the transmembrane domain.

For example, the N-terminus of the intracellular signaling domain can be linked to the C-terminus of the co-stimulatory signaling domain.

In the present application, the chimeric antigen receptor may sequentially contain a signal peptide, a target moiety, a hinge region, a transmembrane domain, a co-stimulatory signaling domain and an intracellular signaling domain from the N-terminus to the C-terminus.

For example, the chimeric antigen receptor may sequentially contain a human CD8a signal peptide, a VHH sequence of an anti-human CD70 single domain antibody, a human CD8a hinge region, a CD8a transmembrane domain, a 4-1BB co-stimulatory signaling domain and a CD3ζ intracellular signaling domain from the N-terminus to the C-terminus (as shown in FIG. 1).

In the present application, the chimeric antigen receptor may contain an amino acid sequence as shown in any one of SEQ ID NOs: 60, 61, 62, 63, 64, 65, 66, 67, 68, 69, 71 and 72. For example, the chimeric antigen receptor may contain an amino acid sequence having at least 80% (for example, at least 85%, 90%, 91%, 92%, 93%, 94%, 95%, 96%, 97%, 98%, 99%, or higher) sequence homology to an amino acid sequence as shown in any one of SEQ ID NOs: 60, 61, 62, 63, 64, 65, 66, 67, 68, 69, 70, 71 and 72.

Nucleic Acid, Vector and Cell

In another aspect, the present application also provides one or more isolated nucleic acid molecules, which can encode the isolated antigen-binding protein of the present application. For example, each of the one or more nucleic acid molecules may encode the complete antigen-binding protein, or may encode a portion thereof (for example, HCDRs 1-3, one or more of heavy chain variable regions).

The nucleic acid molecule of the present application can be an isolated nucleic acid molecule. For example, the nucleic acid molecule can be produced or synthesized by the following methods: (i) in vitro amplification, for example, amplification using polymerase chain reaction (PCR), (ii) cloning and recombination, (iii) purification, for example, isolation by enzyme cleavage and gel electrophoresis fractionation, or (iv) synthesis, for example, chemical synthesis. For example, the isolated nucleic acid can be a nucleic acid molecule prepared by a DNA recombination technology.

In the present application, nucleic acids encoding the isolated antigen-binding protein can be prepared by various known methods in the art, including but not limited to using reverse transcription PCR and PCR to obtain the nucleic acid molecule of the isolated antigen-binding fragment of the present application.

In another aspect, the present application provides one or more vectors, which contain one or more of the nucleic acid molecules of the present application. Each vector may contain one or more of the nucleic acid molecules. In addition, the vector may also contain other genes, for example, marker genes that allow the vector to be selected in an appropriate host cell and under appropriate conditions. In addition, the vector may also contain an expression control element that allows a coding region to be correctly expressed in an appropriate host. Such control element is well known to a person skilled in the art, and may comprise, for example, a promoter, a ribosome binding site, an enhancer, and other control elements that regulate gene transcription or mRNA translation. In certain embodiments, the expression control sequence is a regulatable element. The specific structure of the expression control sequence can vary according to the functions of species or cell types, but generally contain a 5' non-transcriptional sequence and 5' and 3' non-translational sequences respectively involved in transcription and translation initiation, such as TATA box, cap sequence and CAAT sequence. For example, a 5' non-transcriptional expression control sequence may contain a promoter region, which may contain a promoter sequence for the transcriptional control of a functionally linked nucleic acid. The expression control sequence may also comprise an enhancer sequence or an upstream activator sequence. In the present application, appropriate promoters may comprise, for example, promoters for SP6, T3 and T7 polymerases, human U6RNA promoters, and CMV promoters and artificial hybrid promoters thereof (such as CMV), wherein certain moiety of the promoter can be fused with certain moiety of gene promoters of other cellular proteins (such as human GAPDH and glyceraldehyde-3-phosphate dehydrogenase), and additional introns may or may not contained. One or more of the nucleic acid molecules of the present application can be operably linked to the expression control element.

The vector may comprise, for example, plasmids, cosmids, viruses, phages, or for example, other common vectors in genetic engineering. For example, the vector can be an expression vector. For example, the vector can be a viral vector. The viral vector can be administered to a patient directly (in vivo) or indirectly. For example, a cell is treated with a virus in vitro and then the treated cell is administered to a patient (ex vivo). The viral vector technology is well known in the art, and has been described in, for example, Sambrook et al. (2001, Molecular Cloning: A Laboratory Manual, Cold Spring Harbor Laboratory, New York) and other virology and molecular biology manuals. Conventional virus-based systems may comprise retroviral vectors, lentiviral vectors, adenoviral vectors, adeno-associated viral vectors, and herpes simplex virus vectors for gene transfer. In certain cases, genes can be transferred and integrated into a host genome using methods of retroviruses, lentiviruses and adeno-associated viruses, allowing for the long-term expression of the inserted genes. Lentiviral vectors are retroviral vectors that can transduce or infect non-dividing cells and typically produce high viral titers. A lentiviral vector may contain a long terminal repeat (5' LTR and truncated 3' LTR), RRE, an rev response element (cPPT), a central termination sequence (CTS), and/or a post-transcriptional regulatory element (WPRE). The vector of the present application can be introduced into a cell.

In another aspect, the present application provides a cell. The cell may contain one or more of the nucleic acid molecules of the present application and/or one or more of the vectors of the present application. The cell may also contain the chimeric antigen receptor or antigen-binding protein of the present application. For example, each type of cells or each cell may contain one or one type of the nucleic acid molecule or vector of the present application. For example, each type of cells or each cell may contain multiple (e.g., 2 or more) or multiple types (e.g., 2 or more types) of the nucleic acid molecules or vectors of the present application. For example, the vector of the present application can be introduced into the host cell, for example, a prokaryotic cell (e.g., a bacterial cell), a CHO cell, an NS/0 cell, an HEK293T cell or an HEK293A cell, or other eukaryotic cells, such as cells from plants, fungus or yeast cells, etc. The vector of the present application can be introduced into the host cell by known methods in the art, such as electroporation, lipofectine transfection and lipofectamin transfection. For example, the cell may comprise a yeast cell. For example, the cell may comprise an *Escherichia coli* cell. For example, the cell may comprise a mammalian cell. For example, the cell may comprise an immune cell.

The cell may comprise an immune cell. In certain cases, the cell may comprise an immune cell. For example, the cell may comprise a T cell, a B cell, a natural killer (NK) cell, a macrophage, an NKT cell, a monocyte, a dendritic cell, a granulocyte, a lymphocyte, a leukocyte, and/or a peripheral blood mononuclear cell.

In certain cases, the cell may comprise a T lymphocyte. The T lymphocyte may comprise a thymocyte, an innate T lymphocyte, an immature T lymphocyte, a mature T lymphocyte, a resting T lymphocyte, or an activated T lymphocyte. The T cell can be a helper T cell (Th), for example, a helper T cell 1 (Th1) or a helper T cell 2 (Th2). The T lymphocyte can be a CD4+ helper T cell (HTL; CD4+ T cell), a cytotoxic T cell (CTL; CD8+ T cell), a tumor-infiltrating cytotoxic T lymphocyte (TIL; CD8+ T cell), a CD4+/CD8+ T cell, a CD4−/CD8− T cell, or any other T lymphocyte subtype. In certain cases, the modified T cell is a human T cell. Prior to expansion and genetic modification of the cells of the present application, cells can be obtained from a subject (e.g., a patient) through a variety of non-limiting methods. T cells can be obtained from a number of non-limiting sources, including peripheral blood mononuclear cells, bone marrow, lymph node tissue, umbilical cord blood, thymus tissue, tissue from a site of infection, ascites, pleural effusion, spleen tissue, and tumors. In certain cases, any number of T cell lines, available and known to a person skilled in the art, can be used. In another case, the cell can be derived from a healthy donor, from a patient diagnosed with cancer or from a patient diagnosed with an infection. In another case, the cell is a portion of a mixed population of cells which present different phenotypic characteristics.

In certain cases, the cell may comprise a B cell. In certain cases, the B cell may comprise an effector B cell (plasma cell) and a memory B cell. The B cell may comprise a B2 cell, a B1 cell, a marginal zone B cell, a follicular B cell, and a regulatory B cell. In certain cases, the immune cell may comprise a macrophage. The B cell may comprise a type I macrophage (M1) and a type II macrophage (such as M2a, M2B and M2c).

In certain cases, the cell may comprise an NK cell. In certain cases, the NK cell may comprise CD56bright and CD56dim. In certain cases, the NK cell may comprise NK1 and NK2. In certain cases, the NK cell may comprise A-NK and NA-NK.

In certain cases, the cell may comprise a white blood cell. White blood cells generally refer to a type of nucleated blood cells that have an active mobility and can migrate from inside blood vessels to outside blood vessels or from tissues outside blood vessels to inside blood vessels. In addition to the blood, white blood cells may also be present in the lymphatic system, spleen, tonsils, and other tissues of the body. In the present application, the white blood cell may comprise a granulocyte (such as neutrophil, eosinophil and basophil), and an agranulocyte (such as lymphocyte, monocyte, macrophage, phagocyte and mast cell).

In certain cases, the cell may comprise a lymphocyte, which may comprise any monocytes or non-phagocytic white blood cells found in blood, lymph and lymphoid tissue, for example, B lymphocytes, T lymphocytes and natural killer (NK) cells.

In certain cases, the cell may comprise a peripheral blood mononuclear cell, which may comprise any cell having a single nucleus in peripheral blood. For example, in the present application, the peripheral blood mononuclear cell may comprise a T cell, a B cell, an NK cell, a lymphocyte, a monocyte and a dendritic cell.

In certain cases, the cell may comprise a macrophage. Macrophages are a type of cells that may phagocytize and digest cell debris, microorganisms, cancer cells, and all other substances that lack surface markers expressed on the surface of normal cells. This process is called phagocytosis. Macrophages are present in almost all tissues and look for possible pathogens through ameboid movement. In addition to playing an important role in non-specific innate immune responses, macrophages can also help initiate acquired immunity by recruiting other types of immune cells, such as lymphocytes.

In certain cases, the cell has a reduced expression and/or activity of CD70 compared to a wild-type cell.

In certain cases, the cell comprises a CD70 knockout compared to a wild-type cell.

For example, CD70 can be knocked out using a zinc finger nuclease (ZFN), a transcription activator-like effector nuclease (TALEN) or a CRISPR-Cas9 system. For example, the use of a Cas9-gRNA system to knock out CD70 can be comprised. The "Cas9-gRNA system" can also be called "CRISPR/Cas9 system", which is a tool for site-specific genome targeting in organisms. For example, the Cas9-gRNA system can be a type II CRISPR/Cas system, which is a prokaryotic adaptive immune response system that uses a non-coding RNA to guide a Cas9 nuclease to induce site-specific DNA cleavage. Through a cellular DNA repair mechanism, this DNA damage can be repaired by means of a non-homologous end-joining DNA repair pathway (NHEJ) or a homology-directed repair (HDR) pathway. The CRISPR/Cas9 system can be used for creating a simple programmable RNA editing method to mediate genome editing in mammalian cells and can be used for generating gene knockout (via insertion/deletion) or gene knockin (via HDR).

Pharmaceutical Composition

In another aspect, the present application provides a pharmaceutical composition. The pharmaceutical composition may contain the chimeric antigen receptor, the isolated antigen-binding protein, the isolated nucleic acid molecule, the vector and the cell of the present application, and/or a pharmaceutically acceptable adjuvant and/or excipient. In the present application, the pharmaceutically acceptable adjuvant may comprise a buffering agent, an antioxidant, a preservative, a low molecular weight polypeptide, a protein, a hydrophilic polymer, an amino acid, a sugar, a chelating agent, a counterion, a metal complex and/or a non-ionic surfactant. Unless incompatible with the immune cell and/or cell population of the present application, any conventional media or reagents can be considered for use in the pharmaceutical composition of the present application. In the present application, the pharmaceutically acceptable excipient may comprise an additive other than a main drug in a pharmaceutical preparation, also called auxiliary material. For example, the excipient may comprise a binder, a filler, a disintegrating agent, and a lubricant in tablets. For example, the excipient may comprise a liquor, a vinegar, a medicinal juice, etc. in traditional Chinese medicine pills. For example, the excipient may comprise a matrix portion of semi-solid preparations such as an ointment and a cream. For example, the excipient may comprise a preservative, an antioxidant, a flavoring agent, a fragrance, a co-solvent, an emulsifier, a solubilizer, an osmotic pressure regulator and a colorant in liquid preparations.

The pharmaceutical composition can be used for treating a disease or disorder associated with the expression of CD70, for example, for treating leukemia (e.g., AML) or kidney cancer.

Use and Method

In another aspect, the present application provides the use of the chimeric antigen receptor, the antigen-binding protein, the isolated nucleic acid molecule, the vector, and/or the cell in the preparation of a drug, wherein the drug is used for treating a disease or disorder associated with the expression of CD70.

In another aspect, the present application provides a method for preventing and/or treating a disease or disorder associated with the expression of CD70, which method comprises: administering to a subject in need thereof an effective amount of the chimeric antigen receptor, the antigen-binding protein, the isolated nucleic acid molecule, the vector, and/or the cell.

In certain cases, the disease or disorder associated with the expression of CD70 comprise leukemia (for example, AML) or kidney cancer.

The pharmaceutical composition and method of the present application can be used in combination with other types of cancer therapies, such as chemotherapy, surgery, radiation and gene therapy. The pharmaceutical composition and method of the present application can be used for other diseases and conditions that depend on the immunological reaction, such as inflammations, immune diseases and infectious diseases.

In another aspect, the present application provides a method for preparing the isolated antigen-binding protein and the chimeric antigen receptor of the present application. The method may comprise culturing the host cell of the present application under a condition that allows the expression of the isolated antigen-binding protein.

For example, an appropriate culture medium, an appropriate temperature and culture time, etc. can be used, and these methods will be understood by an ordinary person skilled in the art.

In certain cases, the method may further comprise a step of harvesting (for example, isolating and/or purifying) the isolated antigen-binding protein of the present application. For example, affinity chromatography can be performed using protein G-sepharose or protein A-sepharose, and the isolated antigen-binding protein can be purified and isolated by gel electrophoresis and/or high-performance liquid chromatography, etc. For example, a fusion protein polypeptide bound to an affinity column can also be eluted by means of methods such as using a high-salt buffer and changing the pH.

In the present application, the subject may comprise humans or non-human animals. For example, the non-human animals can be selected from the group consisting of monkeys, chickens, geese, cats, dogs, mice and rats. In addition, the non-human animals may also comprise any animal species other than humans, for example, livestock animals, rodents, primates, domestic animals or poultry animals. The humans can be Caucasian, African, Asian, Sumerian, or other races, or a hybrid of different races. As another example, the humans can be an old person, an adult, an adolescent, a child or an infant.

The effective amount in humans can be speculated on the basis of the effective amount in experimental animals. For example, Freireich et al. described the relationship between doses in animals and humans (on the basis of the number of milligrams per square meter of body surface area) (Freireich et al., Cancer Chemother. Rep. 50, 219 (1966)). The surface area of the body can be approximately determined from the height and body weight of a patient. Reference can be made to, for example, Scientific Tables, Geigy Pharmaceuticals, Ardsley, N.Y., 537 (1970).

Without being limited by any theory, the examples described below are only for the purpose of explaining the fusion protein, preparation method, use, etc. of the present application, and are not intended to limit the scope of the invention disclosed in the present application.

EXAMPLES

Example 1 Obtaining of Gene Sequence of VHH of Single Domain Antibody Against CD70 and Detection of Affinity Thereof 1.1 Construction of Single Domain Antibody Immune Library:

*Vicugna pacos* was immunized with a recombinant human CD70 antigen having a C-terminal human IgG Fc tag (Acrobiosystems: CDL-H82Q9). A total of four immunizations were performed with an interval of approximately 3 weeks between each immunization. In the first immunization, 0.5 mg of the recombinant human CD70 antigen was uniformly mixed with CFA (a complete Freund's adjuvant) at a ratio of 1:1 and emulsified, and then injected subcutaneously, which was considered as day 1. For the subsequent three immunizations, 0.25 mg of the recombinant human CD70 antigen was uniformly mixed with IFA (an incomplete Freund's adjuvant) at a ratio of 1:1 and emulsified, and then injected subcutaneously, during which the effect of an immunological reaction was evaluated by taking blood samples. On day 70, lymphocytes were isolated from peripheral blood by gradient centrifugation, and lymphocyte RNA was extracted and reverse transcribed into cDNA. The sequence of a heavy chain variable region VHH of the immunoglobulin of *Vicugna pacos* was amplified by two rounds of polymerase chain reaction (PCR), and the amplified VHH was inserted into a phage display vector. The product carrying the gene fragment of the single domain antibody VHH was transformed into competent *Escherichia coli* by electrotransformation, thereby obtaining a single domain antibody immune library.

1.2 Screening of CD70-Specific Antibody Sequences:

Using a phage display technology, single domain antibody molecules were displayed on the surface of phages, and then antigen-specific single domain antibodies were screened out. A 96-well plate was coated with a human CD70His fusion protein (Acrobiosystems: CDL-H82Q9), and 3-5 rounds of screening were performed through Elisa experiments to gradually enrich CD70-specific phages. A large number of positive clones were selected for Elisa detection, and the positive clones were screened and sequenced. The unique clones were determined on the basis of sequence alignment and the sequences thereof were divided into framework regions (FRs) and complementary determining regions (CDRs). Using the above method, a total of 13 high-affinity single domain antibodies (sdAbs) targeting human CD70 were obtained. These 13 antibodies were respectively named CD70-sdAb-1C (amino acid sequence as shown in SEQ ID NO: 34, and nucleotide sequence as shown in SEQ ID NO: 47), CD70-sdAb-1E (amino acid sequence as shown in SEQ ID NO: 35, and nucleotide sequence as shown in SEQ ID NO: 48), CD70-sdAb-1F (amino acid sequence as shown in SEQ ID NO: 36, and nucleotide sequence as shown in SEQ ID NO: 49), CD70-sdAb-1G (amino acid sequence as shown in SEQ ID NO: 37, and nucleotide sequence as shown in SEQ ID NO: 50), CD70-sdAb-1H (amino acid sequence as shown in SEQ ID NO: 38, and nucleotide sequence as shown in SEQ ID NO: 51), CD70-sdAb-3H (amino acid sequence as shown in SEQ ID NO: 39, and nucleotide sequence as shown in SEQ ID NO: 52), CD70-sdAb-5A (amino acid sequence as shown in SEQ ID NO: 40, and nucleotide sequence as shown in SEQ ID NO: 53), CD70-sdAb-5B (amino acid sequence as shown in SEQ ID NO: 41, and nucleotide sequence as shown in SEQ ID NO: 54), CD70-sdAb-5H (amino acid sequence as shown in SEQ ID NO: 42, and nucleotide sequence as shown in SEQ ID NO: 55), CD70-sdAb-7D (amino acid sequence as shown in SEQ ID NO: 43, and nucleotide sequence as shown in SEQ ID NO: 56), CD70-sdAb-H3 (amino acid sequence as shown in SEQ ID NO: 44, and nucleotide sequence as shown in SEQ ID NO: 57), CD70-sdAb-L2 (amino acid sequence as shown in SEQ ID NO: 45, and nucleotide sequence as shown in SEQ ID NO: 58), and CD70-sdAb-L1 (amino acid sequence as shown in SEQ ID NO: 46, and nucleotide sequence as shown in SEQ ID NO: 59).

1.3 Detection of the Affinity of the Antibodies

The C-terminus of the amino acid sequences of CD70-sdAb-1E, CD70-sdAb-1G, CD70-sdAb-3H and CD70-sdAb-L2 were respectively linked to a human Fc domain (as shown in SEQ ID NO: 94), and these 4 proteins fused with Fc were expressed in HEK293 cells. After purification, the affinity of these 4 sdAb-Fc to CD70 protein (ACRO Biosystems, CDL-H82Q9) was detected using Biacore T200 (GE) and Protein A chip (GE, Cat #29127556). The results were as shown in Table 1.

It can be seen from the equilibrium dissociation constant $K_D$ of the antibodies that these screened antibodies all have a high affinity to CD70, with the $K_D$ values all below 1 nM.

TABLE 1

Binding affinity of different single domain antibodies to CD70

| Antibody | Type | Target protein | KD (M) |
|---|---|---|---|
| CD70-sdAb-1E | VHH | CD70 | 1.683E−10 |
| CD70-sdAb-1G | VHH | CD70 | 2.65E−10 |
| CD70-sdAb-3H | VHH | CD70 | 3.005E−10 |
| CD70-sdAb-L2 | VHH | CD70 | 9.757E−10 |

Kidney cancer cell lines 786-0 (expressing CD70) and 786-O-KO (CD70) (in which CD70 gene was knocked out using CRISPR, and therefore CD70 was not expressed) were stained using sdAb-Fc antibody proteins corresponding to different concentrations of CD70-sdAb-1E, CD70-sdAb-1G, CD70-sdAb-3H and CD70-sdAb-L2. The percentage of positive cells was analyzed by flow cytometry, and the curves were plotted as shown in FIGS. 2A-2D, respectively. The calculated EC50 corresponding to these 4 antibodies CD70-sdAb-1E, CD70-sdAb-1G, CD70-sdAb-3H and CD70-sdAb-L2 were 14.14 μg/ml, 5.70 μg/ml, and 11.65 μg/ml, respectively.

Example 2 Whole Gene Synthesis of Chimeric Antigen Receptor Molecules Targeting CD70 and Construction of Lentiviral Expression Vector The obtained 13 sdAbs were respectively constructed into a lentiviral vector to screen out chimeric antigen receptors capable of more effectively targeting CD70.

2.1 Gene Synthesis of Gene Sequences of Chimeric Antigen Receptors Targeting CD70 and Containing Different sdAbs:

The chimeric antigen receptors targeting CD70 specifically comprises: a human CD8a signal peptide, a VHH sequence of a single domain antibody targeting human CD70, a human CD8a hinge region, a CD8a transmembrane domain, a 4-1BB co-stimulatory signaling domain and a CD3 intracellular signaling domain, which are sequentially linked in series (FIG. 1). 13 different chimeric antigen receptor molecules (CAR molecules) were respectively named CD70-CAR-1C (amino acid sequence as shown in SEQ ID NO: 60, and nucleotide sequence as shown in SEQ ID NO: 73), CD70-CAR-1E (amino acid sequence as shown in SEQ ID NO: 61, and nucleotide sequence as shown in SEQ ID NO: 74), CD70-CAR-1F (amino acid sequence as shown in SEQ ID NO: 62, and nucleotide sequence as shown in SEQ ID NO: 75), CD70-CAR-1G (amino acid sequence as shown in SEQ ID NO: 63, and nucleotide sequence as shown in SEQ ID NO: 76), CD70-CAR-1H (amino acid sequence as shown in SEQ ID NO: 64, and nucleotide sequence as shown in SEQ ID NO: 77), CD70-CAR-3H (amino acid sequence as shown in SEQ ID NO: 65, and nucleotide sequence as shown in SEQ ID NO: 78), CD70-CAR-5A (amino acid sequence as shown in SEQ ID NO: 66, and nucleotide sequence as shown in SEQ ID NO: 79), CD70-CAR-5B (amino acid sequence as shown in SEQ ID NO: 67, and nucleotide sequence as shown in SEQ ID NO: 80), CD70-CAR-5H (amino acid sequence as shown in SEQ ID NO: 68, and nucleotide sequence as shown in SEQ ID NO: 81), CD70-CAR-7D (amino acid sequence as shown in SEQ ID NO: 69, and nucleotide sequence as shown in SEQ ID NO: 82), CD70-CAR-H3 (amino acid sequence as shown in SEQ ID NO: 70, and nucleotide sequence as shown in SEQ ID NO: 83), CD70-CAR-L2 (amino acid sequence as shown in SEQ ID NO: 71, and nucleotide sequence as shown in SEQ ID NO: 84), and CD70-CAR-L1 (amino acid sequence as shown in SEQ ID NO: 72, and nucleotide sequence as shown in SEQ ID NO: 85). The gene sequences of the 13 different chimeric antigen receptors targeting CD70 were synthesized by Genewiz Inc. (SuZhou) and cloned into a pUC57 vector (Genewiz Inc. (SuZhou)). To facilitate subsequent construction onto a lentiviral vector, the cleavage sites of restriction endonucleases BamHI (NEB: R3136S) and SalI (NEB: R3138S) were respectively added to the 5' and 3' ends of the genes during gene synthesis. Reference is made to the preparation method of patent CN 111909966 A. The nucleic acid sequence (SEQ ID NO: 93) of CD70-CAR-03 was obtained on the basis of the VL and VH sequences of monoclonal antibody 41D12 targeting CD70 in the existing patent US 20170369581, and the corresponding lentivirus and CAR-T cells were prepared as positive controls in the example.

2.2 Cloning of Gene Sequences of Chimeric Antigen Receptors Targeting CD70 into Lentiviral Vectors:

The gene sequences of the chimeric antigen receptors targeting CD70 were respectively double-enzymatically cleaved from the pUC57 vector using two enzyme cleavage sites, BamHI and SalI, and the enzyme cleavage bands were detected through agarose gel electrophoresis, and then respectively recovered from the gel and purified (QIAGEN: 28706) to obtain the DNA fragments of the chimeric antigen receptors targeting CD70. The enzymatically cleaved and recovered DNA fragments of the chimeric antigen receptors targeting CD70 were cloned into a lentiviral vector pCGK (PCT/CN 2019/090605) using a T4 ligase (NEB: M0202S), and after transformation, enzyme cleavage and sequencing verification, 13 recombinant plasmids containing the gene sequences of the chimeric antigen receptors targeting CD70 were obtained: CD70-CAR-1C-pCGK, CD70-CAR-1E-pCGK, CD70-CAR-1F-pCGK, CD70-CAR-1G-pCGK, CD70-CAR-1H-pCGK, CD70-CAR-3H-pCGK, CD70-CAR-5A-pCGK, CD70-CAR-5B-pCGK, CD70-CAR-5H-pCGK, CD70-CAR-7D-pCGK, CD70-CAR-H3-pCGK, CD70-CAR-L2-pCGK, CD70-CAR-L1-pCGK. The 13 recombinant plasmids were sent to Genewiz Inc. (SuZhou) for sequencing verification, with sequencing primers being:

```
Lenti-For:
                                    (SEQ ID NO: 86)
TCAAGCCTCAGACAGTGGTTC

Lenti-Rev:
                                    (SEQ ID NO: 87)
CCTCATAAAGAGACAGCAACCAGG
```

Sequencing verification showed that all 13 recombinant plasmids were constructed correctly.

Example 3 Preparation of Lentivirus Containing Chimeric Antigen Receptor Molecule Targeting CD70

3.1 Large-Scale Extraction of Recombinant Plasmids:

(1) Transforming recombinant plasmids and shaking bacteria: The correct recombinant plasmids after sequencing verification were re-transformed into *Escherichia coli* stb13 (purchased from CRISPRBIO). On the next day, single clones were picked from the transformed plate and inoculated into 3 ml of a liquid LB medium containing ampicillin in a cell culture tube, and subjected to shake culture on a shaker for 8 h at 30° C. and 220 rpm. The activated bacterial liquid was inoculated into 250 ml of a liquid LB medium containing ampicillin at an inoculation amount of 1:500, and subjected to shake culture on a shaker for 12-16 h at 30° C. and 220 rpm.

(2) Extracting recombinant plasmids: Using Qiagen Hi Speed Plasmid Maxi Kit (Catalog No: 12662), plasmids were extracted according to the experimental procedure provided by the kit.

(3) Detecting the quality of the extracted plasmids: The concentration of the extracted recombinant plasmid was determined using Nanodrop (Thermo Fisher Scientific) to determine the purity of the recombinant plasmid, and the content of the supercoiled plasmid was detected by DNA agarose gel electrophoresis. 3.2 Culture of 293T cells:

Cryopreserved 293T cells (purchased from ATCC) were taken out of liquid nitrogen and constantly shaken in a 37° C. water bath kettle to promote the thawing thereof. After the opening of a cryotube was wiped with disinfectant alcohol, the cells were transferred to a 15 ml centrifuge tube with 10 ml of a preheated DMEM complete medium (90% DMEM+10% FBS+1% penicillin/streptomycin) added thereto, gently blown for uniform mixing, and centrifugated at 1000 rpm for 3 min, and the supernatant was removed by aspiration and discarded. 10 ml of a DMEM complete medium was added, and the cells were gently blown for uniform mixing, then inoculated into a 10 cm culture dish and cultured in a cell culture incubator containing 5% $CO_2$ at 37° C. On the next day, when the cell density reached 80%-90%, the 293T cells were passaged. The culture medium was aspirated using a pipette, and then the 293T cells were washed once with 10 ml of PBS. 3 ml of a trypsin containing 0.25% EDTA was added, and the cells were put in an incubator for 1-2 min (during which the cells needed to be taken out of the incubator for observing whether the cells became round under a microscope). After the cells became round, 1 ml of a DMEM complete medium was added for terminating digestion, the cells were transferred to a 15 ml centrifuge tube, and centrifugated at 1000 rpm for 3 min, and the supernatant was removed by aspiration and discarded. According to requirements of the experiment, cell passage was performed at a ratio of 1:3 or 1:5, and the 293T cells were inoculated into a new 10 cm culture dish for further culture or cryopreservation.

3.3 Inoculation of 293T Cells into Culture Flask:

After culturing and passaging for more than 2 generations, the resuscitated 293T cells can be used for packaging lentiviruses. Firstly, the cultured 293T cells were digested with trypsin and uniformly mixed. According to the counting results, the 293T cells were inoculated at a density of approximate $1.7\times10^7$ cells/T175 flask (cultured in 30 ml of a culture medium), gently shaken for uniform mixing, and then placed in a cell culture incubator containing 5% $CO_2$ at 37° C. for culture overnight until the cell density reached 70%-80% for transfection.

3.4 Transfection of 293T Cells by PEI Method:

On the next day, before plasmid transfection, the culture medium needed to be replaced with a DMEM medium containing 10% FBS but no antibiotics. Firstly, a plasmid complex was prepared: adding 1.5 ml of Opti-MEM (Thermo Fisher Scientific; 31985-070) to a 15 ml centrifuge tube, and then sequentially adding 18 μg of a viral vector plasmid, 9 μg of psPAX2 plasmid (Addgene; Catalog No:12260) and 18 μg of pMD2.G plasmid (Addgene; Catalog No:12259); after adding all the above plasmids, gently and uniformly mixing the mixture; and leaving same to stand for 5 min. There were 13 recombinant viral plasmids (CD70-CAR-1C-pCGK, CD70-CAR-1E-pCGK, CD70-CAR-1F-pCGK, CD70-CAR-1G-pCGK, CD70-CAR-1H-pCGK, CD70-CAR-3H-pCGK, CD70-CAR-5A-pCGK, CD70-CAR-5B-pCGK, CD70-CAR-5H-pCGK, CD70-CAR-7D-pCGK, CD70-CAR-H3-pCGK, CD70-CAR-L2-pCGK, and CD70-CAR-L1-pCGK) need to be packaged into 13 types of viruses, respectively. Secondly, a transfection reagent complex was prepared: adding 67.5 μl (2 mg/ml) of PEI (polysciences: 24765) to 1.5 ml of Opti-MEM and uniformly mixing same; leaving the mixture to stand at room temperature for 5 min; adding a transfection reagent complex to the plasmid complex after completing an incubation; uniformly mixing same, and leaving the mixture to stand for 20 min. Finally, the transfection complex was slowly added dropwise to the 293T cells, gently and uniformly mixed, and cultured in a cell culture incubator containing 5% $CO_2$ at 37° C.

3.5 Collection and Concentration of Lentiviruses:

After transfecting the recombinant plasmids into 293T cells for 48 h, the supernatant of the cell culture medium was collected and transferred into a 50 ml centrifuge tube, and centrifugated at 2000 rpm for 10 min to remove cell debris. The cell supernatant was filtered using a 0.4511m filter membrane (Millipore), and the filtrate was transferred to a dedicated centrifuge tube, and ultracentrifugated at 25000 rpm for 2 h by an ultra-speed centrifuge after balancing. After the ultracentrifugation, the filtrate was discarded, and the lentiviruses were resuspended in a serum-free culture medium, subpacked and then stored in a −80° C. refrigerator. Lentiviruses containing CD70-CAR-1C-pCGK, CD70-CAR-1E-pCGK, CD70-CAR-1F-pCGK, CD70-CAR-1G-pCGK, CD70-CAR-1H-pCGK, CD70-CAR-3H-pCGK CD70-CAR-5A-pCGK, CD70-CAR-5B-pCGK CD70-CAR-5H-pCGK, CD70-CAR-7D-pCGK, CD70-CAR-H3-pCGK, CD70-CAR-L2-pCGK and CD70-CAR-L 1-pCGK were prepared respectively according to the process.

Example 4 Resuscitation of Human Primary T Cells, Knockout of CD70 Gene and then Activation of Cells Human peripheral blood mononuclear cells (PBMCs, purchased from Milestone® Biotechnologies) were taken out of liquid nitrogen, resuscitated and counted. CD70 sgRNA-19 was transduced into the resuscitated T cells using CRISPR/Cas9 electroporation to knock out the CD70 gene in the T cells. The cell processing procedure was performed according to example 3 of patent WO 2019/011118. At the same time, T cells (control T cells) in which CD70 was not knocked out were selected as a negative control. On the next day of gene knockout, a magnetic bead coupled with CD3/CD28 antibody (Thermo Fisher Scientific) was added to the cells at a cell-to-magnetic bead ratio of 1:3 to activate the T cells in which CD70 was knocked out, and 300 IU of IL-2 (PeproTech: 200-02) was added to the culture medium at the same time.

Example 5 Preparation of CD70-Targeting CAR-T Cells with CD70 Knockout

On the next day of cell activation, the T cells in which CD70 was knocked out were counted and then adjusted to a concentration of 1×106/ml, and 50011.1 of the cells was inoculated into each well of a 24-well plate. The lentiviruses containing CD70-CAR-1C-pCGK, CD70-CAR-1E-pCGK, CD70-CAR-1F-pCGK, CD70-CAR-1G-pCGK, CD70-CAR-1H-pCGK, CD70-CAR-3H-pCGK CD70-CAR-5A-pCGK, CD70-CAR-5B-pCGK, CD70-CAR-5H-pCGK, CD70-CAR-7D-pCGK CD70-CAR-H3-pCGK, CD70-

CAR-L2-pCGK, and CD70-CAR-L1-pCGK were respectively added to T-KO cell culture wells to transfect the T cells; untransfected T-KO cells were used as a negative control; and different groups of T cells capable of expressing chimeric antigen receptors targeting the human CD70 antigen were obtained and named CD70 KO-CAR-1C, CD70 KO-CAR-1E, CD70 KO-CAR-1F, CD70 KO-CAR-1G, CD70 KO-CAR-1H, CD70 KO-CAR-3H, CD70 KO-CAR-CD70 KO-CAR-5B CD70 KO-CAR-5H, CD70 KO-CAR-7D, CD70 KO-CAR-H3, CD70 KO-CAR-L2, and CD70 KO-CAR-L1. At the same time, a positive control CAR, a CAR-T cell corresponding to CD70-CAR-03, was prepared according to a similar process, and named CD70KO-CAR-03. The T cells in each group were further cultured to a resting state. At the same time, the CAR-T cells in each group were taken, the genomes of the cells in each group were extracted, and whether CD70 had been successfully knocked out in these CAR-T cells was analyzed and determined by PCR and TIDE. The knockout efficiency of the control T cell CT-KO, and the cells CD70 KO-CAR-1C, CD70 KO-CAR-1E, CD70 KO-CAR-1F, CD70 KO-CAR-1G, CD70 KO-CAR-1H, CD70 KO-CAR-3H, CD70 KO-CAR-CD70 KO-CAR-5B, CD70 KO-CAR-5H, CD70 KO-CAR-7D, CD70 KO-CAR-H3, CD70 KO-CAR-L2 and CD70 KO-CAR-L1 was as shown in Table 2.

TABLE 2

Knockout efficiency of CAR-T cells in different groups

| Name | (%, TIDE analysis) | R2 (TIDE) |
|---|---|---|
| CT-KO | 82.3 | 0.98 |
| CD70 KO-CAR-1C | 88.2 | 0.99 |
| CD70 KO-CAR-1E | 87.7 | 0.99 |
| CD70 KO-CAR-1F | 86.2 | 0.99 |
| CD70 KO-CAR-1G | 90.9 | 0.99 |
| CD70 KO-CAR-1H | 88.9 | 0.99 |
| CD70 KO-CAR-3H | 89.5 | 0.99 |
| CD70 KO-CAR-5A | 86.1 | 0.98 |
| CD70 KO-CAR-5B | 88.5 | 0.99 |
| CD70 KO-CAR-5H | 86.2 | 0.97 |
| CD70 KO-CAR-7D | 88.7 | 0.99 |
| CD70 KO-CAR-H3 | 85.9 | 0.98 |
| CD70 KO-CAR-L2 | 92.6 | 0.99 |
| CD70 KO-CAR-L1 | 85.6 | 0.99 |
| CD70KO-CAR-03 | 89.6 | 0.99 |

Example 6 Detection of Expression of CAR Targeting CD70 in T Cells

Figure 3:
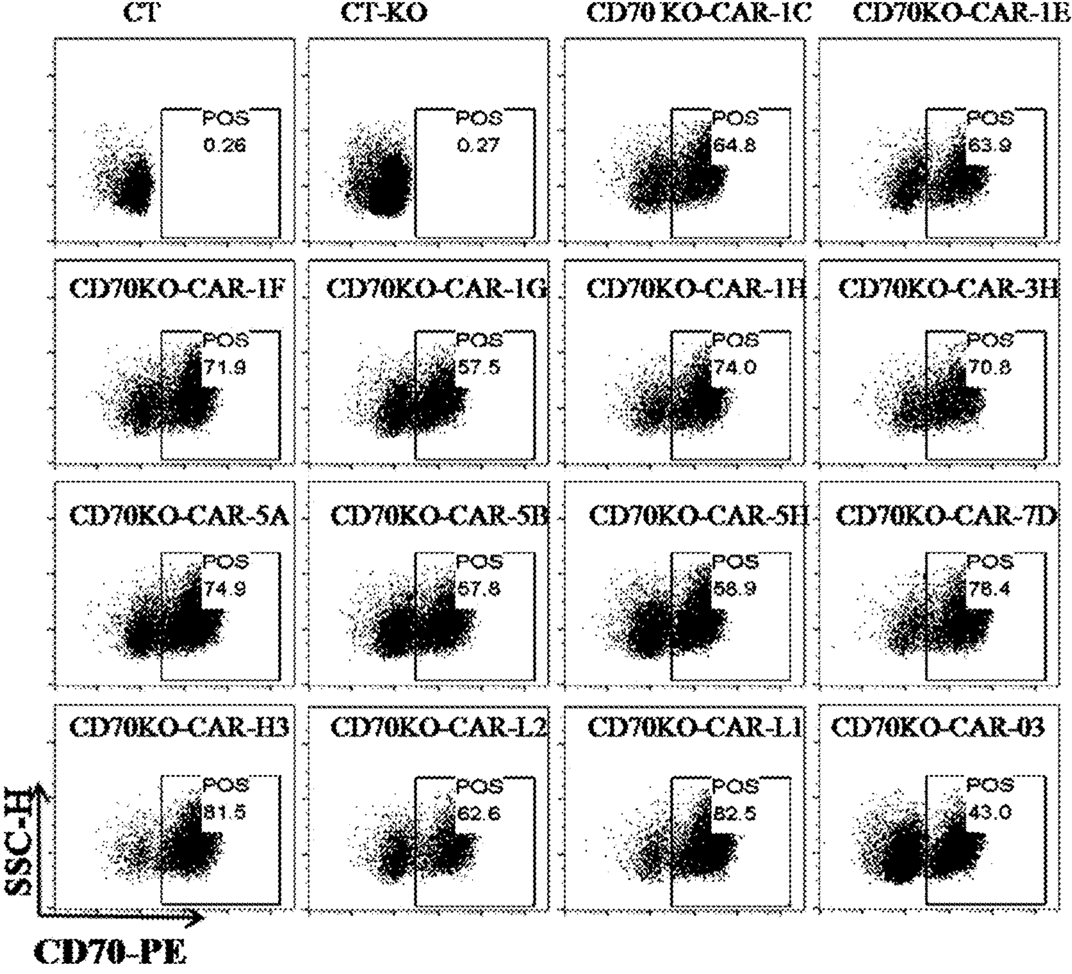
FIG. 3 shows the expression efficiency of the CAR targeting CD70 of the present application on the surface of CD70 knockout T cells as detected by a flow cytometer.

The expression of the CAR targeting CD70 prepared in example 5 in T cells in each group was detected by fluorescence antibody staining and flow cytometry. The specific steps were as follows: CAR-T cells targeting CD70 with lentivirus infection for 48 h, T cells without lentivirus infection and T-KO cells without lentivirus infection were respectively collected by centrifugation; biotinylated human CD70 protein (100 μg/ml) (Acrobiosystems: CDL-H82Q9) was added; and the mixture was incubated at 4° C. in the dark for 30 min, and then washed once with PBS after the incubation. After resuspending in an appropriate volume of PBS, a second antibody PE-Streptavidin (BD Biosciences: 554061) was added to the cells, and the mixture was incubated at 4° C. in the dark for 20 min, washed once with PBS and then resuspended in an appropriate volume of PBS. Finally, the expression efficiency of the CAR targeting CD70 on the surface of the T cells in which CD70 was knocked out was detected using a flow cytometer. The results were as shown in FIG. 3, indicating that the expression efficiency of the CAR targeting CD70 on the surface of the T cells in which CD70 was knocked out was relatively high.

Example 7 Detection of Secretion of Cytokines after Co-Culture of CAR-T Targeting CD70 with Different Target Cells 7.1 Cell co-culture: Firstly, the expression of CD70 in 786-0 cells (purchased from Cell Bank of Chinese Academy of Sciences), THP-1 cells, Raji cells, K562 cells, and 293T cells was detected. A certain volume of cells was taken, stained with an antibody against CD70 and then analyzed by a flow cytometer, and it was found that CD70 was highly expressed in Raji cells, THP-1 cells and 786-0 cells, while CD70 was not expressed in K562 cells and 293T cells. A 293T.CD70 cell line expressing CD70 protein was prepared by transfecting 293T cells with a lentivirus capable of expressing CD70 gene (Genebank: NM 001252.5). See example 3 for the lentiviral preparation process. The 13 types of CAR-T cells targeting CD70 prepared in example 5 (CD70 KO-CAR-1C, CD70 KO-CAR-1E, CD70 KO-CAR-1F, CD70 KO-CAR-1G, CD70 KO-CAR-1H, CD70 KO-CAR-3H, CD70 KO-CAR-5A, CD70 KO-CAR-5B CD70 KO-CAR-5H, CD70 KO-CAR-7D, CD70 KO-CAR-H3, CD70 KO-CAR-L2, and CD70 KO-CAR-L1) and the control T-KO cells were counted and then adjusted to a concentration of 5×10 5/ml. Then, the cells were inoculated into a flat-bottomed 96-well plate at 100 ul/well. 3 replicates were set for each CAR-T cell targeting CD70, and the inoculated CAR-T cells targeting CD70 and the T-KO cells were temporarily placed at 37° C. for incubation. Target cells Raji (purchased from Cell Bank of Chinese Academy of Sciences), 786-0 and THP-1, 293T.CD70 expressing CD70 protein, and negative cells (without CD70 expression) K562 (Cell Bank of Chinese Academy of Sciences) and 293T (ATCC) were added to the CAR-T cells targeting CD70 or control T-KO cells at an effector-to-target ratio of 1:1, i.e., a cell concentration of $5\times10^5$/ml (100 μl/well) for co-culture.

Figure 4:
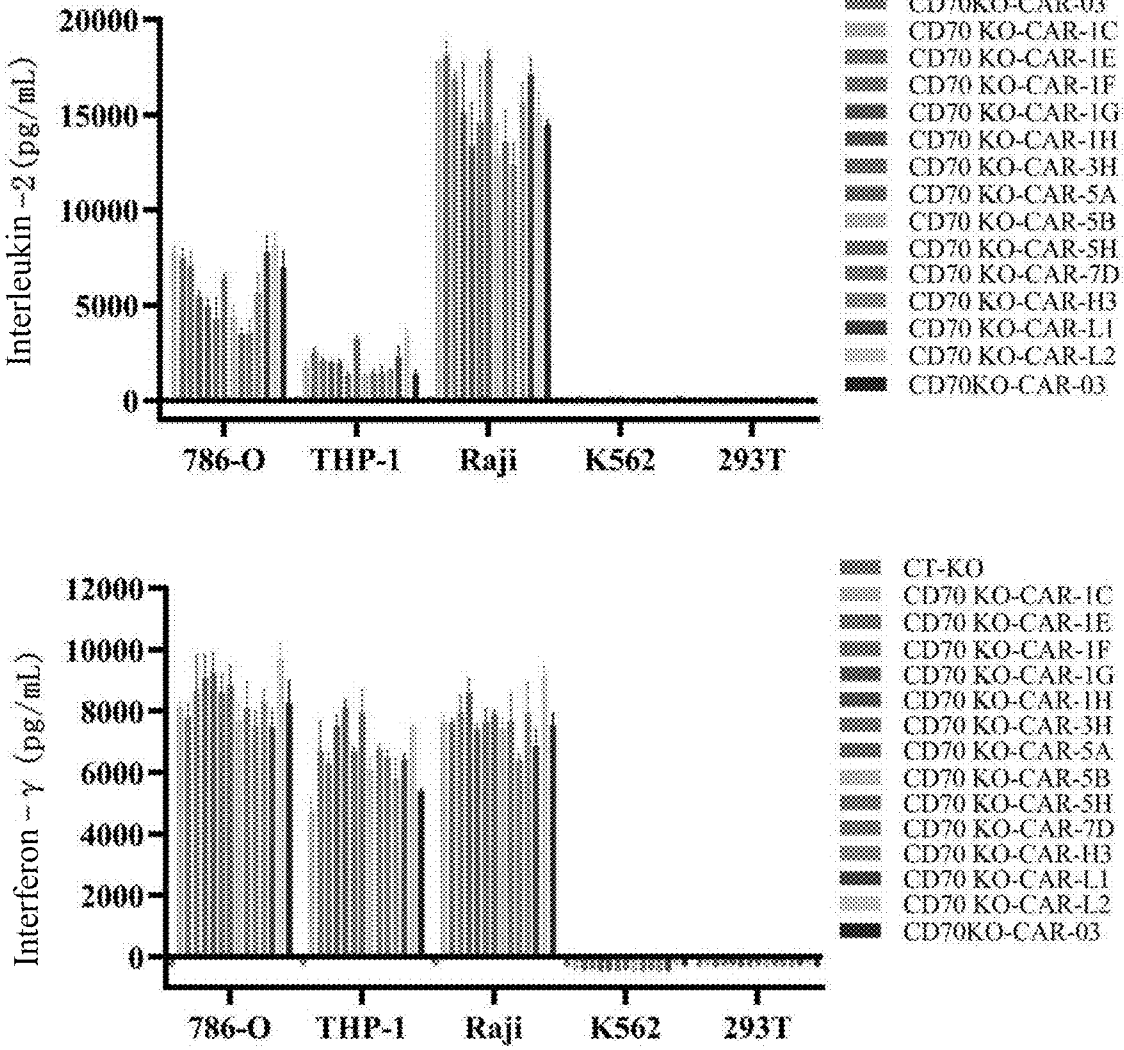
FIG. 4 shows the secretion of cytokines IL-2 and IFN-γ as detected by the Elisa method after the co-culture of the CAR-T cells targeting CD70 of the present application with target cells.

7.2 After co-culturing the above cells for 24 h, the supernatant was transferred to a new 96-well plate, and the secretion of cytokines IL-2 and IFN-γ by the CAR-T cells was detected using an ELISA kit (Thermo Fisher Scientific; Catalog No: 88-7316) according to a standard procedure provided by the kit. The preparation of an ELISA plate and the detection of cytokines in the cell supernatant were performed according to the standard procedure provided by the kit. The results were as shown in FIG. 4, indicating that the co-culture of the CAR-T cells targeting CD70 respectively with cells Raji, THP-1 and 786-0 can cause the secretion of interleukin-2 and interferon-γ.

Example 8 Detection of Killing Ability of CAR-T Targeting CD70 after Co-Culture with Different Target Cells 8.1 Cell plating: 786-0 cells, THP-1 cells, K562 cells, and 293T cells were transfected with a lentivirus carrying luciferase (GenBank: AAR29591.1) to prepare cell lines labeled with luciferase, which were respectively named: 780-O.luc cells, THP-1.luc cells, K562.luc cells, and 293T.luc cells. See example 3 for the lentiviral preparation process. The cell lines labeled with luciferase were plated in a flat-bottomed 96-well opaque white plate at a cell concentration of $1\times10^5$/ml (50 μl/well). Three effector-to-target ratios of 2.5:1, 1:1 and 0.5:1 were set for the co-culture of CAR-T cells targeting CD70 with THP-1 cells; three different effector-to-target ratios of 1:1, 0.5:1 and 0.25:1 were set for the co-culture of CAR-T cells targeting CD70 with 786-0 cells; and three different effector-to-target ratios of 2.5:1, 1:1, and 0.5:1 were set for the co-culture of CAR-T cells targeting CD70 respectively with K562 cells and 293T cells. The CAR-T cells targeting CD70 respectively were CD70 KO-CAR-1C, CD70 KO-CAR-1E, CD70 KO-CAR-1F, CD70 KO-CAR-1G, CD70 KO-CAR-1H, CD70 KO-CAR-3H, CD70 KO-CAR-5A, CD70 KO-CAR-CD70 KO-CAR-5H, CD70 KO-CAR-7D, CD70 KO-CAR-H3, CD70 KO-CAR-L2, and CD70 KO-CAR-L1. Control T-KO cells were co-cultured with the target cells, with 3 replicates for each CAR-T targeting CD70. The 96-well plate was cultured in a 5% $CO_2$ cell culture incubator at 37° C. overnight.

Figure 5:
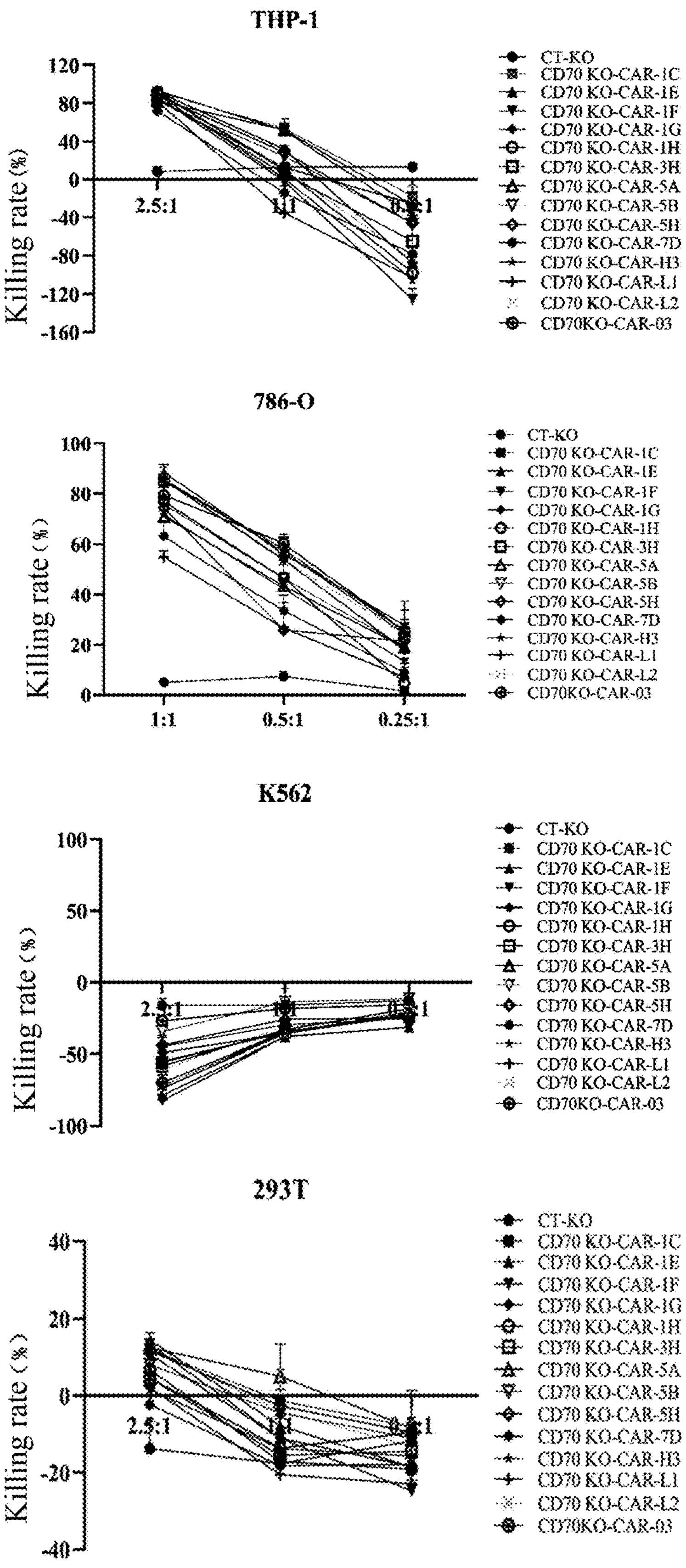
FIG. 5 shows the detection of the killing rate of the CAR-T cells targeting CD70 of the present application to target cells labeled with luciferase after the co-culture of the CAR-T cells targeting CD70 with the target cells.

8.2 After co-culturing the cells for 24 h, the remaining luciferase activity (relative light unit, RLU) of the target cells was determined to detect the killing ability of each CAR-T targeting CD70 on different target cells. The specific steps were as follows: 100 μl of a D-luciferin substrate (Thermo Fisher Scientific: 88293) was directly added to the co-cultured cells, mixed uniformly, and developed in the dark for 5 min, and the fluorescence intensity was detected using a microplate reader in a chemiluminescence mode. In the absence of effector cells, the maximum luciferase activity was obtained by adding target cells to a culture medium as a control. The results were as shown in FIG. 5, indicating that the CAR-T targeting CD70 has a killing effect on THP-1 (acute myeloid leukemia cell line) and 786-O (kidney cancer cell line).

Example 9 Activity of CAR-T Targeting CD70 in Animal Models of Acute Myeloid Leukemia THP-1 Luc tumor cells, which are human acute myeloid leukemia cells expressing luciferase, were amplified and cultured after conventional resuscitation. After at least 2 passages, the cells in a logarithmic growth phase were harvested, and resuspended in a serum-free culture medium. Female NOG mice aged 6-8 weeks were taken and inoculated with 0.1 mL of a PBS suspension containing $5\times10^6$ cells via the tail vein under aseptic conditions. 7-11 days after the tail vein inoculation with THP-1 Luc cells, 33 animals were screened according to the tumor signal intensity, randomly divided into 11 groups and subjected to single intravenous injection with: PBS (buffer group), T-KO (control T cell group), and CD70 KO-CAR-1C, CD70 KO-CAR-1E, CD70 KO-CAR-1F, CD70 KO-CAR-1G, CD70 KO-CAR-3H, CD70 KO-CAR-H3, CD70 KO-CAR-L2, CD70 KO-CAR-L1, and CD70 KO-CAR-03 (positive control), with 3 mice in each group. A preheated 1640 complete medium was prepared in advance and transferred to 15 mL centrifuge tubes, with 5 mL per tube. Cryotubes were removed from a cryopreservation site, and then quickly placed in a 37° C. water bath. The cells were transferred to the 15 mL centrifuge tubes after thawing in the water bath, and uniformly mixed with the culture medium. The appropriate number of cells were taken, and the cell density and viability were counted with Trypan blue. The cells were centrifugated at 1800 rpm for 5 min, and the cell density of the test samples was adjusted with PBS. The animals in each group were injected with the test samples at a dose of $3\times10^6$ T cells (in 200 μl of PBS) per animal (approximately $1.5\times10^6$ CAR-positive cells).

On D7, D14, D21, D28, D35 and D49, all animals were intraperitoneally injected with D-luciferin potassium (150 mg/kg, Thermo Fisher Scientific). 10-15 min after the injection, the chemiluminescent signal was captured by the Bruker small animal imaging system under isoflurane anesthesia, with an imaging time of 180 s.

Figure 6:
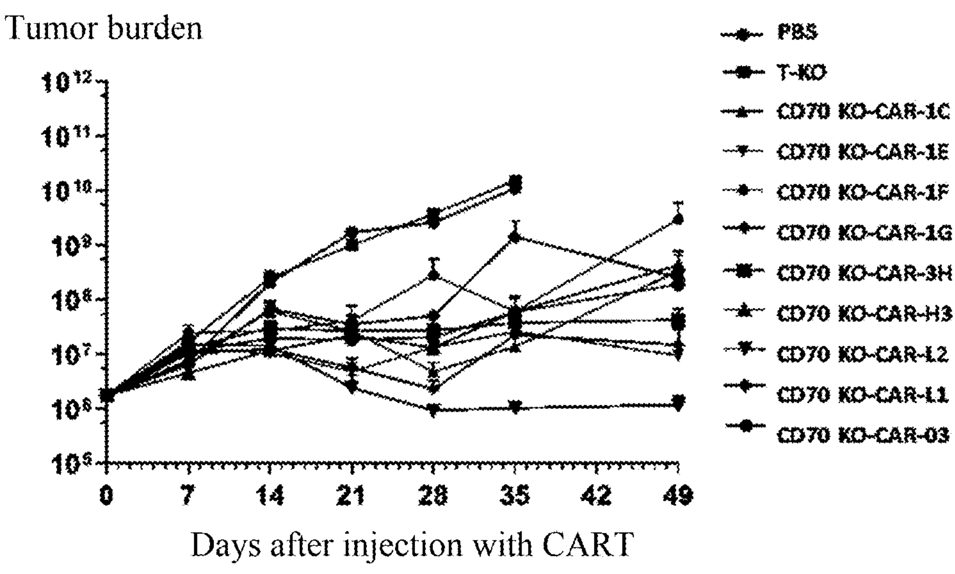
FIG. 6 shows the anti-tumor effect of the CAR-T cells targeting CD70 of the present application in animal models of acute myeloid leukemia.

Results: the experimental results were as shown in FIG. 6. FIG. 6 can show that under the present experimental conditions, CAR-T in all groups can significantly inhibit the proliferation of tumor cells compared to the control T-KO group and buffer group (PBS). Compared with the positive control CD70 KO-CAR-03, these 4 groups CD70 KO-CAR-L2, CD70 KO-CAR-1E, CD70 KO-CAR-1G and CD70 KO-CAR-3H have a stronger anti-tumor activity (Table 3).

TABLE 3

Sorting of average biofluorescence values of mice in each group on day 49 after CAR-T injection (from low to high)

| CAR group | Biofluorescence (photon/second) |
|---|---|
| CD70 KO-CAR-L2 | 800667 |
| CD70 KO-CAR-1E | 9273667 |
| CD70 KO-CAR-1G | 14689667 |
| CD70 KO-CAR-3H | 42893667 |
| CD70 KO-CAR-03 | 193150333 |
| CD70 KO-CAR-L1 | 258283667 |
| CD70 KO-CAR-1C | 340223667 |
| CD70 KO-CAR-H3 | 430557000 |
| CD70 KO-CAR-1F | 2999083667 |

Example 10 Activity of CAR-T Targeting CD70 in Animal Models of Kidney Cancer 786-0 tumor cells, which are human kidney cancer cells, were amplified and cultured after conventional resuscitation. After at least 2 passages, the cells in a logarithmic growth phase were harvested, and resuspended in a serum-free culture medium at a concentration of 1×10 7 cells/mL. 45 female NOG mice aged 6-8 weeks were taken. The 786-0 cells were resuspended in a mixed solution of PBS and Matrigel matrix at a ratio of 1:1. All animals were subcutaneously inoculated with 0.2 mL of the cell suspension (containing 5×10 6 786-0 cells) on the right hind back under aseptic conditions. Approximately 33 days after the inoculation with the 786-0 cells, when the tumor volume reached 120-150 mm 3, 30 animals were screened, randomly divided into 6 groups and subjected to single intravenous injection with: T-KO (control T cell group), and CD70 KO-CAR-1E, CD70 KO-CAR-1G, CD70 KO-CAR-3H, CD70 KO-CAR-L2, and CD70 KO-CAR-03 (positive control), with 5 mice in each group. A preheated 1640 complete medium was prepared in advance and transferred to 15 mL centrifuge tubes, with 5 mL per tube. Cryotubes were removed from a cryopreservation site, and then quickly placed in a 37° C. water bath. The cells were transferred to the 15 mL centrifuge tubes after thawing in the water bath, and uniformly mixed with the culture medium. The appropriate number of cells were taken, and the cell density and viability were counted with Trypan blue. The cells were centrifugated at 1800 rpm for 5 min, and the cell density of the test samples was adjusted with PBS. The animals in each group were injected with the test samples at a dose of $2\times10^6$ T cells (in 200 μl of PBS) per animal (approximately $1\times10^6$ CAR-positive cells). After the injection, the tumor diameter was measured three times a week for calculating the tumor volume, continuously observing until day 41 after the injection.

Figure 7:
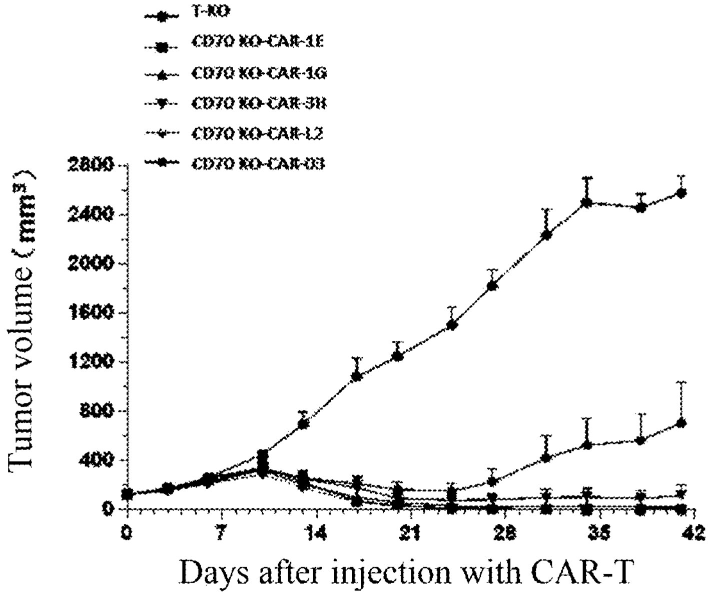
FIG. 7 shows the anti-tumor activity of the CAR-T cells targeting CD70 of the present application in animal models of kidney cancer.

Results: the experimental results were as shown in FIG. 7. FIG. 7 can show that under the present experimental conditions, CAR-T in all groups can significantly inhibit the tumors compared to the control T-KO group. Compared with the positive control CD70 KO-CAR-03, these 4 groups CD70 KO-CAR-1E, CD70 KO-CAR-1G, CD70 KO-CAR-3H, and CD70 KO-CAR-L2 all have a stronger anti-tumor activity, which is consistent with the above results in the animal models of acute myeloid leukemia.

The foregoing detailed description is provided by way of explanation and example, and is not intended to limit the scope of the appended claims. At present, the various changes in the examples listed in the present application would have been obvious to an ordinary person skilled in the art, and are within the scope of the appended claims and the equivalents thereof.

What is claimed is:

1. A chimeric antigen receptor, containing a targeting moiety, wherein the targeting moiety contains a heavy chain complementary determining region 1 (HCDR1), a heavy chain complementary determining region 2 (HCDR2) and a heavy chain complementary determining region 3 (HCDR3), wherein the HCDR1, HCDR2 and HCDR3 comprise amino acid sequences selected from the groups consisting of:

a) HCDR1: SEQ ID NO: 1, HCDR2: SEQ ID NO: 2, and HCDR3: SEQ ID NO: 3;

b) HCDR1: SEQ ID NO: 1, HCDR2: SEQ ID NO: 2, and HCDR3: SEQ ID NO: 4;

c) HCDR1: SEQ ID NO: 1, HCDR2: SEQ ID NO: 2, and HCDR3: SEQ ID NO: 5;

d) HCDR1: SEQ ID NO: 6, HCDR2: SEQ ID NO: 7, and HCDR3: SEQ ID NO: 8;

e) HCDR1: SEQ ID NO: 9, HCDR2: SEQ ID NO: 7, and HCDR3: SEQ ID NO: 10;

f) HCDR1: SEQ ID NO: 11, HCDR2; SEQ ID NO: 12, and HCDR3: SEQ ID NO: 13;

g) HCDR1: SEQ ID NO: 14, HCDR2: SEQ ID NO: 15, and HCDR3: SEQ ID NO: 16;

h) HCDR1: SEQ ID NO: 17, HCDR2: SEQ ID NO: 18, and HCDR3: SEQ ID NO: 19;

i) HCDR1: SEQ ID NO: 20, HCDR2: SEQ ID NO: 21, and HCDR3: SEQ ID NO: 22;

i) HCDR1: SEQ ID NO: 23, HCDR2: SEQ ID NO: 24, and HCDR3: SEQ ID NO: 25;

k) HCDR1: SEQ ID NO: 26, HCDR2: SEQ ID NO: 27, and HCDR3: SEQ ID NO: 28;

l) HCDR1: SEQ ID NO: 29, HCDR2: SEQ ID NO: 30, and HCDR3: SEQ ID NO: 31;

and m) HCDR1: SEQ ID NO: 23, HCDR2: SEQ ID NO: 32, and HCDR3: SEQ ID NO: 33.

2. The chimeric antigen receptor according to claim 1, wherein the targeting moiety comprises a VHH.

3. The chimeric antigen receptor according to claim 1, wherein the targeting moiety contains an amino acid sequence as shown in any one of SEQ ID NOs: 39, 34, 35, 36, 37, 38, 44, 40, 41, 42, 43, 45, and 46.

4. The chimeric antigen receptor according to claim 1, containing a signal peptide.

5. The chimeric antigen receptor according to claim 4, wherein the signal peptide contains a signal peptide derived from a protein selected from the group consisting of CD8, 4-1BB, GM-CSF, CD3Y, CD38, CD38, CD22, CD79a, CD79b and CD66d, or a combination thereof.

6. The chimeric antigen receptor according to claim 4, wherein the signal peptide comprises a signal peptide derived from CD8.

7. The chimeric antigen receptor according to claim 4, wherein the signal peptide contains an amino acid sequence as shown in SEQ ID NO: 88.

8. The chimeric antigen receptor according to claim 4, wherein the C-terminus of the signal peptide is linked to the N-terminus of the targeting moiety.

9. The chimeric antigen receptor according to claim 1, containing a hinge region.

10. The chimeric antigen receptor according to claim 9, wherein the hinge region contains a hinge region derived from a protein selected from the group consisting of CD8, CD28, IgG, 4-1BB, CD4, CD27, CD7, PD-1 and CH2CH3, or a combination thereof.

11. The chimeric antigen receptor according to claim 9, wherein the hinge region comprises a hinge region derived from CD8a in the CD8.

12. The chimeric antigen receptor according to claim 9, wherein the hinge region contains an amino acid sequence as shown in SEQ ID NO: 89.

13. The chimeric antigen receptor according to claim 9, wherein the N-terminus of the hinge region is linked to the C-terminus of the targeting moiety.

14. The chimeric antigen receptor according to claim 1, containing a transmembrane domain.

15. The chimeric antigen receptor according to claim 14, wherein the transmembrane domain contains a transmembrane domain derived from a protein selected from the group consisting of CD8, CD28, 4-1BB, CD4, CD27, CD7, PD-1, CTLA-4, LAG-3, TCRα, TCRβ, TCRγ, TCRδ, CD3ε, CD3δ, CD3γ, CD3ζ, a cytokine receptor, CD5, ICOS, OX40, NKG2D, 2B4, CD244, FcεR, FcεRIγ, BTLA, CD30, GITR, HVEM, DAP10, CD2, NKG2C, LIGHT, DAP12, CD40L, TIM1, CD226, DR3, CD45, CD80, CD86, CD9, CD16, CD22, CD33, CD37, CD64, CD134, CD137, CD154 and SLAM, or a combination thereof.

16. The chimeric antigen receptor according to claim 14, wherein the transmembrane domain comprises a transmembrane domain derived from CD8a in the CD8.

17. The chimeric antigen receptor according to claim 14, wherein the transmembrane domain contains an amino acid sequence as shown in SEQ ID NO: 90.

18. The chimeric antigen receptor according to claim 14, wherein the N-terminus of the transmembrane domain is linked to the C-terminus of the hinge region.

19. The chimeric antigen receptor according to claim 1, containing a co-stimulatory signaling domain.

20. The chimeric antigen receptor according to claim 19, wherein the co-stimulatory signaling domain contains a co-stimulatory signaling domain derived from a protein selected from the group consisting of CD28, CD137, CD27, CD2, CD7, CD8, CD80, CD86, OX40, CD226, DR3, SLAM, CDS, ICAM, NKG2D, NKG2C, B7-H3, 2B4, FcεRIγ, BTLA, GITR, HVEM, DAP10, DAP12, CD30, CD40, CD40L, TIM1, PD-1, PD-L1, PD-L2, 4-1BBL, OX40L, ICOS-L, CD30L, CD70, CD83, HLA-G, MICA, MICB, a lymphotoxin-β receptor, LFA-1, LIGHT, JAML, CD244, CD100, ICOS, a ligand of CD83, CD40 and MyD88, or a combination thereof.

21. The chimeric antigen receptor according to claim 19, wherein the co-stimulatory signaling domain comprises a co-stimulatory signaling domain derived from 4-1BB.

22. The chimeric antigen receptor according to claim 19, wherein the co-stimulatory signaling domain contains an amino acid sequence as shown in SEQ ID NO: 91.

23. The chimeric antigen receptor according to claim 19, wherein the N-terminus of the co-stimulatory signaling domain is linked to the C-terminus of the transmembrane domain.

24. The chimeric antigen receptor according to claim 1, containing an intracellular signaling domain.

25. The chimeric antigen receptor according to claim 24, wherein the intracellular signaling domain contains an intracellular signaling domain derived from a protein selected from the group consisting of CD3ζ, CD3δ, CD3γ, CD3ε, CD79a, CD79b, CD66d, CD5, CD22, FcRγ, FcRβ, FcRε, FcεRIγ, FcεRIβ, FcγRIIa, bovine leukemia virus (BLV) gp30, Epstein-Barr virus (EBV) LMP2A, simian immunodeficiency virus (SIV) PBj14 Nef, Kaposi's sarcoma-associated herpesvirus (KSHV) K1, DAP10, DAP12 and a domain containing at least one immunoreceptor tyrosine-based activation motif (ITAM), or a combination thereof.

26. The chimeric antigen receptor according to claim 24, wherein the intracellular signaling domain comprises an intracellular signaling domain derived from CD32.

27. The chimeric antigen receptor according to claim 24, wherein the intracellular signaling domain contains an amino acid sequence as shown in SEQ ID NO: 92.

28. The chimeric antigen receptor according to claim 24, wherein the N-terminus of the intracellular signaling domain is linked to the C-terminus of the co-stimulatory signaling domain.

29. The chimeric antigen receptor according to claim 1, containing an amino acid sequence as shown in any one of SEQ ID NOs: 60, 61, 62, 63, 64, 65, 66, 67, 68, 69, 70, 71, and 72.

30. An isolated antigen-binding protein specifically binding to CD70 at 1 nM or less of a $K_D$ value, wherein the isolated antigen-binding protein comprises a heavy chain complementary determining region 1 (HCDR1), a heavy chain complementary determining region 2 (HCDR2) and a heavy chain complementary determining region 3 (HCDR3), wherein the HCDR1, HCDR2 and HCDR3 comprise amino acid sequences selected from the groups consisting of:

a) HCDR1: SEQ ID NO: 1, HCDR2: SEQ ID NO: 2, and HCDR3: SEQ ID NO: 3;

b) HCDR1: SEQ ID NO: 1, HCDR2: SEQ ID NO: 2, and HCDR3: SEQ ID NO: 4;

c) HCDR1: SEQ ID NO: 1, HCDR2: SEQ ID NO: 2, and HCDR3: SEQ ID NO: 5;

d) HCDR1: SEQ ID NO: 6, HCDR2: SEQ ID NO: 7, and HCDR3: SEQ ID NO: 8;

e) HCDR1: SEQ ID NO: 9, HCDR2: SEQ ID NO: 7, and HCDR3: SEQ ID NO: 10;

f) HCDR1: SEQ ID NO: 11, HCDR2: SEQ ID NO: 12, and HCDR3: SEQ ID NO: 13;

HCDR1: SEQ ID NO: 14, HCDR2: SEQ ID NO: 15, and HCDR3: SEQ ID NO: 16;

h) HCDR1: SEQ ID NO: 17, HCDR2: SEQ ID NO: 18, and HCDR3: SEQ ID NO: 19;

i) HCDR1: SEQ ID NO: 20, HCDR2: SEQ ID NO: 21, and HCDR3: SEQ ID NO: 22;

i) HCDR1: SEQ ID NO: 23, HCDR2: SEQ ID NO: 24, and HCDR3: SEQ ID NO: 25;

k) HCDR1: SEQ ID NO: 26, HCDR2: SEQ ID NO: 27, and HCDR3: SEQ ID NO: 28;

l) HCDR1: SEQ ID NO: 29, HCDR2: SEQ ID NO: 30, and HCDR3: SEQ ID NO: 31;

and m) HCDR1: SEQ ID NO: 23, HCDR2: SEQ ID NO: 32, and HCDR3: SEQ ID NO: 33.

31. The isolated antigen-binding protein according to claim 30, being an antibody or an antigen-binding fragment thereof.

32. The isolated antigen-binding protein according to claim 31, being a VHH or an antigen-binding fragment thereof.

33. The isolated antigen-binding protein according to claim 31, wherein the antibody is selected from the group consisting of a monoclonal antibody, a chimeric antibody, a humanized antibody and a fully human antibody.

34. The isolated antigen-binding protein according to claim 30, comprising a VHH.

35. The isolated antigen-binding protein according to claim 30, wherein the antigen-binding protein contains an amino acid sequence as shown in any one of SEQ ID NOs: 39, 34, 35, 36, 37, 38, 44, 40, 41, 42, 43, 45, and 46.

36. An isolated nucleic acid molecule encoding the chimeric antigen receptor according to claim 1.

37. The isolated nucleic acid molecule according to claim 36, containing a nucleic acid sequence as shown in any one of SEQ ID NOs: 47-59 and/or SEQ ID NOs: 73-85.

38. A vector, containing the isolated nucleic acid molecule according to claim 36.

39. The vector according to claim 38, comprising a viral vector.

40. The vector according to claim 38, comprising a lentiviral vector.

41. A cell, containing the chimeric antigen receptor according to claim 1.

42. The cell according to claim 41, comprising an immune cell.

43. The cell according to claim 41, wherein the immune cell is selected from the group consisting of a T cell, a B cell, a natural killer cell (NK cell), a macrophage, an NKT cell, a monocyte, a dendritic cell, a granulocyte, a lymphocyte, a leukocyte, and/or a peripheral blood mononuclear cell.

44. The cell according to claim 41, comprising a T cell.

45. The cell according to claim 41, having a reduced expression and/or activity of CD70 compared to a corresponding wild-type cell.

46. The cell according to claim 41, comprising a CD70 knockout compared to a corresponding wild-type cell.

47. A pharmaceutical composition, containing the chimeric antigen receptor according to claim 1.

48. A method for treating cancer, comprising: administering to a subject in need thereof an effective amount of the isolated nucleic acid molecule according to claim 36.

49. The method according to claim 48, wherein the cancer is acute myelogenous leukemia (AML) or kidney cancer.

* * * * *